United States Patent
Marbán et al.

(10) Patent No.: US 9,249,392 B2
(45) Date of Patent: Feb. 2, 2016

(54) METHODS AND COMPOSITIONS FOR MAINTAINING GENOMIC STABILITY IN CULTURED STEM CELLS

(75) Inventors: Eduardo Marbán, Beverly Hills, CA (US); Tao-Sheng Li, Nanchang (CN)

(73) Assignee: Cedars-Sinai Medical Center, Los Angeles, CA (US)

( * ) Notice: Subject to any disclaimer, the term of this patent is extended or adjusted under 35 U.S.C. 154(b) by 541 days.

(21) Appl. No.: 13/096,931

(22) Filed: Apr. 28, 2011

(65) Prior Publication Data

US 2011/0269230 A1 Nov. 3, 2011

Related U.S. Application Data

(60) Provisional application No. 61/330,251, filed on Apr. 30, 2010.

(51) Int. Cl.
*C12N 5/00* (2006.01)
*C12N 5/077* (2010.01)
*C12N 5/0775* (2010.01)

(52) U.S. Cl.
CPC ............ *C12N 5/0657* (2013.01); *C12N 5/0662* (2013.01); *C12N 2500/02* (2013.01); *C12N 2500/38* (2013.01); *C12N 2501/998* (2013.01)

(58) Field of Classification Search
None
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,052,402 A | 10/1991 | Bencini et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |

(Continued)

FOREIGN PATENT DOCUMENTS

| | | |
|---|---|---|
| CN | 1537646 | 10/2004 |
| CN | 1772300 | 5/2006 |

(Continued)

OTHER PUBLICATIONS

Naka et al., Antiox. Redox. Sig., 10(11): 1883-1884 (2008).*
Lin et al., Stem Cell Dev. 14:92-102 (2005).*
Puceat, Antiox. Redox. Sig., 7(11-12):1435-1439 (2005).*
Zha et al., PNAS, 105(27):9302-9306 (2008).*
Duff et al., "CD105 is important for angiogenesis: evidence and potential applications," FASEB J, Jun. 2003, vol. 17(9), pp. 984-992.
Abela et al., A New Method for Isolation of Cardiac Myocytes by Percutaneous Endomyocardial Biopsy, Catheterization and Cardiovascular Diagnosis, 1996, 37:227-230.

(Continued)

*Primary Examiner* — Blaine Lankford
*Assistant Examiner* — Thomas J Visone
(74) *Attorney, Agent, or Firm* — Knobbe Martens Olson & Bear, LLP

(57) ABSTRACT

The present application relates to methods and compositions for the generation of therapeutic cells having reduced incidence of karyotypic abnormalities. In several embodiments cardiac stem cells are cultured in an antioxidant-supplemented media that reduces levels of reactive oxygen species, but does not down regulate DNA repair mechanisms. In several embodiments, physiological oxygen concentrations are used during culture in order to increase the proliferation of stem cells, decrease the senescence of the cells, decrease genomic instability, and/or augment the functionality of such cells for cellular therapies.

10 Claims, 33 Drawing Sheets

(56) References Cited

U.S. PATENT DOCUMENTS

| | | |
|---|---|---|
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,843 B2 | 3/2005 | Moss et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Eckhard |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murry et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,562,972 B2 * | 10/2013 | Edinger et al. ............... 424/93.7 |
| 2002/0061587 A1 | 5/2002 | Anversa |
| 2002/0098167 A1 | 7/2002 | Anversa et al. |
| 2002/0156383 A1 | 10/2002 | Altman et al. |
| 2002/0177772 A1 | 11/2002 | Altman et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0136966 A1 | 7/2004 | Anversa et al. |
| 2004/0153139 A1 | 8/2004 | Altman |
| 2004/0158313 A1 | 8/2004 | Altman |
| 2004/0168341 A1 | 9/2004 | Petersen et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0215991 A1 | 9/2005 | Altman et al. |
| 2005/0255588 A1 | 11/2005 | Young et al. |
| 2005/0260748 A1 * | 11/2005 | Chang et al. ............... 435/366 |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0020758 A1 | 1/2007 | Giacomello et al. |
| 2007/0048383 A1 | 3/2007 | Helmus |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0129296 A1 | 6/2007 | Zhou |
| 2007/0142774 A1 | 6/2007 | Rosenman |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0138416 A1 | 6/2008 | Rauh et al. |
| 2008/0187514 A1 | 8/2008 | Anversa |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0074728 A1 | 3/2009 | Gronthos et al. |
| 2009/0081170 A1 | 3/2009 | Riley |

(56) References Cited

U.S. PATENT DOCUMENTS

| | | |
|---|---|---|
| 2009/0081276 A1 | 3/2009 | Alsberg et al. |
| 2009/0123366 A1 | 5/2009 | Dobson et al. |
| 2009/0136582 A1 | 5/2009 | Albrecht et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Toru et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0081200 A1* | 4/2010 | Rajala et al. .......... 435/377 |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0256105 A1 | 10/2011 | Marbán et al. |
| 2011/0256621 A1 | 10/2011 | Albrecht et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2013/0059006 A1 | 3/2013 | Schmuck et al. |
| 2013/0266543 A1 | 10/2013 | Nadal-Ginard |
| 2013/0288962 A1 | 10/2013 | Anversa et al. |
| 2013/0295060 A1 | 11/2013 | Yang et al. |
| 2013/0309304 A1 | 11/2013 | Nadal-Ginard |

FOREIGN PATENT DOCUMENTS

| | | |
|---|---|---|
| CN | 1785430 | 6/2006 |
| EP | 1254952 | 11/2002 |
| EP | 2182053 | 5/2010 |
| EP | 2228444 | 9/2010 |
| EP | 1631318 | 11/2010 |
| EP | 1650293 | 12/2010 |
| EP | 2371370 | 10/2011 |
| EP | 2385120 | 11/2011 |
| EP | 2446929 | 5/2012 |
| EP | 1945256 | 7/2012 |
| EP | 2094869 | 7/2012 |
| EP | 2486944 | 8/2012 |
| EP | 2277548 | 1/2013 |
| KR | 100830889 | 5/2008 |
| WO | WO 99/49015 | 9/1999 |
| WO | WO 01/26727 | 4/2001 |
| WO | WO 01/48151 | 7/2001 |
| WO | WO 01/76679 | 10/2001 |
| WO | WO 01/76682 | 10/2001 |
| WO | WO 02/09650 | 2/2002 |
| WO | WO 02/13760 | 2/2002 |
| WO | WO 02/051489 | 7/2002 |
| WO | WO 03/006950 | 1/2003 |
| WO | WO 03/008535 | 1/2003 |
| WO | WO 03/049626 | 1/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO2008/036776 | 3/2008 |
| WO | WO 2008/043521 | 4/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO2009/058818 | 5/2009 |
| WO | WO 2009/062143 | 5/2009 |
| WO | WO 2009/062169 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/056116 | 7/2009 |
| WO | WO2009/067644 | 8/2009 |
| WO | WO 2009/100137 | 8/2009 |
| WO | WO 2009/149956 | 12/2009 |
| WO | WO 2009/152111 | 12/2009 |
| WO | WO 2010/028090 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO2011/029092 | 3/2011 |
| WO | WO2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO2011/062244 | 5/2011 |
| WO | WO2011/064354 | 6/2011 |
| WO | WO2011/084460 | 7/2011 |
| WO | WO 2011/121120 | 10/2011 |
| WO | WO2011/127625 | 10/2011 |
| WO | WO 2011/138328 | 11/2011 |
| WO | WO2011/143499 | 11/2011 |
| WO | WO2012/020307 | 2/2012 |
| WO | WO2012/020308 | 2/2012 |
| WO | WO2012/055971 | 5/2012 |
| WO | WO2012/065027 | 5/2012 |
| WO | WO 2012/135253 | 10/2012 |

OTHER PUBLICATIONS

Andersen et al., "Murine 'Cardiospheres' Are Not a Source of Stem Cells with Cardiomyogenic Potential," Stem Cells, 2009, vol. 27, No. 7, pp. 1571-1581.

Anversa et al., Primitive cells and tissue regeneration. Circ. Res. 92:579-92 (2003).

Ausma et al., "Dedifferentiation of atrial cardiomyocytes: from in vivo to in vitro", Cardiovascular Research, Jul. 2002, vol. 55(1), pp. 9-12.

Balser et al., Global parameter optimization for cardiac potassium channel gating models, Biophys. J., Mar. 1990, vol. 57, pp. 433-444.

Balser et al., Local Anesthetics as Effectors of Allosteric Gating, J. Clin. Invest., Dec. 1996, vol. 98(12), pp. 2874-2886.

Barile et al., Cardiac stem cells: isolation, expansion and experimental use for myocardial regeneration. Nat. Clin. Pract. Cardiovasc. Med. 4 Suppl 1: S9-S14 (2007).

(56) References Cited

OTHER PUBLICATIONS

Barile et al., Endogenous Cardiac Stem Cells. Prog. Cardiovas. Dis. 50(1):31-48 (2007).
Barr et al., Gene Therapy, Jan. 1994, vol. 1(1), pp. 51-58.
Barry et al., Differential Expression of Voltage-Gated K+ Channel Subunits in Adult Rat Heart, Circulation Research, 1995, vol. 77, pp. 361-369.
Barth et al., Lentiviral vectors bearing the cardiac promoter of the Na+—Ca2+ exchanger report cardiogenic differentiation in stem cells. Mol. Ther. 16(5):957-964 (2008).
Beltrami et al., "Adult cardiac stem cells are multipotent and support myocardial regeneration," Cell, vol. 114, No. 6, pp. 763-776 (2003).
Beltrami et al., Evidence that human cardiac myocytes divide after myocardial infarction. N. Engl. J. Med. 344: 1750-1757 (2001).
Benardeau et al., Primary culture of human atrial myocytes is associated with the appearance of structural and functional characteristics of immature myocardium. J. Mol. Cell Cardiol. 29: 1307-1320 (1997).
Bird et al., "The human adult cardiomyocyte phenotype", Cardiovascular Research, May 1, 2003, vol. 58(2), pp. 423-434.
Bosnali et al., "Generation of transducible versions of transcription factors Oct4 and Sox2," Biological Chemistry, Walter De Gruyter GmbH & Co., Berlin, DE, vol. 389(7), Jul. 1, 2008, pp. 851-861.
Chen et al., Vascular endothelial growth factor promotes cardiomyocyte differentiation of embryonic stem cells, Am J Physiol Heart Circ Physiol, Oct. 2006, vol. 291(4), pp. H1653-H1658.
Christmann et al., Biomaterials for the Treatment of Myocardial Infarction, J. Am. Coll. of Cardiol. (2006) vol. 48(5): 907-913.
De Pomerai et al., Influence of serum factors on the prevalence of "normal" and "foreign" differentiation pathways in cultures of chick embryo neuroretinal cells, J Embryol Exp Morphol., 1981, vol. 62, pp. 291-308.
Deal et al., Molecular Physiology of Cardiac Potassium Channels, Physiological Reviews, Jan. 1996, vol. 76(1), pp. 49-67.
Dispersyn et al., Adult rabbit cardiomyocytes undergo hibernation-like dedifferentiation when co-cultured with cardiac fibroblasts. Cardiovasc. Res. 57: 230-240 (2001).
Dispersyn et al., Dissociation of cardiomyocyte apoptosis and dedifferentiation in infarct border zones. Eur. Heart J. 23:849-857 (2002).
Dixon et al., Quantitative Analysis of Potassium Channel mRNA Expression in Atrial and Ventricular Muscle of Rats, Circulation Research, 1994, vol. 75, pp. 252-260.
Dixon et al., Role of the Kv4.3 K+ Channel in Ventricular Muscle, Circulation Research, 1996, vol. 79, pp. 659-668.
Donahue et al., Ultrarapid, highly efficient viral gene transfer to the heart, Proc. Natl. Acad. Sci. USA 94:4664-4668 (1997).
Driesen et al., Structural adaptation in adult rabbit ventricular myocytes: influence of dynamic physical interaction with fibroblasts. Cell. Biochem. Biophys. 44: 119-128 (2006).
Driesen et al., Structural remodeling of cardiomyocytes in the border zone of infarcted rabbit heart. Mol. Cell. Biochem (2007).
Engel et al., "p38 MAP kinase inhibition enables proliferation of adult mammalian cardiomyocytes", Genes & Dev., May 2005, vol. 19, No. 10, pp. 1175-1187.
Engel et al., FGF1/p38 MAP kinase inhibitor therapy induces cardiomyocyte mitosis, reduces scarring, and rescues function after myocardial infarction, Proc Nat Acad Sci (USA), Oct. 17, 2006, vol. 103(42), pp. 15546-15551.
Eschenhagen et al., Engineering Myocardial Tissue, Circ Res (2005) vol. 97:1220-1231.
Fiset et al., Shal-type channels contribute to the Ca2+—independent transient outward K+ current in rat ventricle, J. Physiology, 1997, vol. 500(1), pp. 51-64.
Gidh-Jain et al., Differential Expression of Voltage-Gated K+ Channel Genes in Left Ventricular Remodeled Myocardium After Experimental Myocardial Infarction, Circulation Research, 1996, vol. 79, pp. 669-675.
Glover et al., Reduction of infarct size and postschemic inflammation from ATL-146e, a highly selective adenosine A2A receptor agonist in reperfused canine myocardium, Amer J Physiol Heart Circ Physiol, Apr. 2005, vol. 288(4), pp. H1851-H1858.
Good et al., β-Amyloid Peptide Blocks the Fast-Inactivating K+ Current in Rat Hippocampal Neurons, Biophysical Journal, Jan. 1996, vol. 70, pp. 296-304.
Harvey, "Molecular Determinants of Cardiac Development and Congenital Disease," Mouse Development, Patterning, Morphogenesis, and Organogensis, Chapter 16, pp. 331-370.
Heng et al., "Incorporating protein transduction domains (PTD) within recombinant 'fusion' transcription factors. A novel strategy for directing stem cell differentiation?" Biomedicine and Pharmacotherapy, Elsevier, Paris, FR, vol. 59(3), Apr. 1, 2005, pp. 132-134.
Jackson et al., Regeneration of ischemic cardiac muscle and vascular endothelium by adult stem cells, J Clin Invest., 2001, vol. 107(11), pp. 1395-1402.
Kaab et al., Ionic mechanism of action potential prolongation in ventricular myocytes from dogs with pacing-induced heart failure. Circulation Research, vol. 78, No. 2, 262 (1996).
Kim et al., "Generation of human induced pluripotent stem cells by direct delivery of reprogramming proteins," Cell Stem Cell, Jun. 5, 2009, vol. 4(6), pp. 472-476.
Kuhn et al., Periostin induces proliferation of differentiated cardiomyocytes and promotes cardiac repair, Nature Medicine, Aug. 2007, vol. 13(8), pp. 962-969. Abstract only.
Kwon et al., "Cellular Manipulation of Human Embryonic Stem Cells by TAT-PDX1 Protein Transduction," Molecular Therapy, Academic Press, San Diego, CA, US, vol. 12(1), Jul. 1, 2005, pp. 28-32.
Lee et al., Cardiac gene transfer by intracoronary infusion of adenovirus vector-mediated reporter gene in the transplanted mouse heart. J. Thorac, and Cardio. Surg., 111:246 (1996).
Li et al., Expansion of human cardiac stem cells in physiological oxygen improves cell production efficiency and potency for myocardial repair, Cardiovascular Research, Aug. 21, 2010.
Li et al., Molecular, Cellular, and Functional Phenotypes of Human Cardiac Stem Cells Dependent Upon Monolayer Versus Three-Dimensional Culture Conditions, Circulation Research, Dec. 4, 2009, vol. 105(12).
Li et al., Stem Cell Technology: Epigenetics, Genomics, Proteomics, and Metabonomics, Stem Cells 2010; vol. 28, pp. 1178-1185.
Lyngbaek et al., Cardiac regeneration by resident stem and progenitor cells in the adult heart. Basic Res. Cardiol. 102: 101-114 (2007).
Maletic-Savatic et al., Differential Spatiotemporal Expression of K+ Channel Polypeptides in Rat Hippocampal Neurons Developing in situ and in vitro, Journal of Neuroscience, May 1995, vol. 15(5), pp. 3840-3851.
Marban, Big cells, little cells, stem cells: agents of cardiac plasticity. Circ Res. 100(4):445-6 (2007).
Marshall et al., The Jellyfish Green Fluorescent Protein: A New Tool for Studying Ion Channel Express and Function, Neuron, 1995, vol. 14, pp. 211-215.
McGann et al., Mammalian myotube dedifferentiation induced by newt regeneration extract. Proc. Natl. Acad. Sci. USA 98, 13699-704 (2001).
Messina et al., Isolation and Expansion of Adult Cardiac Stem Cells from Human and Murine Heart; Oct. 29, 2004; pp. 911-921; vol. 95; Circulation Research; Cellular Biology; American Heart Association.
Montessuit et al., "Regulation of glucose transporter expression in cardiac myocytes: p38 MAPK is a strong inducer of GLUT4", Cardiovascular Research, Oxford University Press, Oct. 1, 2004, vol. 64(1), pp. 94-104.
Montessuit et al., "Retinoic acids increase expression of GLUT4 in dedifferentiated and hypertrophied cardiac myocytes", Basic Research in Cardiology, Steinkopff-Verlag, DA, Jan. 1, 2006, vol. 101(1), pp. 27-35.
Nadal-Ginard et al, Myocyte death, growth, and regeneration in cardiac hypertrophy and failure. Circ. Res. 92(2):139-50 (2003).
Nadal-Ginard et al., A matter of life and death: cardiac myocyte apoptosis and regeneration. J. Clin. Invest. 111: 1457-9 (2003).
Odelberg, Inducing cellular dedifferentiation: a potential method for enhancing endogenous regeneration in mammals., Semin Cell Dev. Biol., 13(5):335-43 (2002).

(56) References Cited

OTHER PUBLICATIONS

Odelberg et al., Dedifferentiation of mammalian myotubes induced by msx1. Cell 103(7):1099-1109 (2000).

Oh et al., "Cardiac muscle plasticity in adult and embryo by heart-derived progenitor cells," Annals of the New York Academy of Sciences, vol. 1015, pp. 182-189 (2004).

Oh et al., Cardiac progenitor cells from adult myocardium: homing, differentiation, and fusion after infarction, Proc Natl Acad Sci USA, 2003, vol. 100(21), pp. 12313-12318.

Passier et al., Origin and use of embryonic and adult stem cells in differentiation and tissue repair. Cardiovasc. Res. 58(2):324-35 (2003).

Plotnikov et al., Biologial Pacemaker Implanted in Canine Left Bundle Branch Provides Ventricular Escape Rhythms that Have Physiologically Acceptable Rates, Circulation, Feb. 3, 2004, vol. 109, pp. 506-512.

Potapova et al., Enhanced recovery of mechanical function in the canine heart by seeding an extracellular matrix patch with mesenchymal stem cells committed to a cardiac lineage, Am. J. Phys. (2008) vol. 295:H2257-H2263.

Ribera, Homogeneous Development of Electrical Excitability via Heterogeneous Ion Channel Expression, Journal of Neuroscience, Feb. 1, 1996, vol. 16(3), pp. 1123-1130.

Risepro et al., Hand1 regulates cardiomyocyte proliferation versus differentiation in the developing heart, Development, Nov. 2006, vol. 133(22), pp. 4595-4606. Abstract only.

Rucker-Martin et al., Dedifferentiation of atrial myocytes during atrial fibrillation: role of fibroblast proliferation in vitro. Cardiovasc. Res. 55: 38-52 (2002).

Rudy, Diversity and Ubiquity of K Channels, Neuroscience, 1988, vol. 25(3), pp. 729-749.

Serodio et al., Cloning of a Novel Component of A-Type K+ Channels Operating at Subthreshold Potentials With Unique Expression in Heart and Brain, Journal of Neurophysiology, May 1996, vol. 75(5), pp. 2174-2179.

Smith et al., Regenerative potential of cardiosphere-derived cells expanded from percutanerous endomyocardial biopsy specimens, Circulation, Feb. 20, 2007, vol. 115(7), pp. 896-908.

Smith et al., Cells in the heart: what's the buzz all about? Part 1: Preclinical considerations. Heart Rhythm 5(5):749-757(2008).

Smith et al., Stem Cells in the heart: what's the buzz all about? Part 2: Arrhythmic risks and clinical studies. Heart Rhythm 5(6):880-887 (2008).

Srivastava et al., Thymosin beta4 is cardioprotective after myocardial infarction, Ann NY Acad Sci, Sep. 2007, vol. 1112, pp. 161-170. Abstract only.

Sussman et al., Myocardial aging and senescence: where have the stem cells gone? Annu Rev. Physiol. 66:29-48 (2004).

Takahashi et al., "Induction of pluripotent stem cells from adult human fibroblasts by defined factors," Cell, Cell Press, Cambridge, MA, US, vol. 131(5), Nov. 30, 2007, pp. 861-872.

Tomita et al., Cardiac Neural Crest Cells Contribute to the Dorman Multipotent Stem Cell in the Mammalian Heart, Journal of Cell Biology, Sep. 26, 2005, vol. 170, No. 7, pp. 1135-1148.

Torella et al., Cardiac stem cell and myocyte aging, heart failure, and insulin-like growth factor-I overexpression. Circ. Res 94:514-24 (2004).

Torella et al., Resident human cardiac stem cells: role in cardiac cellular homeostasis and potential for myocardial regeneration. Nat. Clin. Pract. Cardiovasc. Med. 3 Suppl 1:S8-13 (2006).

Urbanek et al., Cardiac Stem Cells Possess Growth Factor Receptor Systems That After Activation Regenerate the Infarcted Myocardium, Improving Ventricular Function and Long-term Survival. Circ. Res. 97:663-673 (2005).

Urbanek et al., Intense myocyte formation from cardiac stem cells in human cardiac hypertrophy. Proc. Natl. Acad. Sci. USA 100(18):10440-5 (2003).

Urbanek et al., Myocardial regeneration by activation of multipotent cardiac stem cells in ischemic heart failure. Proc. Natl. Acad. Sci. USA 102(24):8692-7 (2005).

Ventura et al., Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts, JBC (2007) vol. 282(19):14243-14252.

Von Harsdorf, Can cardiomyocytes divide? Heart 86: 481-482 (2001).

Wagner, The state of the art in antisense research, Nature Medicine, Nov. 1995, vol. 1(11), pp. 1116-1118.

Walder et al., Up-regulation of neural stem cell markers suggests the occurrence of dedifferentiation in regenerating spinal cord. Dev. Genes Evol. 213: 625-630 (2003).

Web page titled: bioptome.com—Scholten Surgical Instructions; downloaded from <http://www.bioptome.com/pages.php?page=Products>, 2001, first date of publication unknown, printed on Nov. 1, 2005.

Wu et al., Cellular Therapy and Myocardial tissue engineering: the role of adult stem and progenitor cells. Eur. J. of Cardio-Thoracic Surg. 30:770-781 (2006).

Yu et al., "Induced pluripotent stem cell lines derived from human somatic cells," Science, American Association for the Advancement of Science, US, vol. 318(5858), Dec. 21, 2007, pp. 1917-1920.

Zammit et al., The skeletal muscle satellite cell: stem cell or son of stem cell? Differentiation 68: 193-204 (2001).

Zhang et al., "Do cardiac stem cells arise from cardiomyocyte dedifferentiation?", Circulation Research, Nov. 2006, vol. 99(11), p. 1278. Abstract only.

Zhou et al., "Generation of Induced Pluripotent Stem Cells Using Recombinant Proteins," Cell Stem Cell, Cell Press, US, vol. 4(5), May 1, 2009, pp. 381-384.

Abdel-Latif, A., et al., Adult bone marrow-derived cells for cardiac repair: a systematic review and meta-analysis. Arch Intern Med, 2007. 167(10): p. 989-97.

Ames BN, Shigenaga MK, Hagen TM. Oxidants, antioxidants, and the degenerative diseases of aging. Proc Natl Acad Sci USA. 1993;90:7915-7922.

Alibini et al., A Rapid in Vitro Assay for Quantitating the Invasive Potential of Tumor Cells, Cancer Research, vol. 47:3239-3245 (1987).

Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, 108:863-868. American Heart Association, Inc.

Bearzi et al, Human Cardiac Stem Cells, PNAS, vol. 104(35): 14068-14073 (2007).

Bernanke, et al., Effects of Hyaluronic Acid on Cardioc Cushion Tissue Cells in Collagen Matrix Cultures, Texas Reports on Biology and Medicine, vol. 39:271-285 (1979).

Bergmann O, Bhardwaj RD, Bernard S, Zdunek S, Barnabe-Heider F, Walsh S, Zupicich J, Alkass K, Buchholz BA, Druid H, Jovinge S, Frisen J. Evidence for cardiomyocyte renewal in humans. Science. 2009;324:98-102.

Birks EJ, Tansley PD, Hardy J, George RS, Bowles CT, Burke M, Banner NR, Khaghani A, Yacoub MH. Left ventricular assist device and drug therapy for the reversal of heart failure. N Engl J Med. 2006;355(18):1873-1884.

Bjelakovic G, Nikolova D, Gluud LL, Simonetti RG, Gluud C. Mortality in randomized trials of antioxidant supplements for primary and secondary prevention: systematic review and meta-analysis. JAMA. 2007;297:842-857.

Bredemeyer AL, Sharma GG, Huang CY, et al. ATM stabilizes DNA double-strand-break complexes during V(D)J recombination. Nature. 2006;442:466-470.

Cai et al., "Injectable glycosaminoglycan hydrogels for controlled release of human basic fibroblast growth factor," Biomaterials (2005), 26:6054-6067, Elsevier Ltd.

Chambers et al., Functional Expression Cloning of Nanog, a Pluripotency Sustaining Facot in Embryonic Stem Cells, Cell. May 30, 2003; 113(5):643-55.

Chen CS, Wells PG. Enhanced tumorigenesis in p53 knockout mice exposed in utero to high-dose vitamin E. Carcinogenesis. 2006;27:1358-1368.

(56) References Cited

OTHER PUBLICATIONS

Cheng K, Li TS, Malliaras K, Davis DR, Zhang Y, Marban E. Magnetic targeting enhances engraftment and functional benefit of iron-labeled cardiosphere-derived cells in myocardial infarction. Circ Res. 2010;106:1570-1581.
Chimenti et al., "Relative Roles of Direct Regeneration Versus Paracrine Effects of Human Cardiosphere-Dervied Cells Transplanted Into Infarcted Mice," Circulation Research (2010) 106:971-980, American Heart Association, Inc.
Chimenti, I., et al., Abstract 3182: Paracrine Contribution versus Direct Regeneration in Cardiosphere-Derived Cell Therapy for Acute Myocardial Infarction. Circulation, 2009. 120(18_MeetingAbstracts): p. S756-a-.
ClinicalTrials.gov, Identifier NCT00893360. CADUCEUS—Cardiosphere—Derived aUtologous Stem CElls to Reverse ventricUlar dySfunction.
Conkright et al., A gene encoding an intestinal-enriched member of the Kruppel-like factor family expressein in intestinal epithelia cells, Nucleic Acids Res. 27 (5), 1263-1270 (1999).
Crisostomo et al., "Embryonic stem cells attenuate myocardial dysfunction and inflammation after surgical global ischemia via paracrine actions," Am J Physiol Heart Cirl Physiol (2008) 295:H1726-H1735.
Davis DR, Kizana E, Terrovitis J, Barth AS, Zhang Y, Smith RR, Miake J, Marban E. Isolation and expansion of functionally-competent cardiac progenitor cells directly from heart biopsies. J Mol Cell Cardiol. 2010;49:312-321.
Davis DR, Zhang Y, Smith RR, et al. Validation of the cardiosphere method to culture cardiac progenitor cells from myocardial tissue. PLoS One. 2009;4:e7195.
Davis, D.R., R.R. Smith, and E. Marban, Human Cardiospheres are a Source of Stem Cells with Cardiomyogenic Potential. Stem Cells, 2010. 28(5): p. 903-4.
Dong et al. (1991) Mol. Endocrinol. 5:1633.
Drakos SG, Kfoury AG, Hammond EH, Reid BB, Revelo MP, Rasmusson BY, Whitehead KJ, Salama ME, Selzman CH, Stehlik J, Clayson SE, Bristow MR, Renlund DG, Li DY. Impact of mechanical unloading on microvasculature and associated central remodeling features of the failing human heart. J Am Coll Cardiol. 2010;56(5):382-391.
Eguchi (2004) Med. Res. Rev. 24:182.
Elliot & O'Hare, 88 Cell 223-233 (1997).
Elliot & O'Hare, Intercellular Trafficking of VP22-GFP fusion proteins., Gene Therapy 6:149 (1999).
Falck J, Coates J, Jackson SP. Conserved modes of recruitment of ATM, ATR and DNAPKcs to sites of DNA damage. Nature. 2005;434:605-611.
Fehrer C, Brunauer R, Laschober G, et al. Reduced oxygen tension attenuates differentiation capacity of human mesenchymal stem cells and prolongs their lifespan. Aging Cell. 2007;6:745-757.
Foreman J, Demidchik V, Bothwell JH, et al. Reactive oxygen species produced by NADPH oxidase regulate plant cell growth. Nature. 2003;422:442-446.
Frankel & Pabo, Cell 55:1189-93 (1988).
Freyman et al., "A quantitative, randomized study evaluating three methods of mesenchymal stem cell delivery following myocardial infarction," European Heart Journal, 2006, 27:1114-1122.
Furlani D, Li W, Pittermann E, et al. A transformed cell population derived from cultured mesenchymal stem cells has no functional effect after transplantation into the injured heart. Cell Transplant. 2009;18:319-331.
Galli, R., et al., Neural stem cells: an overview. Circ Res, 2003. 92(6): p. 598-608.
George RS, Sabharwal NK, Webb C, Yacoub MH, Bowles CT, Hedger M, Khaghani A, Birks EJ. Echocardiographic assessment of flow across continuous-flow ventricular assist devices at low speeds. J Heart Lung Transplant. 2010.
Gomez-Marquez et al. (1987) J. Immunol. 143:2740.
Green & Loewenstein, Cell 55:1179-88 (1988).
Grossman W, Braunwald E, Mann T, McLaurin LP, Green LH. Contractile state of the left ventricle in man as evaluated from end-systolic pressurevolume relations. Circulation. 1977;56:845-852.
Gu, Bispecific Antibody Targeted Stem Cell Therapy for Myocardial Repair, University of California San Francisco and University of California Berkeley, 2008.
Gubbay et al., Nature, 6281:245-50 (1990).
Hacein-Bey-Abina et al., Science 2003; 302:415-9.
Hagege, A.A., et al., Skeletal myoblast transplantation in ischemic heart failure: long-term follow-up of the first phase I cohort of patients. Circulation, 2006. 114(1 Suppl): p. I108-13.
Hainsworth AH, Bhuiyan N, Green AR. The nitrone disodium 2,4-sulphophenyl-N-tert-butylnitrone is without cytoprotective effect on sodium nitroprusside-induced cell death in N1E-115 neuroblastoma cells in vitro. J Cereb Blood Flow Metab. 2008;28:24-28.
Haider, et al., Bone Marrow Stem Cell Transplantation for Cardiac Repair, Am. J. Phys. Heart Circ. Physiol., vol. 288:H2557-H2567 (2005).
Haj-Yahia S, Birks EJ, Dreyfus G, Khaghani A. Limited surgical approach for explanting the HeartMate II left ventricular assist device after myocardial recovery. J Thorac Cardiovasc Surg. 2008;135(2):453-454.
Hochedlinger et al., Nature 441:1061-7(2006).
Ivanovic Z. Hypoxia or in situ normoxia: The stem cell paradigm. J Cell Physiol. 2009;219:271-275.
Johnston PV, Sasano T, Mills K, Evers R, Lee ST, Smith RR, Lardo AC, Lai S, Steenbergen C, Gerstenblith G, Lange R, Marban E. Engraftment, differentiation, and functional benefits of autologous cardiosphere-derived cells in porcine ischemic cardiomyopathy. Circulation. 2009;120:1075-1083.
Jutkiewicz et al. (2006) Mol. Interven. 6:162.
Kyrtatos et al., Magnetic Tagging Increases Delivery of Circulating Progenitors in Vascular Injury, J. Am. Coll. Cardiol. Intv. vol. 2:794-802 (2009).
Lee et al., Antibody Targeting of Stem Cells to Infarcted Myocardium, Stem Cells Translational and Clinical Research, vol. 25:712-717 (2007).
Levenberg at al., Endothelial cells derived from human embryonic stem cells, PNAS, vol. 99(7): 4391-4396 (2002).
Lum et al., The New Face of Bispecific Antibodies: Targeting Cancer and Much More, Exp. Hematol., vol. 24:1-6 (2006).
Martens et al., "Percutaneous Cell Delivery Into the Heart Using Hydrogels Polymerizing in Situ," Cell Transplantation (2009), 18:297-304.
Payne, Using Immunomagnetic Technologi and Other Means to Facilitate Stem Cell Homing, Medical Hypotheses, vol. 62:718-720 (2004).
Quevedo, H.C., et al., Allogeneic mesenchymal stem cells restore cardiac function in chronic ischemic cardiomyopathy via trilineage differentiating capacity. Proc Natl Acad Sci U S A, 2009. 106(33): p. 14022-7.
Shu et al., Disulfide-crosslinked hyaluronon-gelatin hydrogel films: a covalent mimic of the extracellular matrix for in vitro cell growth, Biomaterials, vol. 24:3825-3834 (2003).
Terrovitis, J.V., R.R. Smith, and E. Marban, Assessment and optimization of cell engraftment after transplantation into the heart. Circ Res. 106(3): p. 479-94.
Van Winkle et al, "Cardiogel: A Biosynthetic Extracellular Matrix for Cardiomyocyte Culture," In Vitro Dev. Biol.—Animal, vol. 21, 1996, pp. 478-485.
Zhao et al., Targeting Human CD34+ Hematopoietic Stem Cells With Anti-CD45 x Anti-Myosin Light-chain Bispecific Antibody Preserves Cardiac Function in Myocardial Infarction, J. Appl. Phsyiol., vol. 104:1793-1800 (2008).
Assmus, et al., Transplantation of Progenitor Cells and Regeneration Enhancement in Acute Myocardial Infarction (TOPCARE-AMI), Circulation, vol. 106: 3009-3017 (2002).
Baker DE, Harrison NJ, Maltby E, et al. Adaptation to culture of human embryonic stem cells and oncogenesis in vivo. Nat Biotechnol. 2007;25:207-215.
Cho et al., Secondary Sphere Formation Enhances the Functionality of Cardiac Progenitor Cells, Mol. Ther., vol. 20(9):1750-1766 (2012).

(56) References Cited

OTHER PUBLICATIONS

Cheng et al., Transplantation of platelet gel spike with cardiosphere-derived cells boosts structural and functional benefits relative to gel transplantation alone in rats with myocardial infarction, Biomaterials, vol. 33:2872-2879 (2012).
Cheng, et al., Functional performance of human cardiosphere-derived cells delivered in an in situ polymerizable hyaluronan-gelatin hydrogel, Biomaterials (2012), doi10.1016/j.biomaterials.2012.04.006.
Hergenreider et al., Atheroprotective communication between endothelial cells and smooth muscle cells through miRNAs, Nat. Cell Biol., vol. 14(3):249-256 (2012).
Lavon N, Narwani K, Golan-Lev T, et al. Derivation of euploid human embryonic stem cells from aneuploid embryos. Stem Cells. 2008;26:1874-1882.
Levine M, Conry-Cantilena C, Wang Y, et al. Vitamin C pharmacokinetics in healthy volunteers: evidence for a recommended dietary allowance. Proc Natl Acad Sci USA. 1996;93:3704-3709.
Li, T-S et al., Direct comparison of different stem cell types and subpopulations reveals superior paracrine potency and myocardial repair efficacy with cardiosphere-derived cells, J. Am. Coll. Cardiol., vol. 59(10):942-953 (2012).
Li Z., et al., Imaging survival and function of transplanted cardiac resident stem cells. J Am Coll Cardiol, 2009. 53(14): p. 1229-40.
Lin et al., Accelerated Growth and Prolonged Lifespan of Adipose Tissue-Derived Human Mesenchymal Stem Cells in a Medium Using Reduced Calcium and Antioxidants, Stem Cells and Development, vol. 14:92-102 (2005).
Maitra A, Arking DE, Shivapurkar N, et al. Genomic alterations in cultured human embryonic stem cells. Nat Genet. 2005;37:1099-1103.
Miller ER 3rd, Pastor-Barriuso R, Dalal D, et al. Meta-analysis: high-dosage vitamin E supplementation may increase all-cause mortality. Ann Intern Med. 2005;142:37-46.
Niethammer P, Grabher C, Look AT, Mitchison TJ. A tissue-scale gradient of hydrogen peroxide mediates rapid wound detection in zebrafish. Nature. 2009;459:996-999.
Owusu-Ansah E, Banerjee U. Reactive oxygen species prime *Drosophila haematopoietic* progenitors for differentiation. Nature. 2009;461:537-541.
Prestwich, et al., The translational imperative: Making Cell Therapy Simple and Effective, Acta Biomaterialia, vol. 8: 4200-4207 (2012).
Qin K, Zhao L, Ash RD, McDonough WF, Zhao RY. ATM-mediated transcriptional elevation of prion in response to copper-induced oxidative stress. J Biol Chem. 2009;284:4582-4593.
Rossi DJ, Bryder D, Seita J, et al. Deficiencies in DNA damage repair limit the function of haematopoietic stem cells with age. Nature. 2007;447:725-729.
Rubio D, Garcia-Castro J, Martin MC, et al. Spontaneous human adult stem cell transformation. Cancer Res. 2005;65:3035-3039.
Sareen D, McMillan E, Ebert AD, et al. Chromosome 7 and 19 trisomy in cultured human neural progenitor cells. PLoS One. 2009;4:e7630.
Sesso HD, Buring JE, Christen WG, et al. Vitamins E and C in the prevention of cardiovascular disease in men: the Physicians' Health Study II randomized controlled trial. JAMA. 2008;300:2123-2133.
Shenje, L.T., et al., Lineage tracing of cardiac explant derived cells. PLoS One, 2008. 3(4): p. e1929.
Ulloa-Montoya, et al., Culture Systems for Pluripotent Stem Cells, J. Biosci. and Bioeng., vol. 100(1): 12-27 (2005).
van Gent DC, Hoeijmakers JH, Kanaar R. Chromosomal stability and the DNA double stranded break connection. Nat Rev Genet. 2001;2:196-206.
Web Page titled; Culture Media Database—EGM-2 (Endothelial Growth Medium 2)—ID 63; downloaded from <http://bio.lonza.com/3018.html#ext-comp-1003:tab_63:change>; printed on Jan. 14, 2013.

Deregibus, et al., Endotheial progentior cell-derived microvesicles activate an angiogenic program in endothelial cells by a horizontal transfer of mRNA.
Dong et al., Islet Cell and Extrapancreatic Expression of the LIM Domain Homeobox Gene isl-1, (1991) Mol. Endocrinol. 5:1633.
Eppenberger-Eberhardt et al., Reexpression of alpha-Smooth Muscle Acting Isoform in Culture Adult Rat Cardiomyocytes. Developmental Biology 139, 269-278, 1990.
Gatti et al., Microvesicles derived from human adult mesenchymal stem cells protect against ischaemiareperfusion-induced acute and chronic kidney injury, Nephrol. Dial. Transplant., vol. 26(5):1474-1483 (2011).
Herrera et al., Human liver stem cell-derived microvesicles accelerate hepatic regeneration in hepatectomized rats, J. Cell. Mol. Med., vol. 14(6B):1605-1618 (2010).
Hierlihy et al., The Post-natal Heart Contains a Myocardial Stem Cell Population, FEBS Letters, vol. 530(1-3):239-243 (2002).
Hullinger et al., Inhibition of miR-15 protects against cardiac ischemic injury, Circ. Res. vol. 110(1):71-81 (2012).
Jayawardena et al., MicroRNA-mediated in vitro and in vivo direct reprogramming of cardiac fibroblasts to cardiomyocytes, Circ. Res. vol. 110(11)L1465-73 (2012).
Karlsson et al., Insulin gene enhancer binding protein Isl-1 is a member of a novel class of proteins containing both a homeo-and a Cys-His domain. Nature 344 (6269), 879-882 (1990).
Karoubi et al., "Single-cell hydrogel encapsulation for enhanced survivial of human marrow stromal cells," Biomaterials, 2009, 30:5445-5455, Elsevier Ltd.
Kutschka, et al., Collagen Matrices Enhance Survival of Transplanted Cardiomyoblasts and Contribute to Functional Improvement of Ischemic Rat Hearts, Circulation, vol. 114:I167-I173 (2006).
Laflamme et al., Cardiomyocytes derived from human embryonic stem cells in pro-survival factors enhnce function of infarcted rat hearts. Nat Biotechnology 25:1015-24 (2007).
Landazuri, N. and J.M. Le Doux, Complexation of retroviruses with charged polymers enhances gene transfer by increasing the rate that viruses are delivered to cells. J Gene Med, 2004. 6(12): p. 1304-19.
Leferovich et al. Heart regeneration of adult MRL mice. (2001) Proc. Natl. Acad. Sci. USA 98:9830-9835.
Leor et al., Transplantation of Fetal Myocardial Tissue Into the Infarcted Myocardium of Rat, Circulation, vol. 94(9): II-332 (1996).
Liao et al., Enhanced efficiency of generating induced pluipotent stem (iPS) cells from human somatic cells by a combination of six transcription factors, Cell Research (2008), vol. 18: 600-603.
Lindsay, Mark A. Peptide-mediated cell delivery: application in protein target validation. Curr. Op. Pharmacol. 2:587-94 (2002).
Lindsley et al. The PI3K/Akt Pathway: Recent Progress in the development of ATP-competitive and allosteric Akt kinase inhibitors. (2008) Curr. Cancer Drug Targets 8:7.
Lipinski, M.J., et al., Impact of intracoronary cell therapy on left ventricular function in the setting of acute myocardial infarction: a collaborative systematicreview and meta-analysis of controlled clinical trials. J Am Coll Cardiol, 2007. 50(18): p. 1761-7.
Lowrey et al.,Generation of human induced pluripotent stem cells from dermal fibroblasts. Proc Natl Acad Sci USA 105:2883-8 (2008).
Mangi et al., Mesenchymal stem cells modified with Akt prevent remodeling and restore performance of infarcted hearts, Nature Medicine, Sep. 2003, 9(9):1195-1201, Nature Publishing Group.
Mehmel et al. The linearity of the end-systolic pressure-volume relationship in man and its sensitivity for assessment of left ventricular function. Circulation. 1981;63:1216-1222.
Mitsui et al., The homeoprotein nanog is required for maintenance of pluripotency in mouse epiblase and ES cells. Cell. May 30, 2003; 113(5):631-42.
Miyazono et al. Latent high molecular weight complex of transforming growth factor β1(1988) J. Biol. Chem. 263:6407-6415.
Moss et al., Conservation of the heterochronic regulator Lin-28, its developmental expression and microRNA complementary sites. Dev. Biol. 258 (2), 432-442 (2003).
Moss, A.J., et al., Prophylactic implantation of a defibrillator in patients with myocardial infarction and reduced ejection fraction. N Engl J Med, 2002. 346(12): p. 877-83.

(56) References Cited

OTHER PUBLICATIONS

Murata et al. C4d deposition and cellular infiltrates as markers of acute rejection in rat models of orthotopic lung transplantation. Transplantation. 2008;86:123-129.

Nakagawa et al., Generation of induced pluripotent stem cells without Myc from mouse and human fibroblasts. Nat Biotechnology 26:101-6 (2008).

Nakasa et al., Acceleration of muscle regeneration by local injection of muscle-specific microRNAs in rat skeletal muscle injury model, J. Cell. Mol. Med., vol. 14(10): 2495-2505 (2010).

Nelson et al., CXCR4+/FLK-1+ biomarkers select a cardiopoietic lineage from embryonic stem cells. Stem Cells 26:1464-73 (2008).

Nelson, T.J., et al., Repair of acute myocardial infarction by human stemness factors induced pluripotent stem cells. Circulation, 2009. 120(5): p. 408-16.

Noguchi et al., Protein Transduction Technology: A Novel Therepeautic Perspective, Acta Medica Okayama (2005) vol. 60(1): 1-11.

Nussbaum, J., et al., Transplantation of undifferentiated murine embryonic stem cells in the heart: teratoma formation and immune response. Faseb J, 2007. 21(7):p. 1345-57.

Okita et al., Generation of Mouse Induced Pluripotent Stem Cells Without Viral Vectors, (2008), Science Express, 322:949-53 (Oct. 9, 2008).

Park et al., Reprogramming of human somatic cells to pluripotency with defined factors. Nature 451:141-6 (2008).

Passier et al. Stem-cell-based therapy and lessons from the heart. (2008) Nature 453:322.

Peterson et al. Risk stratification after myocardial infarction. Ann Intern Med, 1997. 126(7): p. 561-82.

Physicians ATSACoC. ATS/ACCP Statement on Cardiopulmonary Exercise Testing. American Journal of Respiratory and Critical CareMedicine. 2003;167:211-277.

Pike et al., Herparin-regulated release of growth factors in vitro and angiogenic response in vivo to implanted hyaluronan hydrogels containing VEGF and bFGF, Biomaterials, (2006) 27:5242-5241, Elsevier Ltd.

Prunier et al. Delayed erythropoietin therapy reduces post-MI cardiac remodeling only at a dose that mobilizes endothelial progenitor cells. Am J Physiol Heart Circ Physiol 292:H522-H529 (2007).

Quaini et al., Chimerism in the transplanted heart, New England J. of Med., vol. 346(1): 5-15 (2002).

Rotwein et al. Organization and sequence of the human insulin-like growth factor I gene. (1986) J. Biol. Chem. 261:4828-4832.

Sharkey et al. Stage-specific expression of cytokine and receptor messenger ribonucleic acids in human preimplantation embryos. (1995) Biol. Reprod. 53:955-962).

Shen et al. Isolation of an insulin-like growth factor II cDNA with a unique 5' untranslated region from human placenta. (1988) Proc. Natl. Acad. Sci. USA 85:1947-1951.

Shimizu et al., Fabrication of Pulsatile Cardiac Tissue Grafts Using a Novel 3-D Cell Sheet Manipulation Techniques and Temperature-Responsive Cell Culture Surfaces, Circ. Res., vol. 90(3);e40 (2002).

Simpson et al. A tissue engineering approach to progenitor cell delivery results in significant cell engraftment and improved myocardial remodeling. (2007) Stem Cells 25:2350-2357.

Singh. Enabling Technologies for Homing and Engraftment of Cells for Therapeutic Applications. J Am Coll Cardiol Intv. 2009;2(8):803-804.

Singh et al. High-dose alpha-tocopherol therapy does not affect HDL subfractions in patients with coronary artery disease on statin therapy. Clin Chem. 2007;53:525-528.

Slaughter MS, Pagani FD, Rogers JG, Miller LW, Sun B, Russell SD, Starling RC, Chen L, Boyle AJ, Chillcott S, Adamson RM, Blood MS, Camacho MT, Idrissi KA, Petty M, Sobieski M, Wright S, Myers TJ, Farrar DJ. Clinical management of continuous-flow left ventricular assist devices in advanced heart failure. J Heart Lung Transplant. 2010;29(4 Suppl):S1-39.

Smart et al., De novocardiomyocytes from within the activated adult heart after injury. Nature. (2011) pp. 1-7.

Stewart et al. Revision of the 1990 working formulation for the standardization of nomenclature in the diagnosis of heart rejection, J Heart Lung Transplant. 2005;24:1710-1720.

Takahasi K et al., Induction of pluripotent stem cells from adult human fibroblasts by defined factors, Cell 131(5):861-872 (2007).

Takeda et al., Human Oct3 gene family: cDNA sequences, alternative splicing, gene organization, chromosomal location, and expression at low levels in adult tissues. Nucleic Acids Res. vol. 20 (17), 4613-4620 (1992).

Takehara et al., Controlled delivery of basic fibroblast growth factor promotes human cardiosphere-derived cell engraftment to enhance cardiac repair for chronic myocardial infarction. J. Am. Coll. Cardiol. (2008) vol. 52:1858-65.

Takeshita et al. Osteoblast-specific factor 2: cloning of a putative bone adhesion protein with homology with the insect protein fasciclin I. (1993) Biochem. J. 294:271-278.

Ten Dijke et al. Identification of another member of the transforming growth factor type β gene family. (1988) Proc. Natl. Acad. Sci. USA vol. 85 pp. 4715-4719.

Terrovitis et al. Noninvasive quantification and optimization of acute cell retention by in vivo positron emission tomography after intramyocardial cardiac-derived stem cell delivery. J Am Coll Cardiol. 2009;54:1619-1626.

Trevethick et al., Treating lung inflammation with agonists of the adenosine $A_{2A}$ receptor: promises, problems and potential solutions. (2008) Br J Pharmacol. 155:463-474.

Tsagalou et al. Depressed coronary flow reserve is associated with decreased myocardial capillary density in patients with heart failure due to idiopathic dilated cardiomyopathy. J Am Coll Cardiol. 2008;52(17):1391-1398.

Uemura et al., Bone marrow Stem Cells Prevent Left Ventricular Remodeling of Ischemic Heart Through Paracrine Signaling. Circulation Research, 2006, 98:1414-1421, American Heart Association.

Ueno S. et al., Biphasic role for WNT/beta-catenin signaling in cardiac specification in zebrafish and embyonic stem cells. PNAS 104L9685 (2007).

van der Geest, R, Quantification in Cardiac MRI, Journal of Magnetic Resonance Imaging, 10:602-608(1999).

Vela, et al., Quest for the cardiovascular holy grail: mammalian myocardial regeneration, Cardiovasc. Pathol. 17:1-5 (2008).

Vrijsen, et al., Cardiomyocyte progenitor cell-derived exosomes stimulate migration of endothelial cells, J. Cell. Mol. Med., vol. 14(5):1064-1070 (2010).

Wang et al. The LIM domain homeobox gene isl-1: Conservation of human, hamster, and rat complementary deoxyribonucleic acid sequences and expression in cell types of nonneuroendocrine lineage. (1994) Endocrinol. vol. 134:1416-1422.

Wang et al. Establishment of new mouse embryonic stem cell lines is improved by physiological glucose and oxygen. Cloning Stem Cells. 2006;8:108-116.

Wernig el al., C-Myc is dispensable for direct reprogramming of mouse fibroblasts. Cell Stem Cell 2: 10-2 (2008).

Wilmut et al., Viable offspring derived from fetal and adult mammalian cells. Nature 385:810-813 (1997).

Wilson et al. Bioluminescence reporter gene imaging of human embryonic stem cell survival, proliferation, and fate. Methods Mol Biol. 2009;574:87-103.

Yamada et al. Type v collagen-induced oral tolerance plus low-dose cyclosporine prevents rejection of mhc class i and ii incompatible lung allografts. J Immunology. 2009;1:237-246 8.

Yau et al., Beneficial Effect of Autologous Cell Transplantation on Infarcted Heart Function: Comparison Between Bone Marrow Stromal Cells and Heart Cells, Annals of Thoracic Surg, vol. 75(1):169 (2003).

Yu et al., miR-221 and miR-222 promote Schwann cell proliferation and migration by targeting LASS2 after sciatic nerve injury, J. Cell Sci., vol. 125(11) 2675-2683 (2012).

Zhou et al., Down-Regulation of microRNA-26a Promotes Mouse Hepatocyte Proliferation during Liver Regeneration, PLoS ONE, vol. 7(4):e33577 (2012).

* cited by examiner

A

Trisomy 8

B

Trisomy 7

C

Trisomy 2, and 20

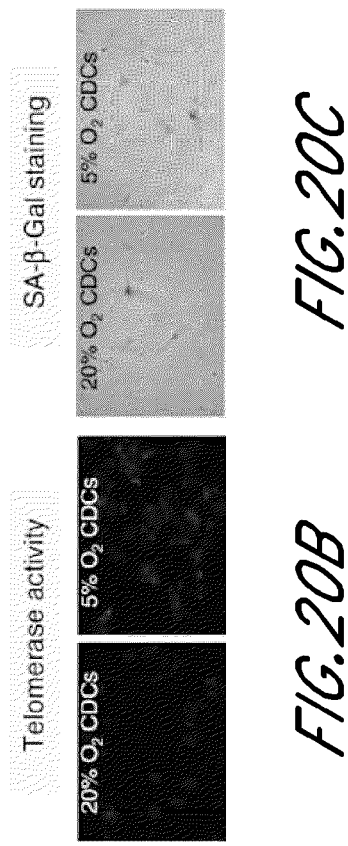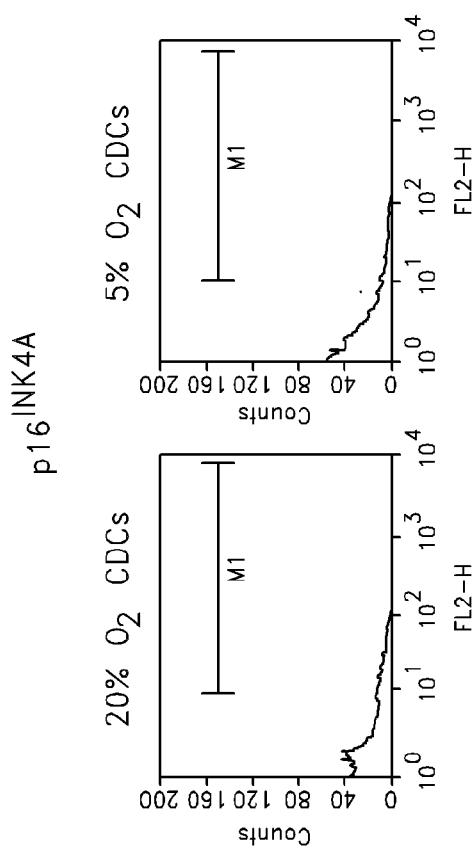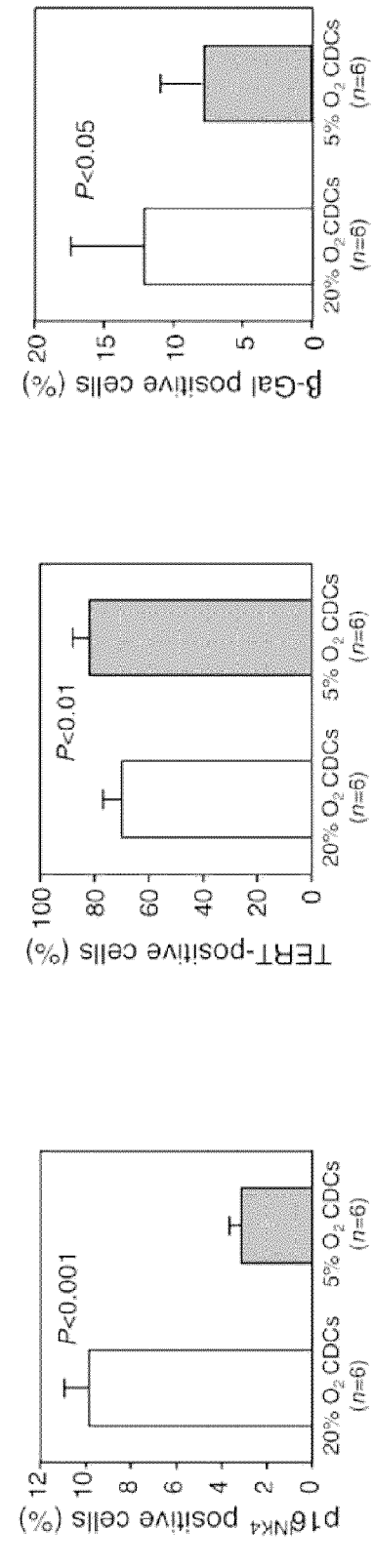
FIG. 20A  FIG. 20B  FIG. 20C  FIG. 20D  FIG. 20E  FIG. 20F

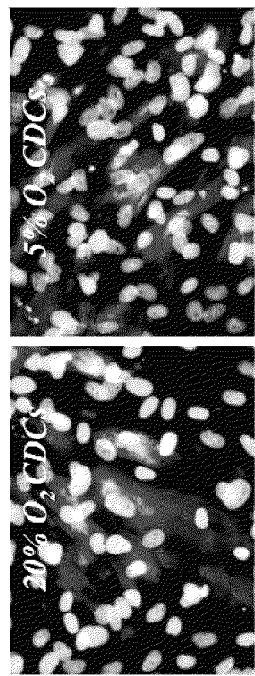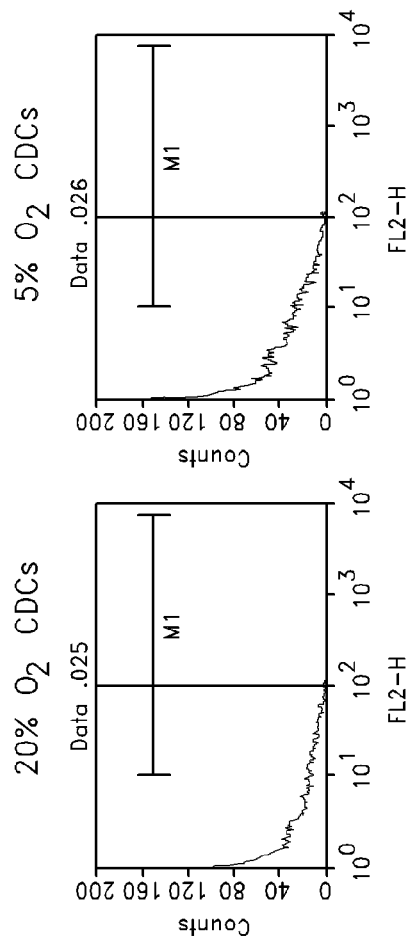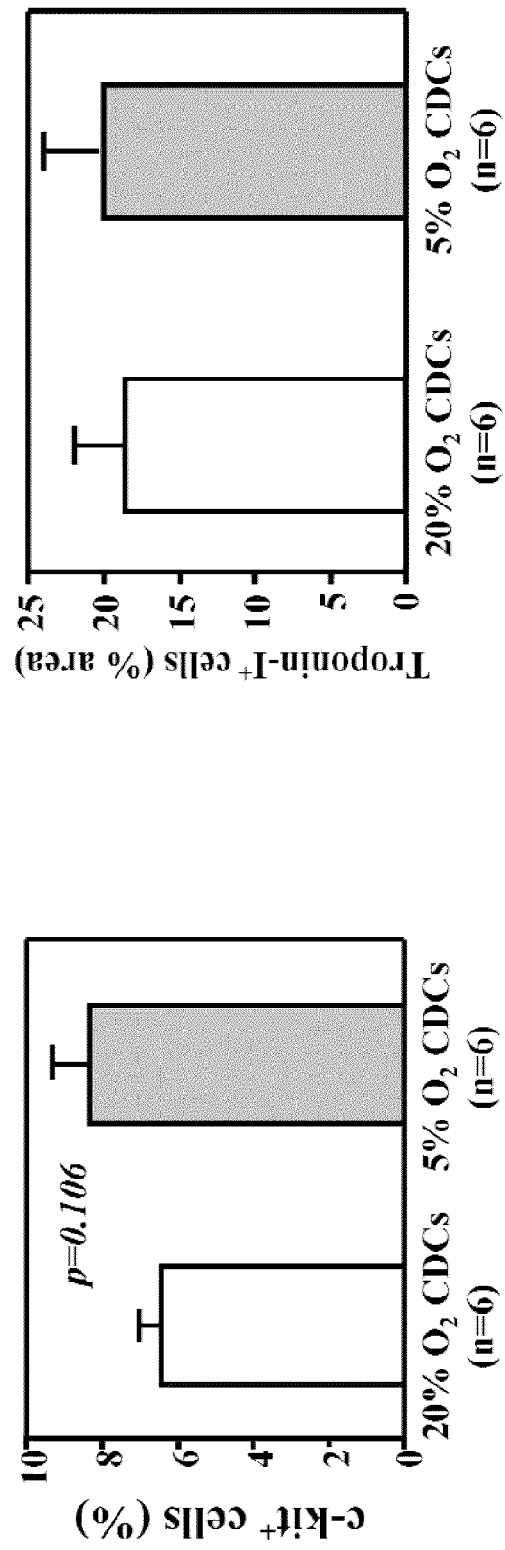
FIG. 25A  FIG. 25B  FIG. 25C  FIG. 25D

METHODS AND COMPOSITIONS FOR MAINTAINING GENOMIC STABILITY IN CULTURED STEM CELLS

RELATED CASES

This application claims the benefit of U.S. Provisional Application No. 61/330,251 filed on Apr. 30, 2010, the contents of which are expressly incorporated by reference herein.

STATEMENT REGARDING GOVERNMENT SPONSORED GRANT

This invention was made with Government support under the Research Project Grant (R01HL083109) by the National Institutes of Health. The United States Government has certain rights in this invention.

BACKGROUND

1. Field of the Invention

The present application relates generally to methods and compositions for generating genomically stable stem cells for the repair or regeneration of damaged cells or tissue. For example, in several embodiments the methods and compositions disclosed herein may be used for the repair and/or regeneration of cardiac tissue. In particular, isolated cardiac cells are cultured in oxygen concentrations and/or in the presence of antioxidant compositions that maintain an optimal balance between reduced oxidative-stress induced DNA damage and functional DNA repair systems, thereby reducing genomic instability (e.g., DNA damage or karyotypic abnormalities) in the cultured cells.

2. Description of the Related Art

The scope of human disease that involves loss of or damage to cells is vast and includes, but is not limited to neurodegenerative disease, endocrine diseases, cancers, and cardiovascular disease. For example, coronary heart disease is presently the leading cause of death in the United States, taking more than 650,000 lives annually. According to the American Heart Association, 1.2 million people suffer from a heart attack (or myocardial infarction, MI) every year in America. Of those who survive a first MI, many (25% of men and 38% of women survivors) will still die within one year of the MI. Currently, 16 million Americans are MI survivors or suffer from angina (chest pain due to coronary heart disease). Coronary heart disease can deteriorate into heart failure for many patients. 5 million Americans are currently suffering from heart failure, with 550,000 new diagnoses each year. Regardless of the etiology of their conditions, many of those suffering from coronary heart disease or heart failure have suffered permanent heart tissue damage, which often leads to a reduced quality of life.

SUMMARY

Cell therapy, the introduction of new cells into a tissue in order to treat a disease, represents a possible method for repairing or replacing diseased tissue with healthy tissue. However, cells generated for cell therapies have the potential to develop genomic abnormalities when being processed for regenerative therapies. Such abnormalities could lead to reduced efficacy of the cell therapy or to neoplastic development at the target tissue. Accordingly, it is highly desirable to provide methods and compositions for generating cells for cellular therapy that have enhanced genomic stability.

In several embodiments, there is provided a method for reducing the incidence of karyotypic abnormalities in cardiac stem cells for use in the repair or regeneration of cardiac tissue, comprising isolating cardiac stem cells and culturing the isolated stem cells in a culture media supplemented with an antioxidant composition. In several embodiments, the cells are isolated from healthy mammalian non-embryonic cardiac tissue, and then cultured.

In several embodiments there is provided a composition for reducing the incidence of karyotypic abnormalities in cultured cardiac stem cells, the composition comprising at least one peptide antioxidant, at least one non-peptide antioxidant; and a culture media suitable for culturing cardiac stem cells, wherein the culture media is supplemented with the at least one peptide antioxidant and the at least one non-peptide antioxidant.

In several embodiments, there is provided a composition for reducing the incidence of karyotypic abnormalities in cultured cells, the composition comprising a culture media suitable for culturing cells, and at least one antioxidant.

In several embodiments the at least one antioxidant is present in a concentration ranging from about 0.1 to 200 µM, and functions to reduce reactive oxygen species (ROS) to a level which decreases oxidative-stress induced DNA damage in the cultured cells. In several embodiments, the antioxidant composition comprises at least one peptide antioxidant and at least one non-peptide antioxidant. Although the concentrations of the peptide antioxidant(s) and non-peptide antioxidant(s) may vary according to the embodiment (e.g., based on the cell type, the age of the source tissue, or other factors), in several embodiments the at least one peptide antioxidant and the at least one non-peptide antioxidant are present in an individual or combined concentration ranging from about 0.1 to 200 µM. In several embodiments, the antioxidant composition is suitable for reducing formation of ROS such as peroxides and free radicals, among others. In some embodiments, the reduced formation of ROS results in a level of ROS which decreases oxidative-stress induced DNA damage, yet the resulting ROS levels are not so low that markers of DNA repair mechanisms are significantly reduced, and further the reduction does not significantly induce markers of DNA damage in the cardiac stem cells. Thus, in several embodiments, the balance of reduced ROS generation, non-reduced DNA repair mechanisms and non-induction of DNA damage reduces the overall incidence of karyotypic abnormalities in the cardiac stem cells. In several embodiments, this is particularly advantageous, as karyotypic abnormalities reduce the percentage of usable cells in a pool of cells to be used in cell therapy, but also present the risk of unwanted neoplastic growth (teratoma formation). Thus, in several embodiments the methods and compositions disclosed herein yield a greater number of cells suitable for cell therapy (either in total number or based on a percent of useable cells) and yield cells that are safer for use in cell therapies. In several embodiments the markers of DNA repair mechanisms comprise one or more DNA repair enzymes selected from the group consisting of: ATM, ATR, Rad50, Rad51, Chk1, and Chk2 and in several embodiments the markers of DNA damage comprise one or more of γ-H2AX foci in cultured cells, γ-H2AX mRNA, or γ-H2AX protein. Other markers of DNA repair or DNA damage are evaluated in other embodiments (e.g., phosphorylation of H2AX, 7-hydro-8-oxo-2'-deoxyguanosine concentrations). As a result of culturing cells in the culture conditions and compositions provided in several embodiments, ROS levels are reduced by at least 10%. In other embodiments, greater reductions in ROS are achieved (e.g., at least 15%, at least 20%, or more). In still additional embodiments, a balance between reduced ROS generation, non-reduced DNA repair mechanisms and non-induction of DNA damaged is not required to realize reductions in karyotypic abnormalities. For example, in some embodiments, alterations of one or more of the above-referenced characteristics is sufficient to yield a reduction in karyotypic abnormalities.

In several embodiments, the at least one peptide antioxidant is present in a concentration ranging from about 0.1 to 200 µM. In several embodiments, the at least one peptide antioxidant comprises glutathione. In some embodiments, glutathione can be supplemented by including glutathione precursors in the culture media (for example n-acetylcysteine, s-adenosylmethionine or whey protein). As such, the cultured cells not only have the glutathione in the media available, but have precursor compounds present to increase the amount of glutathione production in response to changing culture conditions.

Similarly, in several embodiments the at least one non-peptide antioxidant is present in a concentration ranging from about 0.1 to 200 µM. In several embodiments the at least one non-peptide antioxidant is selected from the group consisting of thiols, vitamins and polyphenols. In some embodiments, these non-peptide antioxidants function to terminate chain oxidation reactions which are responsible, at least in part, for generation of free radicals. In some embodiments, these antioxidants "sacrifice" themselves by being oxidized, thereby sparing the genetic material of the cell from damage. In several embodiments vitamins are used as the non-peptide antioxidant, and may comprise one or more vitamins selected from the group consisting of: vitamin A, vitamin E, and vitamin C. In several embodiments the various vitamins are present in an individual or total concentration ranging from about 1 to 150 µM. In still additional embodiments, other antioxidants may be used to supplement culture media. For example, enzymes such as catalase, superoxide dismutase and various peroxidases are used in some embodiments.

Other concentrations are used in some embodiments, depending on the cell type, the age of the cells, the time the cells have been in culture, the passage number of the cell population. The various components of the antioxidant composition may, in some embodiments, be balanced to advantageously tailor the composition to a particular set of characteristics possessed by a particular cell population. For example, in some embodiments, an high passage cell population may benefit from a greater concentration of a peptide antioxidant as compared to a non-peptide antioxidant (or vice versa).

In several embodiments, cells are cultured with the antioxidant composition for about 24 hours. In some embodiments, shorter culture times are used (e.g., about 4-6 hours, about 5-10 hours, about 8-16 hours, about 16 to 20 hours, and overlapping ranges thereof). In some embodiments, longer culture times are used (e.g., about 24-36 hours, about 36-48 hours, about 48-72 hours, or longer). In some embodiments, time can be varied depending on a variety of factors. For example, the age of the source tissue may be a factor in determining how long a cell needs to be cultured for the antioxidant composition to be effective. The overall metabolic status of the cells may also be an important variable. Active cells may more effectively metabolize the antioxidant compositions, thereby benefiting from the antioxidant effects described herein. However, in some cases, too great a metabolic rate may overwhelm the antioxidant composition, thereby requiring additional time in culture, increased concentrations of the compositions disclosed herein, or combinations of both.

In one embodiment, cardiac cells are cultured with an antioxidant composition comprising the peptide antioxidant glutathione in a concentration ranging from about 0.1 to 20 µM, and a combination of non-peptide antioxidants comprising vitamin C and vitamin E, in a concentration ranging from about 0.1 to 20 µM. In some embodiments, antioxidant compositions are used in conjunction with other methods to reduce the incidence of karyotypic abnormalities in cells. For example, in some embodiments, cells are cultured in an environment that more closely mimics the natural in vivo conditions for that cell (e.g., physiologic oxygen concentrations), in conjunction with the use of antioxidant compositions.

In several embodiments, there is provided a method of increasing the yield of stem cells in culture, comprising obtaining a population of stem cells isolated from a source of tissue, restricting oxygen concentrations in a culture environment to physiologic oxygen concentrations, and culturing the stem cells in the restricted oxygen culture environment. In several embodiments, physiologic levels of oxygen increase the rate at which the stem cells proliferate, thereby increasing the yield of stem cells as compared to culture conditions that employ non-physiologic levels of oxygen. In several embodiments, the yield of stem cells is increased per unit weight of the source tissue as compared to the yield of stem cells cultured in conditions that employ non-physiologic concentrations of oxygen. In some embodiments, the per unit weight yield is increased by at least about 5% for a given time period of culturing. In some embodiments, the per unit weight yield is increased by at least about 20% for a given time period of culturing. In several embodiments, greater increases in per unit weight yield are achieved (e.g., at least 25%, 30%, 35%, 40%, 50%, or greater). In several embodiments the source tissue is cardiac tissue and the stem cells are cardiac stem cells.

Advantageously, in several embodiments, the increased yield reduces the amount the amount of time that the stem cells are cultured in order to reach a certain population as compared to the amount of time stem cells are cultured in non-physiologic concentrations of oxygen in order to reach the certain population. For example, in some embodiments, the increased yield reduces the amount the amount of time required for culturing by 20%. In additional embodiments, the increased yield reduces the amount the amount of time required for culturing by 50%. Such increased yield (and reduced culture time) are particularly advantageous in some embodiments, wherein the cells are to be used for therapy (reduced time from collection to therapy), or in generating a cell bank (reduced time to generate a sizeable bank for future therapy). Moreover, in either in autologous or allogeneic transplant scenarios, the reduced time to generate a given population size reduces the time between tissue collection and subsequent therapy. In some allogeneic contexts, this time is negligible, because a cell bank can be generated prior to the need for any other subject to receive therapy.

In several embodiments, there is provided a method for increasing the function of the cardiac tissue of a subject having damaged or diseased cardiac tissue, comprising obtaining a population of cardiac stem cells for administration to the subject, wherein the cardiac stem cells are harvested from donor cardiac tissue and expanded in a culture environment comprising oxygen concentrations restricted to physiologic oxygen concentrations (to generate an expanded population of cardiac stem cells), and administering at least a portion of the expanded population of cardiac stem cells to the subject. In several embodiments the administered cardiac stem cells engraft into the cardiac tissue of the subject to a greater degree than cardiac stem cells expanded in non-physiologic concentrations of oxygen. In several embodiments the administered cardiac stem cells survive in the cardiac tissue of the subject to a greater degree than cardiac stem cells expanded in non-physiologic concentrations of oxygen. In still additional embodiments, the greater degree of engraftment and/or survival lead to increased cardiac function in the subject.

In several embodiments, there is provided a method for enhancing the efficacy of cardiac stem cell therapy, comprising obtaining a population of cardiac stem cells for administration to a subject in need of cardiac stem cell therapy due to damaged or diseased cardiac tissue wherein the cardiac stem cells are harvested from donor cardiac tissue and expanded in a culture environment comprising oxygen concentrations restricted to physiological oxygen concentrations to generate an expanded population of cardiac stem cells, and administering at least a portion of the expanded population of cardiac stem cells to the subject.

In several embodiments the physiologic oxygen concentrations are between about 1% to about 8%, about 2% to about 7% about 3% to about 6%, about 4% to about 5%, and overlapping ranges thereof. In one embodiment, the oxygen concentration ranges from about 4% to about 7%. In several embodiments, the oxygen concentrations are tailored to a particular cell type. For example, depending on the region of tissue from which a population of cells originated (e.g., a tissue having low oxygen concentrations in vivo versus a tissue having high oxygen concentrations in vivo) oxygen concentrations can be adjusted to be appropriately physiologic for that cell type. Even within a particular organ, the degree of oxygenation may vary. Tissue oxygen concentrations are readily discerned by one of ordinary skill in the art and can thus be used to tailor the methods disclosed herein to generate greater numbers of cells, more genetically stable cells, and/or cells with increased functionality.

In several embodiments, the methods provided comprise culturing cells in physiologic oxygen concentrations to reduce the incidence of karyotypic abnormalities in the cultured as compared to cells cultured in non-physiologic concentrations of oxygen. In some such embodiments, culturing in physiologic oxygen concentrations reduces the incidence of aneuploidy in the cultured cells as compared to cells cultured in non-physiologic concentrations of oxygen. In some embodiments, DNA strand breaks are reduced. In some embodiments, combinations of reduction in karyotypic abnormalities, aneuploidy, and DNA strand breaks are reduced. In several embodiments the cultured cells are cardiac stem cells. In some embodiments, the cells are for use in allogeneic cardiac cell therapy. In other embodiments, the cells are for use in autologous therapy. In several embodiments, the cardiac stem cells comprise cardiospheres, cardiosphere derived cells, or a subsequent generation of cardiospheres. In some embodiments, the cardiac stem cells are suitable for administration of a subject having damaged or diseased cardiac tissue.

In several embodiments, the administration of the cardiac stem cells cultured in physiologic oxygen to a subject results in increased engraftment into the cardiac tissue of the subject as compared to engraftment of cardiac stem cells cultured in non-physiologic concentrations of oxygen. In several embodiments, the administration of the cardiac stem cells cultured in physiologic oxygen to a subject results in one or more of increased myocardial viability, increased wall thickness, and lower left ventricular volume in the cardiac tissue of the subject as compared to that resulting from administration of cardiac stem cells cultured in non-physiologic concentrations of oxygen. In several embodiments, increased function due to administration of cells cultured in physiologic oxygen concentrations is realized as an improved left ventricular ejection fraction (by at least 5% as compared to increased function due to administration of cardiac stem cells expanded in non-physiologic concentrations of oxygen). In several embodiments, the administration of the cardiac stem cells cultured in physiologic oxygen to a subject results in greater survival of the cells in the cardiac tissue of the subject to a greater degree than cardiac stem cells expanded in non-physiologic concentrations of oxygen In several embodiments, a method for reducing the incidence of karyotypic abnormalities in cardiac stem cells for use in the repair or regeneration of cardiac tissue is provided. In one embodiment, the method comprises isolating cardiac stem cells and culturing the isolated stem cells in a culture media supplemented with an antioxidant composition. In one embodiment, the method comprises combining cells susceptible to chromosomal damage with an antioxidant composition at a concentration suitable to reduce the incidence of chromosomal damage in the cells, when, for example, the cells are administered to a mammal. In one embodiment, the antioxidant composition is provided at a concentration that reduces free radical damage while still permitting (or without substantially impairing) the function of one or more of the cell's endogenous repair mechanisms.

In several embodiments, a composition for reducing the incidence of karyotypic abnormalities in cultured cardiac stem cells is provided. In one embodiment, the composition comprises at least one peptide antioxidant, at least one non-peptide antioxidant, and a culture media suitable for culturing cardiac stem cells that is supplemented (or suitable to supplementation) with the at least one peptide antioxidant and the at least one non-peptide antioxidant. In one embodiment, the antioxidant composition comprises, consists or consists essentially of one or more non-peptide antioxidants. In another embodiment, the antioxidant composition comprises, consists or consists essentially of one or more peptide antioxidants.

In several embodiments, a composition for reducing the incidence of karyotypic abnormalities in cultured cells is provided. In one embodiment, the composition comprises a culture media suitable for culturing cells and at least one antioxidant present in a concentration ranging from about 0.1 to 200 µM. In some embodiments, the cells are stem cells. In some embodiments, the cells are cardiac stem cells.

In several embodiments, a method for reducing cellular and/or genetic (e.g., karyotypic) abnormalities in cells cultured in a medium is provided. In one embodiment, the method comprises contacting the cells with one or more of the compositions disclosed herein. In another embodiment, the method comprises culturing the cells in a hypoxic environment and, optionally, with an antioxidant composition according to several embodiments disclosed herein.

In several embodiments, the cells are isolated from healthy mammalian non-embryonic cardiac tissue. In some embodiments, the cells are isolated from healthy mammalian non-embryonic non-cardiac tissue. In some embodiments, the cells are isolated from embryonic tissue.

In several embodiments, the antioxidant composition reduces reactive oxygen species to a level which decreases oxidative-stress induced DNA damage, but does not significantly impair DNA (and/or other cellular) repair mechanisms. In one embodiment, antioxidant compositions according to several embodiments disclosed herein reduce oxidative-stress induced damage without adversely affecting the cell's own repair mechanisms by more than 1%, 5%, 10%, 25%, or 50%.

In several embodiments, the reduction in reactive oxygen species does not significantly induce DNA damage (as evidenced by markers of DNA damage) in stem cells, such as cardiac stem cells. In several embodiments, the balance of reduced reactive oxygen species, non-reduced DNA repair mechanisms and non-induction of DNA damage reduces the incidence of karyotypic abnormalities in cells, including stem cells (such as cardiac stem cells).

In some embodiments, at least one peptide antioxidant is selected from the group consisting of enzymes, proteins, peptides. In some embodiments, at least one peptide antioxidant comprises glutathione. In some embodiments, glutathione is present in a concentration ranging from about 1 to 150 µM. In some embodiments, glutathione is present in a concentration ranging from about 1 to 50 µM. In some embodiments, glutathione is present in a concentration ranging from about 0.1 to 20 µM.

In some embodiments, at least one non-peptide antioxidant is selected from the group consisting of thiols, vitamins and polyphenols. In some embodiments, at least one non-peptide antioxidant comprises one or more vitamins. In some embodiments, the vitamins comprise one or more of vitamin A, vitamin E, and vitamin C. In some embodiments, the vitamins are present in an individual or total concentration ranging from about 1 to 150 µM. In some embodiments, the vitamins are present in an individual or total concentration ranging from about 1 to 50 µM. In some embodiments, the vitamins comprise vitamin C and vitamin E. In some embodiments, vitamin C and vitamin E are present in an individual or total concentration ranging from about 1 to 50 µM. In some embodiments, vitamin C and vitamin E are present in a concentration ranging from about 0.1 to 20 µM.

In some embodiments, the antioxidant composition comprises, consists of, or consists essentially of glutathione at a concentration ranging from about 0.1 to 20 µM and vitamin C and vitamin E, which are each present in a concentration ranging from about 0.1 to 20 µM.

In several embodiments, cells are exposed to antioxidant compositions and/or hypoxic conditions to cause a reduction in reactive oxygen species of at least 10% as compared to cells cultured in 20% oxygen. In some embodiments, the reactive oxygen species are reduced by at least 50% as compared to cells cultured in 20% oxygen. In some embodiments, the reactive oxygen species are reduced by about 60%-70% (e.g., 65%) as compared to cells cultured in 20% oxygen. In some embodiments, a reduction in reactive oxygen species of at least 10%, 25%, 50% or 75% is achieved as compared to cells cultured in hyperoxic conditions. In one embodiment, the use of antioxidant compositions disclosed herein reduces karyotypic damage when cells are cultured in about 20% oxygen, or higher. In one embodiment, the combined use of antioxidant compositions and hypoxic conditions result in a synergistic effect (e.g., enhanced reduction of cellular/DNA damage).

In several embodiments, the markers of DNA repair mechanisms comprise one or more DNA repair enzymes. In some embodiments, DNA repair enzymes are selected from the group consisting of ATM, ATR, Rad50, Rad51, Chk1, Chk2, or combinations thereof. In several embodiments of the invention, compositions or hypoxic conditions disclosed herein, do not impair DNA repair mechanism at by more than 0% (e.g., no effect), 2%, 5%, 10%, 20%, 30%, and 50%. DNA repair mechanisms include, but are not limited to, base excision, nucleotide excision and mismatch repair. In one embodiment, compositions or hypoxic conditions disclosed herein maintain or up-regulate at least one repair mechanism while down-regulating another repair mechanism, wherein the overall impairment of DNA repair is no more than 0%, 2%, 5%, 10%, 20%, 30%, or 50%. In one embodiment, compositions or hypoxic conditions disclosed herein do not impair base excision, nucleotide excision or mismatch repair. In another embodiment, compositions or hypoxic conditions disclosed herein do not impair at least two of base excision, nucleotide excision or mismatch repair. In one embodiment, compositions or hypoxic conditions disclosed herein reduce the incidence of karyotypic abnormalities in cells by more than 10%, 25%, 50%, 75%, or 95% as compared to control cells.

In several embodiments, the markers of DNA damage comprise one or more markers of DNA double-strand breaks. In some embodiments, the markers of DNA double-strand breaks comprise $\gamma$-$H_2AX$ foci in cultured cells, $\gamma$-$H_2AX$ mRNA, or $\gamma$-$H_2AX$ protein, or combinations thereof.

In several embodiments provided herein, the isolated cells (e.g., stem cells) are cultured for at least about 24 hours, 3 days or 7 days. In some embodiments, the isolated cells (e.g., stem cells) are cultured for a period of one to 6 months (e.g., 1, 2, 3, 4, 5, or 6 months).

In several embodiments, a method for assessing the risk of neoplastic disease in a subject is provided. In one embodiment, the method comprises obtaining a blood or tissue sample from the subject and measuring the concentration of one or more reactive oxygen species in the sample. In some embodiments, the risk for neoplastic disease is greater if the level of reactive oxygen species is sufficiently high to induce oxidative DNA damage in the cells of the subject and/or if the level of reactive oxygen species is sufficiently low to promote down-regulation of DNA repair mechanisms in the cells of the subject. Reduction in the risk of neoplastic disease is achieved in several embodiments of the invention by, for example, treating subjects with cells cultured in compositions or conditions disclosed herein.

In several embodiments, a method for assessing the risk of neoplastic disease in a subject is provided. In one embodiment, the method comprises analyzing the subject's tissue for evidence of karyotypic abnormalities (e.g., DNA damage) and correlating the damage with the subject's antioxidant levels. Optionally, the subject is then treated to reduce or increase antioxidant levels as needed. In one embodiment, evidence of damage is determined by analyzing markers of DNA damage, DNA damage-associated mRNA expression levels, and/or DNA damage-associated protein expression levels. In one embodiment, the risk for neoplastic disease increases as the incidence of DNA damage increases, as the expression of DNA damage-associated mRNA increases, and/or as the expression of DNA damage-associated protein increases. In some embodiments, DNA damage is measured by identifying $\gamma$-$H_2AX$ foci, by measuring $\gamma$-$H_2AX$ mRNA expression levels, and/or by measuring $\gamma$-$H_2AX$ protein expression levels.

In several embodiments, a method for optimizing the amount of an antioxidant-containing supplement administered to a subject is provided. In one embodiment, the method comprises measuring the concentration of one or more reactive oxygen species in the subject's sample (e.g., tissue samples, skin scrapings, blood, isolated cells, saliva, urine, other bodily fluids, etc.) and the incidence of DNA damage in cells isolated from the sample. In some embodiments, in addition to, or instead of, ascertaining DNA damage, the expression of DNA repair enzymes in cells isolated from the sample is measured. In one embodiment, the method further comprises treating the patient with an antioxidant composition, and optionally adjusting the composition to balance the concentration of reactive oxygen species in the subject with the subject's endogenous DNA repair mechanism(s), as determined by, for example, expression of DNA repair enzymes or other markers of DNA repair. In several embodiments, compositions (e.g., supplements) comprising an optimal amount of antioxidant(s) are provided that are formulated to decrease oxidative-stress induced DNA damage without negatively impacting (wholly or partially) DNA repair mechanisms in the subject. In one embodiment, therapeutic antioxidant compositions that balance oxidative damage with endogenous DNA repair mechanisms are provided based on a subject's individual antioxidant and/or karyotypic profile. In some embodiments, the invention comprises determining γ-$H_2$AX foci to gauge risk of chromosomal damage (and neoplasm) and/or to optimize antioxidant supplements.

BRIEF DESCRIPTION OF THE FIGURES

FIGS. 3A, 3B, and 3C depict representative microscopic images of CDCs cultured for 36 days in various conditions (A=20% $O_2$; B=20% $O_2$ plus antioxidant supplement at 1:1000 dilution; C=20% $O_2$ plus custom antioxidant cocktail at 100 μM). FIG. 3D depicts that no significant differences in CDC proliferation were detected among the various culture conditions.

FIG. 4A depicts intracellular ATP concentrations and FIG. 4B depicts mitochondrial membrane potential of CDCs cultured in various conditions.

FIG. 7A depicts intracellular ROS concentration in human cardio sphere-derived cells after long-term culture under 20% $O_2$, 20% $O_2$, or under 20% $O_2$ with added antioxidants. FIG. 7B depicts intracellular ROS concentrations after culturing in hypoxic conditions or with the addition of antioxidants. FIG. 7C depicts γ-$H_2$AX foci in CDCs cultured in the indicated conditions. FIG. 7D depicts quantitation of γ-$H_2$AX foci.

FIG. 13A depicts protein expression and quantitation of ATM from human cardiosphere-derived cells after 1-2 months long-term culture under the indicated conditions. FIG. 13B depicts protein expression of various DNA repair-related factors in human cardiosphere-derived cells after 1-2 months long-term culture under different conditions.

FIGS. 20A-20F depict analysis of cell senescence. Compared with 20% $O_2$ culture, cell senescence of CDCs was improved under 5% $O_2$ culture, by flow cytometry for p16$^{INK4A}$ (panels A and D), immunostaining for telomerase activity (panels B and E), and senescence-associated b-galactosidase staining (panels C and F).

FIGS. 25A-25D depict cell phenotype and in vitro myogenic differentiation. Panel A shows flow cytometry data shows no significant difference in the proportion of c-kit$^+$ stem cells in cardiac-derived cells expanded in 5% $O_2$ versus 20% $O_2$ (quantification in panel C). Panel B shows similar expression of troponin T was also observed in the two groups (quantification in panel D).

DETAILED DESCRIPTION

Figure 1:
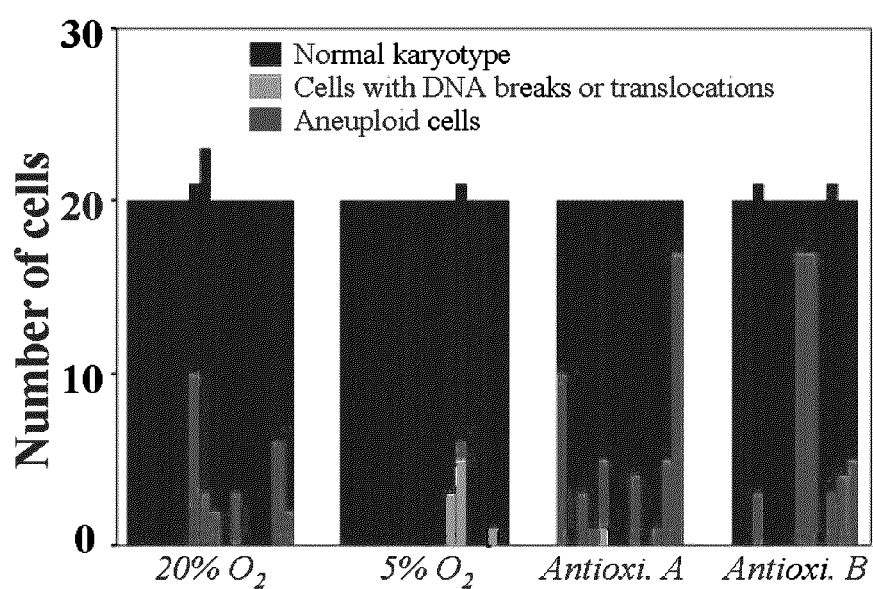
FIG. 1 depicts histograms summarizing karyotyping data for the various culture conditions utilized in the Examples.

In several embodiments described herein, methods of reducing the incidence of karyotypic abnormalities in cultured stem cells for use in the repair or regeneration of cardiac tissue are provided. In several embodiments, compositions that reduce the incidence of karyotypic abnormalities in the culturing of stem cells are provided. Such embodiments are advantageous because chromosomal abnormalities have been found in an unexpectedly large percentage of stem cells isolated, cultured, and expanded for use in cellular therapies. For example, chromosomal abnormalities have been found in up to 50% of long-term cultured human embryonic stem (ES) cells. Normal embryonic stem cells, which are typically derived from an early stage embryo, have the potential to develop into any type of cell in the body. In some instances, unplanned growth of one cell type in a distinct type of tissue may result in the formation of teratomas. Undesirable neoplastic growth may be potentiated if ES cells with chromosomal abnormalities are used in therapy.

In contrast to ES cells, adult stem cells generally develop into cell types related to the tissue from which the stem cells were isolated. However, the potential for undesirable neoplastic growth still exists, particularly if adult stem cells with chromosomal abnormalities are used in therapy. In fact, G-banding karyotype analysis of primary cardiosphere-derived cells (CDCs, a heart-derived mixed-cell population rich in cardiac stem cells) revealed that ~30% of preliminary CDC production runs resulted in cells with chromosomal abnormalities (See Table 1). In addition to potential neoplastic growth, genomic alterations of stem cells may impair therapeutic potency of administered cells. Thus, several embodiments of the present invention are particularly beneficial because they enhance the therapeutic potency (e.g., efficacy and/or viability, etc.) of the administered cells.

TABLE 1

Summary of Chromosomal Abnormalities

| Samples | Karyotype |
| --- | --- |
| 2424/p3 | 46, XX[20] |
| 2377/p3 | 46, XX[20] |
| 2404/p3 | 46, XY[20] |
| 2482/p4 | 46, XY[20] |
| R071215/p3 | 47, XY +8[3]/47, XY +18[3]/46, XY [44] |
| R071215/p6 | 47, XY +8[2]/46, XY[48] |
| R071212/p6 | 46, XY[50] |
| R071214/p4 | 47, XY +2[4]/46, XY[46] |
| R071214/p5 | 47, XY +2[6]/46, XY[44] |
| R071214/p6 | 47, XY +2[13]/46, XY[7] |
| 6-1-1/p5 | 46, XY[20] |
| 6-1-3/p5 | 46, XY[20] |
| 10-1/p2 | 46, XX[20] |
| CSB9/p4 | 46, XY, inv(9)(p11; q13) [20] |
| CSB11/p3 | 46, XY[20] |
| CSB3/p3 | 45, X − Y[6]/46, XY[14] |
| BX13/p4 | 46, XY[20] |
| BX14/p3 | 46, XX[20] |
| BX15/p3 | 47, XY +8[20] |
| BX16/p4 | 45, X − Y[7]/47, XY +i(8)(q10)[6]/47, XY +8[1]/46, XY[6] |
| BX17/p2 | 45, X − Y[3]/46, XY[17] |
| BX18/p3 | 46, XY[20] |
| BX19/p3 | 46, XY[20] |
| BX20/p2 | 46, XY[20] |
| BX21/p2 | 46, XY[20] |
| BX22/p1 | 46, XY[20] |
| BX23/p1 | 46, XY[20] |
| BX23/p2 | 46, XY[20] |
| BX24/p1 | 45, X − Y[10]/47, XY +18[2]/46, XY[8] |
| BX27/p1 | 47, XY +8[6]/45, X − Y[3]/47, XY +Y[2]/46, XY[9] |
| BX27/p2 | 47, XY +8[14]/46, XY[6] |
| BX43/p0 | 46, XY[20] |
| BX45/p0 | 46, XY[20] |
| BX46/p0 | 46, XY[20] |
| BXJ4/p0 | 45, −Y, t(X; 11)(p10; p10)[11]/45, X, −Y[3]/46, XY[6] |
| BX45/p1 | 46, XY[20] |

TABLE 1-continued

Summary of Chromosomal Abnormalities

| Samples | Karyotype |
|---|---|
| BX46/p1 | 47, XY +8[4]/46, XY [16] |
| BXJ4/p1 | 45, –Y, t(X; 11)(p10; p10)[19]/46, XY [1] |
| BX34/p1 | 46, XY[20] |
| BX40/p2 | 46, XY[20] |
| BXJ2/p1 | 46, XX[20] |

Reactive oxygen species (ROS) are reactive molecules that contain the oxygen atom. The superoxide ion ($O_2$—) and peroxides (e.g., hydrogen peroxide, $H_2O_2$) are well known ROS. The superoxide ion leaks from active mitochondria and is converted to $H_2O_2$. Cellular enzymes such as catalase and superoxide dismutase act on $H_2O_2$ to form hydrogen and water; however these reactions are not efficient enough to remove all the $H_2O_2$. ROS molecules are typically highly reactive due to the presence of unpaired valence shell electrons. While ROS are formed under normal circumstances where oxygen is metabolized, and may play important roles in cell signaling, during times of environmental or metabolic stress (e.g., UV or heat exposure, ionizing radiation, hypoxia, ischemia, etc.) ROS levels may increase, possibly resulting in damage to intracellular structures or induction of programmed cell death mechanisms. The various pathways that generate ROS are known as oxidative stress. Increases in oxidative stress have the potential to damage RNA, DNA, or protein that, if uncorrected, may lead to chromosomal abnormalities. Chromosomal abnormalities, in turn, can lead to poorly functioning or malfunctioning cells, uncontrolled proliferation of cells, or apoptosis, among other outcomes.

Because cells will fail to function or function improperly if oxidative stress corrupts the integrity or accessibility of a cells genome, mammalian cells have developed a variety of innate DNA repair mechanisms. In some instances, cells will use the unmodified complementary DNA strand to recover any genetic information that is lost due to oxidative stress. If both strands of DNA are damaged, the cell may allow polymerases to replicate DNA through the site of the lesion in order to replicate essential DNA sequences. However, none of these repair mechanisms is completely free of errors. Thus, the proper function and longevity of a cell is a balance of the oxidative stress a cell experiences and the ability of one or more DNA repair mechanism to maintain the cell's genome in normal working order.

Often, cells to be used in research or clinical applications are cultured in media equilibrated with 95% air and 5% $CO_2$ (~20% $O_2$). Certain cells thrive in such an environment, as the oxygen concentration mimics what those cells would be exposed to in vivo. However, in the case of many stem cell varieties, depending on the tissue, cellular oxygen concentrations may be as low as ~1-5% in the in vivo physiological microenvironment. Exposure of stem cells to a non-physiological hyperoxic state in culture may lead to oxidative stress, which, as discussed above, may induce ROS formation, DNA damage, and/or genomic instability. Genomic instability may be manifest in several ways, including karyotypic abnormalities, low viability cells, cells prone to neoplastic formation and the like. As used herein, the terms "physiologic oxygen concentrations" and "physiological oxygen concentrations" shall be given its ordinary meaning and shall also refer to oxygen concentrations ranging from about 1% to about 8% oxygen. In some embodiments oxygen concentrations in which the CDCs (or other cardiac stem cells) are cultured range from about 1% to about 2%, about 2% to about 3%, about 3% to about 4%, about 4% to about 5%, about 5% to about 6%, about 6% to about 7%, and overlapping ranges thereof. In several embodiments physiologic oxygen conditions are maintained throughout the entire culture process, while in other embodiments, physiologic oxygen conditions are used in only a portion of the culture process.

Therefore, in several embodiments, methods and compositions for reducing the incidence of karyotypic abnormalities in cultured stem cells for use in the repair or regeneration of tissue are provided. In several embodiments, use of the compositions and methods disclosed herein permit the use of hyperoxic cell culture conditions. In several embodiments, cardiac tissue is repaired or regenerated. Other types of tissue (e.g., kidney, lung, liver pancreas, spleen, bone, bone marrow, muscle tissue, vascular tissue, nervous tissue, skin, etc.) are repaired or regenerated in other embodiments. In several embodiments the method comprises providing a culture media supplemented with an antioxidant cocktail (discussed in more detail below) that is capable of inducing a balance between the formation of ROS and the ensuing DNA damage and the innate DNA repair mechanisms of the cultured cells, thereby reducing in the incidence of karyotypic abnormalities. In some embodiments, the method optionally includes culturing the cells in a "hypoxic" environment relative to standard 20% $O_2$ cell culture conditions (e.g., oxygen concentrations ranging from about 1% to about 8%). In several embodiments, such culture conditions improve the viability of the cultured stem cells. In some embodiments, short term viability is improved, while in some embodiments, long-term viability is improved. In some embodiments, both short and long-term viability is improved. As such, in several embodiments, the proliferation rate of the cells in culture is increased. However, due to the normoxic (vis-à-vis the normal cellular environment) conditions, limited genetic alterations occur. In some embodiments, this is particularly advantageous because the rate of cell expansions reduces the amount of time needed to reach a certain population of cells. In some embodiments, wherein the cells are to be administered for therapy in a certain dosage, the amount of time between inception of culture of the cells and administration of a certain dose of cells is reduced (e.g., the time to reach a certain population is reduced as compared to culture methods employing non-physiologic concentrations of oxygen.

In several embodiments, culturing stem cells in physiologic oxygen concentrations (and/or in antioxidant compositions) positively affects the cells even after the period of culturing is complete (e.g., the cells have been administered to a subject). For example, in some embodiments, the use of physiologic oxygen concentrations imparts to stem cells a greater viability in vivo. As such, cells cultured according to the methods and/or with the use of compositions as disclosed herein, remain viable for a longer period of time post-administration, thereby increasing the potential effectiveness of these cells in cellular therapies. In several embodiments, cells cultured according to the methods and/or with the use of compositions as disclosed herein engraft into host tissue to a greater degree than those cultured in non-physiologic concentrations of oxygen. In certain embodiments, engraftment is a threshold step to efficacious cell therapy. For example, in some therapies, direct tissue regeneration plays a significant role in the therapy. However, advantageously, in some embodiments, cells cultured according to the methods and/or with the use of compositions as disclosed herein generate a more effective amount of certain cellular signaling factors (e.g., autocrine, paracrine, intracrine or endocrine factors such as growth factors, hormones, cytokines and the like) that invoke an indirect mechanism of therapy. For example, in some embodiments, an indirect mechanism, such as recruitment of other endogenous cells is induced by a signaling factor. As such, in some embodiments, a greater efficacy of therapy is achieved by virtue of the production (or reduced production) of certain such factors. In some embodiments, these signaling factors act in concert with direct mechanisms to achieve an effective therapy, while in some embodiments, the signaling factors function alone. In several embodiments, these direct and/or indirect mechanisms yield a more effective therapy, either by improving anatomical aspects of the target tissue, functional aspects of the target tissue, or combinations thereof. For example, in the context of cardiac stem cell therapy, culture of cardiac stem cells in physiologic oxygen concentrations improves the viability and engraftment of administered cells, as discussed below. Moreover, these improved parameters, in the context of a cell therapy for treating an adverse cardiac event, also yield improved cardiac anatomy (e.g., reduced infarct size, lower left ventricular area) and improved function (increased left ventricular ejection fraction, increased cardiac output, etc.).

In some embodiments, the stem cells are embryonic stem cells. In some embodiments, the stem cells are adult stem cells. In some embodiments, the stem cells are hematopoietic stem cells, neuronal stem cells, mesenchymal stem cells, insulin producing stem cells, hepatocyte stem cells, or epithelial stem cells, or combinations thereof. In some embodiments, the stem cells comprise cardiac stem cells. In some such embodiments, the cardiac stem cells are cardiospheres or cardiosphere-derived cells (CDCs). In some embodiments, the stem cells are processed and prepared for administration to a subject in order to repair damaged tissue. In some embodiments, the subject has damaged cardiac tissue in need of repair. In some embodiments, the subject is a mammal. In some embodiments, the subject is human, while in some embodiments the subject is a non-human mammal or other organism. Damaged cardiac tissue in a subject may be caused by a variety of events, including, but not limited to myocardial infarction, ischemic cardiac tissue damage, congestive heart failure, aneurysm, atherosclerosis-induced events, cerebrovascular accident (stroke), and coronary artery disease.

In one embodiment of the invention, cardiospheres and CDCs are isolated as according to the following general protocol. Briefly, cardiac tissue samples are weighed, cut into small fragments and cleaned of gross connective tissue, and washed in a sterile solution, such as phosphate-buffered saline. In some embodiments, the tissue fragments are at least partially digested with protease enzymes such as collagenase, trypsin, and the like. In certain embodiments, the digested pieces are placed in primary culture as explants on sterile tissue culture dishes with a suitable culture media. The digested pieces of tissue range in size from about 0.1 mm to about 2.5 mm (e.g., about 0.1-0.5 mm, 0.5-1 mm, 1-2 mm, 2-2.5 mm, and overlapping ranges thereof). In several embodiments, the digested pieces of tissue range 0.25 mm to about 1.5 mm. Smaller or larger pieces of tissue can be used in other embodiments. The tissue culture dish and culture media are selected so that the tissue fragments adhere to the tissue culture plates. In some embodiments, the tissue culture plates are coated with fibronectin or other extracellular matrix (ECM) proteins, such as collagen, elastin, gelatin and laminin, for example. In other embodiments, the tissue culture plates are treated with plasma. In certain embodiments, the dishes are coated with fibronectin at a final concentration of from about 10 to about 50 μg/mL. In still other embodiments, the fibronectin dishes are coated with fibronectin at a final concentration of from about 20 to 40 μg/mL, with still other embodiments employing a final fibronectin concentration of about 25 μg/mL.

In certain embodiments, the base component of the complete explant medium comprises Iscove's Modified Dulbecco's Medium (IMDM). In some embodiments, the culture media is supplemented with fetal calf serum (FCS) or fetal bovine serum (FBS). In certain embodiments, the media is supplemented with serum ranging from 5 to 30% v/v. In other embodiments, the culture media is serum-free and is instead supplemented with specific growth factors or hydrolyzed plant extracts. In other embodiments, the media is further supplemented with antibiotics, essential amino acids, reducing agents, or combinations thereof. In one embodiment, the complete explant medium comprises IMDM supplemented with about 20% fetal bovine serum, about 50 μg/mL gentamicin, about 2 mM L-glutamine, and about 0.1 mM 2-mercaptoethanol. In some embodiments, the explant media is changed every 2-4 days while the explants culture.

The tissue explants are cultured until a layer of stromal-like cells arise from adherent explants. This phase of culturing is further identifiable by small, round, phase-bright cells that migrate over the stromal-cells. In certain embodiments, the explants are cultured until the stromal-like cells grow to confluence. At or before that stage, the phase-bright cells are harvested. In certain embodiments, phase-bright cells are harvested by manual methods, while in others, enzymatic digestion, for example trypsin, is used. The phase-bright cells may be termed cardiosphere-forming cells, and the two phrases are used interchangeably herein.

Cardiosphere-forming cells may then be seeded on sterile dishes and cultured in cardiosphere media. In certain embodiments, the dishes are coated with poly-D-lysine, or another suitable natural or synthetic molecule to deter cell attachment to the dish surface. In other embodiments, for example, laminin, fibronectin, poly-L-orinthine, or combinations thereof may be used.

In certain embodiments, the base component of the cardiosphere medium comprises Iscove's Modified Dulbecco's Medium (IMDM). In some embodiments, the culture media is supplemented with fetal calf serum (FCS) or fetal bovine serum (FBS). In certain embodiments, the media is supplemented with serum ranging from 5 to 30% v/v, including from about 5% to about 10%, about 10% to about 15%, about 15% to about 20%, about 20% to about 25%, about 25% to about 30%, and overlapping ranges thereof. In other embodiments, the culture media is serum-free and is instead supplemented with specific growth factors or hydrolyzed plant extracts. In certain other embodiments, the media is further supplemented with antibiotics, essential amino acids, reducing agents, or combinations thereof. In one embodiment the cardiosphere medium comprises IMDM supplemented with about 10% fetal bovine serum, about 50 μg/mL gentamicin, about 2 mM L-glutamine, and about 0.1 mM 2-mercaptoethanol.

According to one embodiment, cardiospheres will form spontaneously during the culturing of the cardiosphere forming cells. Cardiospheres are recognizable as spherical multicellular clusters in the culture medium. Cells that remain adherent to the poly-D-lysine-coated dishes are discarded. In certain embodiments, the cardiospheres are collected and used to seed a biomaterial or synthetic graft. In other embodiments, the cardiospheres are further cultured on coated cell culture flasks in cardiosphere-derived stem cell (CDC) medium.

In some embodiments used to culture cardiospheres into CDCs, the culturing flasks are fibronectin coated, though in other embodiments other cellular attachment promoting coatings are employed. The cultured cardiospheres attach to the surface of the flask and are expanded as a monolayer of CDCs. CDC medium comprises IMDM, and in certain embodiments is supplemented with fetal calf serum (FCS) or fetal bovine serum (FBS). In some embodiments, the media is supplemented with serum ranging from 5 to 30% v/v. In other embodiments, the culture media is serum-free and is instead supplemented with specific growth factors or hydrolyzed plant extracts. In certain other embodiments, the media is further supplemented with antibiotics, essential amino acids, reducing agents, or combinations thereof. In one embodiment, the CDC medium comprises IMDM supplemented with about 10% fetal bovine serum, about 2 mM L-glutamine, and about 0.1 mM 2-mercaptoethanol. CDCs may be repeatedly passaged by standard cell culture techniques and in several embodiments are harvested and used to seed a biomaterial or synthetic graft.

In some embodiments the cells to be administered to the subject are obtained from healthy tissue of the subject, e.g., an autologous transplant. In some embodiments the cells to be administered to the subject are obtained from healthy tissue of an individual other than the subject, e.g., an allogeneic transplant. In some embodiments the cells to be administered to the subject are obtained from healthy tissue an individual who is highly genetically similar or identical to the subject, e.g., a syngeneic transplant. In still further embodiments, the cells to be administered to the subject are obtained from healthy tissue an individual of a species distinct from the subject, e.g., a xenogeneic transplant.

In some embodiments, the culture methods reduce the concentration of ROS during the cell culturing process. As used herein, the terms reactive oxygen species or ROS shall be given their ordinary meaning and shall include, but not be limited to, superoxide anions ($O_2-$), hydrogen peroxide ($H_2O_2$), hydroxyl radicals (OH—), organic hydroperoxides (ROOH), alkoxy (RO) and peroxy (ROO) radicals, hypochlorous acid (HOCl), and peroxynitrite (ONOO—), and combinations thereof.

In several embodiments, antioxidant compositions are provided in a range of about 0.1 to about 1000 μM. In some embodiments, about 0.3 to about 50 μM of a custom antioxidant cocktail (e.g., a formulation comprising vitamin C, vitamin E, and glutathione) reduces the formation of ROS. In some embodiments, ROS production is reduced by about 10-30%. In some embodiments ROS production is reduced by about 20-50%, or at least about 25, 28, 31, 34, 37, 40, 43, 46, and 49%. In some embodiments, ROS production is reduced by about 40-80%. In some embodiments, ROS production is reduced by up to about 90%. As discussed below, in some embodiments, cells with a large reduction in ROS still exhibit DNA damage. In some embodiments, use of the antioxidants described herein reduce the formation, viability, and/or activity of ROS, and/or enhance the degradation of ROS. In some embodiments, an antioxidant cocktail (or composition) comprises one or more of the following antioxidants: vitamin A, vitamin C, vitamin E, glutathione, mixed carotenoids (e.g., beta carotene, alpha carotene, gamma carotene, lutein, lycopene, phytopene, phytofluene, and astaxanthin), selenium, Coenzyme Q10, indole-3-carbinol, proanthocyanidins, resveratrol, quercetin, catechins, salicylic acid, curcumin, bilirubin. oxalic acid, phytic acid, lipoic acid, vanilic acid, polyphenols, flavanoids, ferulic acid, theaflavins, derivatives thereof, and other antioxidants.

In some embodiments, in addition to or in lieu of the decreased production of ROS, the scavenging (e.g., processing) of ROS is increased. In some embodiments, the activity of ROS scavenging enzymes is increased. In some embodiments, superoxide dismutase expression and/or function is increased. In some embodiments, glutathione peroxidase expression and/or function is increased. In still further embodiments, one or more of lactoperoxidase, catalase, and peroxiredoxins expression and/or function is increased.

In some embodiments, the culture methods reduce the mitochondrial metabolism and therefore reduce the formation of ROS and/or the leakage of ROS from the mitochondrial membrane. In some embodiments intracellular concentration of adenosine triphosphate (ATP) is reduced, either alone or in combination with a decrease in mitochondrial membrane potential. However, in other embodiments, the incidence of karyotypic abnormalities is reduced in the absence of significant changes in ATP concentrations or mitochondrial membrane potential.

In several embodiments, the culture methods described herein decrease the DNA damage caused by ROS formation. In some embodiments, one or more markers of DNA damage is reduced, as compared to stem cells cultured under standard conditions and/or with standard media. In some embodiments, $\gamma$-$H_2AX$ mRNA and/or protein expression is decreased when a certain concentration range of antioxidant cocktail is employed, as discussed in more detail below. Numerous other markers for various types of DNA or histone damage that are known in the art may also be used to evaluate the efficacy of the methods and compositions disclosed herein.

As discussed above, some tissues have lower in vivo oxygen concentrations. Thus, in some embodiments, the culturing method comprises reducing the oxygen concentration in which the cells are cultured. In some embodiments, in vitro $O_2$ concentrations that are substantially equivalent to in vivo $O_2$ concentrations are used. In some embodiments, $O_2$ concentrations less than 20% are used. In some embodiments, $O_2$ concentrations of about 10-15% are used, while in some embodiments, $O_2$ concentrations of about 13-19% are used. In other embodiments, $O_2$ concentrations of less about 10% are used, including 9%, 8%, 7%, and 6%. In still other embodiments, $O_2$ concentrations of about 5% or less are used, including 4%, 3%, 2%, and 1%. In one embodiment, the closer the culture conditions in which a stem cell is culture are to its native oxygen conditions, the fewer karyotypic abnormalities will manifest, as the cells is being cultured in what is effectively a more natural environment. In contrast, non-physiological hyperoxic conditions in culture may lead to oxidative stress, which, as discussed above, may induce ROS formation. In other embodiments, karyotypic abnormalities are reduced when $O_2$ concentrations are about 5-75% lower in vitro, as compared to the in vivo environment.

In several embodiments, the culture method comprises supplementation of culture media with an antioxidant cocktail. Several embodiments of the composition of the cocktail are discussed in more detail below. In some embodiments, the addition of antioxidants increases the consumption (e.g., scavenging) of ROS. In turn, the reduction in ROS reduces the amount of DNA damage. In several embodiments, the addition of antioxidants increases the innate DNA repair mechanisms already present in the cell. In some embodiments, the function of the existing DNA repair enzymes is upregulated, while in some embodiments, the expression of one or more components of one or more DNA repair mechanisms is increased.

Despite the negative effects of excessive ROS formation, excessive reduction in ROS levels can also be damaging to cultured cells. In one embodiment, significant reductions in ROS levels may cause a downregulation of the innate DNA repair mechanisms (either expression, function, or both). Though unexpected, excessive reduction of ROS levels, as could be achieved by certain levels of antioxidant supplementation, could induce DNA damage due to the lack of sufficient DNA repair mechanisms or activity.

Advantageously, several embodiments of the compositions and culture methods disclosed herein strike an optimal balance between ROS reduction and maintenance of adequate levels of innate DNA repair. In other words, in some embodiments, the culture methods and compositions used herein decrease ROS levels sufficient to reduce DNA damage due to oxidative stresses, but at the same time do not reduce ROS levels to the degree that innate DNA repair function is compromised. In several embodiments, antioxidant compositions are added in a range of about 0.1 to about 1000 µM. While both high and low concentrations of antioxidants appear to result in high levels of DNA damage, intermediate concentrations unexpectedly result in reduced levels of DNA damage. In some embodiments, DNA damage is reduced when an antioxidant cocktail is added in a concentration of about 0.1 to about 200 µM (e.g., about 0.1-20 µM, 1-20 µM, 5-20 µM, 10-20 µM, 10-30 µM, 0.1-50 µM, 1-50 µM, 10-50 µM, 25-50 µM, and overlapping ranges thereof). In some embodiments, the antioxidant cocktail is added in a concentration of about 5 µM to about 30 µM. In some embodiments, about 10 µM is used. In some embodiments, about 20 µM is used.

In several embodiments, compositions comprising various antioxidant compounds are provided in order to decrease the incidence of karyotypic abnormalities in the cultured cells, e.g., as disclosed above. Compositions disclosed herein may be used to affect any of the methods disclosed herein, unless otherwise specified. In some embodiments, the compositions are used to supplement a culture media.

In several embodiments, the composition comprises one or more non-peptide antioxidants. As used herein, the term "non-peptide antioxidant" shall be given its ordinary meaning and shall also be understood to include vitamins and other chemical compounds capable of reducing ROS molecules, such as thiols (e.g., mercaptans) or polyphenols. In some embodiments, the composition comprises one or more antioxidant vitamins, including, but not limited to, vitamin A, vitamin C (ascorbic acid), and/or vitamin E. In some embodiments, one or more of vitamin A, C or E are provided at a concentration ranging from about 0.1 to about 1000 µM. In some embodiments, one or more of Vitamin A, C, or E are added in a concentration ranging from about 1 to about 500 µM. In some embodiments, one or more of Vitamin A, C, or E are added in a concentration ranging from about 0.1 to about 200 µM (e.g., about 0.1-20 µM, 1-20 µM, 5-20 µM, 10-20 µM, 10-30 µM, 0.1-50 µM, 1-50 µM, 10-50 µM, 25-50 µM, 50-100 µM, 100-200 µM, and overlapping ranges thereof). In some embodiments, one or more of Vitamin A, C, or E are added in a concentration ranging from about 75 to about 150 µM, including about 80, 90, 100, 110, 120, 130, and 140 µM. In some embodiments, one or more of Vitamin A, C, or E are added in a concentration ranging from about 1 to about 50 µM, including about 5, 10, 20, 30, and 40 µM. Other non-peptide antioxidants include, but are not limited to: mixed carotenoids (e.g., beta carotene, alpha carotene, gamma carotene, lutein, lycopene, phytopene, phytofluene, and astaxanthin), selenium, Coenzyme Q10, indole-3-carbinol, proanthocyanidins, resveratrol, quercetin, catechins, theaflavins, salicylic acid, curcumin, bilirubin. oxalic acid, phytic acid, lipoic acid, vanilic acid, polyphenols, penicillamine, flavanoids, ferulic acid, theaflavins, derivatives thereof, and other antioxidants. In several embodiments, such non-peptide antioxidants are used in the concentrations described above.

In several embodiments, the composition comprises one or more peptide antioxidants. As used herein, the term "peptide antioxidant" shall be given its ordinary meaning and shall also be understood to include full-length proteins, protein fragments, enzymes or polypeptides, amino acids, or polypeptide precursor molecules. In some embodiments, the peptide antioxidant is added in addition to the non-peptide antioxidant described above. In other embodiments, the peptide antioxidant (or the non-peptide antioxidant) is used alone to supplement the culture media. In some embodiments polypeptides such as glutathione are incorporated into the composition. In some embodiments, glutathione is incorporated into the composition at a concentration ranging from about 0.1 to about 1000 µM. In some embodiments, glutathione is added in a concentration ranging from about 1 to about 500 µM. In some embodiments, glutathione is added in a concentration ranging from about 0.1 to about 200 µM (e.g., about 0.1-20 µM, 1-20 µM, 5-20 µM, 10-20 µM, 10-30 µM, 0.1-50 µM, 1-50 µM, 10-50 µM, 25-50 µM, 50-100 µM, 100-200 µM, and overlapping ranges thereof). In some embodiments, glutathione is added in a concentration ranging from about 75 to about 150 µM, including about 80, 90, 100, 110, 120, 130, and 140 µM. In some embodiments, glutathione is added in a concentration ranging from about 1 to about 50 µM, including about 5, 10, 20, 30, and 40 µM. Other peptide antioxidants include, but are not limited to: superoxide dismutases, peroxiredoxins, thioredoxin, ceruloplasmin, transferrins, hydroperoxide reductases, n-acetylcysteine and, in several embodiments, are used in the concentrations described above.

In several embodiments, methods for assessing a subject's risk of developing a neoplastic disease are provided. In one embodiment, the method comprises obtaining and evaluating a tissue sample from the subject for evidence of karyotypic abnormalities (e.g., DNA damage) and correlating any detected abnormalities with the subject's antioxidant levels. Thereafter, the subject is optionally treated to reduce or increase antioxidant levels as needed. In several embodiments, DNA damage is detected by analysis of markers of DNA damage, quantifying DNA damage-associated mRNA expression levels, and/or quantifying DNA damage-associated protein expression levels. In one embodiment, the risk of developing neoplastic disease increases as the incidence of DNA damage increases, as the expression of DNA damage-associated mRNA increases, and/or as the expression of DNA damage-associated protein increases. In some embodiments, identification of $\gamma$-$H_2AX$ foci, quantifying $\gamma$-$H_2AX$ mRNA expression levels, and/or by quantifying $\gamma$-$H_2AX$ protein expression levels, or combinations thereof, are used to detect and/or quantify DNA damage.

In several embodiments, a method for optimizing a subject's intake of an antioxidant-containing supplement is provided. In one embodiment, the method comprises measuring the concentration of one or more reactive oxygen species in a sample obtained from the subject (e.g., a tissue or blood sample) and measuring the incidence of DNA damage in cells isolated from said sample. In some embodiments, the expression of DNA repair enzymes in cells isolated from said sample is measured. In some embodiments, both DNA damage and expression of DNA repair enzymes are measured.

In one embodiment, the method further comprises administration of an antioxidant composition to the subject (and optionally adjusting said composition in subsequent administrations) in order to achieve an optimal degree of homeostasis between the concentration of reactive oxygen species in the subject and the subject's endogenous DNA repair mechanism(s). Such a level of reactive oxygen species can be assessed by, for example, expression of DNA repair enzymes or other markers of DNA repair. In several embodiments, antioxidant compositions (e.g., supplements) comprising an optimal amount of antioxidant-containing supplement are provided. Such compositions are formulated to reduce DNA damage caused by oxidative-stress but to minimize negatively impacting (wholly or partially) the subject's endogenous DNA repair mechanisms. In several embodiments, the methods comprise serial administrations of antioxidant compositions having different concentrations of antioxidant compounds to a subject. In some embodiments, the invention comprises optimizing antioxidant therapy for an individual. In one embodiment, a first sample (e.g., tissue or blood sample) is obtained from the subject prior to administration, in order to establish a baseline. Thereafter, a first antioxidant composition having a first concentration of an antioxidant composition is administered. An additional sample is obtained from the subject and evaluated for concentrations of reactive oxygen species, markers of DNA damage, changes in expression of DNA repair enzymes, or combinations thereof. In some embodiments, a plurality of additional administrations of an antioxidant composition (optionally having varying concentrations of antioxidant compounds) may be made in conjunctions with obtaining and evaluating a plurality of additional samples from the subject. As such, an optimal concentration of antioxidant compounds may be reached over time by the serial evaluation of the subject's response to the antioxidant compositions. Thus, in several embodiments, therapeutic antioxidant compositions that balance oxidative damage with endogenous DNA repair mechanisms are provided based on a subject's individual antioxidant and/or karyotypic profile. Antioxidant compositions according to several embodiments herein comprise, consist, or consist essentially of one, two, three, five, ten, or more antioxidants.

EXAMPLES

Examples provided below are intended to be non-limiting embodiments of the invention.

Materials and Methods

The following materials, methods, and protocols may be used to perform the examples disclosed herein as well as practice the various embodiments of the invention disclosed herein.

Long-Term Culture Conditions for Human CDCs

Adult human cardiac stem cells were isolated from percutaneous septal endomyocardial heart tissue biopsies (about 10-20 μg), which were obtained from patients during clinically-indicated procedures (to monitor heart transplant recipients for rejection) after informed consent. Biopsies were minced into small fragments and digested with 0.2 mg/ml collagenase for 30 minutes. The digested tissue fragments were then equally moved to each of four 6-cm diameter culture dishes coated with 20 μg/ml fibronectin (BD Biosciences), and randomly selected to culture as "explants" in the following four conditions:
 1) in a typical 20% $O_2$ incubator (95% air/5% $CO_2$);
 2) in a 5% $O_2$ "hypoxia incubator";
 3) in a typical 20% $O_2$ incubator with the addition of 1000-fold diluted proprietary antioxidant supplement (Sigma-Aldrich, Catalogue Number: Sigma A1345, Antioxidant A);

or
 4) a custom antioxidant cocktail consisting of 100 μM L-ascorbate, L-glutathione, and alpha-tocopherol acetate (Sigma-Aldrich, Antioxidant B).

The cardiosphere and CDC amplification steps were performed under the same conditions in each group. IMDM basic medium (Gibco) supplemented with 10% FBS (Hyclone) and 20 mg/ml gentamycin was used for all cultures. As used herein, the term "short-term culture" shall be given its ordinary meaning and also be read to include culture periods ranging from about 1 to about 48 hours, including, 8, 16, 20, 24, 32, 36, and 40 hours. As used herein, the term "long-term culture" shall be given its ordinary meaning and also be read to include culture periods ranging from 48 hours to 6 months. In some embodiments, long-term culture lasts for several days to several months, including 2, 3, 4, and 5 months. In some embodiments, long-term culture lasts for several days to several weeks, include 1-3 weeks, 2-5, weeks, 3-7 weeks, and 5-10 weeks. In some embodiments long-term culture lasts for about 6 to about 10 months, and in some embodiments from about 10 months to several years.

Karyotype Analysis

Twice-passaged CDCs (with long-term culture for 1-2 months from the date of tissue biopsy) were seeded onto fibronectin-coated 25-cm$^2$ tissue culture flask ($10^4$ cells/cm$^2$). After ~24 hours of incubation, cells were treated with 0.1 μg/ml colcemid (Invitrogen) for 4 hours, then trypsinized, treated with hypotonic solution, and fixed. Metaphases were spread on microscope slides, and karyotype analysis was done by using standard G banding technique. The chromosomes were classified according to the International System for Human Cytogenetic Nomenclature. At least 20 metaphases were analyzed per cell sample.

Determination of ROS Levels

To assay intracellular ROS levels (ROS levels), twice-passaged CDCs were seeded in 6- or 96-well plates coated with 20 μg/ml fibronectin, and continuously cultured under the abovementioned four different conditions. At about 90% confluence, cells were incubated with 10 μM 2',7'-dichlorodihydrofluorescein diacetate (DCFH-DA) (Invitrogen) for 60 min to allow DCFH-DA to diffuse into cells. The DCF fluorescence intensity in cells cultured in 96-well plates is directly determined using SpectraMax® M5 (Molecular Devices Corp.) with an excitation wavelength of 495 nm and an emission wavelength of 520 nm. Cells cultured in 6-well plates were trypsin-treated and fixed. The DCF fluorescence intensity in cells was analyzed using a FACS Calibur flow cytometer with CellQuest software (BD Biosciences).

To observe the changes of ROS levels during short-term exposure to different concentrations of antioxidants, catalase, and $H_2O_2$, CDCs were expanded by traditional conditions under 20% $O_2$ as described above. Twice-passaged cells were seeded in 6- or 96-well plates coated with 20 μg/ml fibronectin. When about 70% confluent, cell cultures were supplemented with antioxidant A (100-1,000,000-fold dilution), custom antioxidant cocktail "B" (0.1-1000 μM), catalase (0.1-1000 units/ml), or $H_2O_2$ (0.1-1000 μM), as indicated. After 24 hours of culture, the DCF fluorescence intensity in cells was measured using the same methods as disclosed above.

Analysis of DNA Damage in CDCs and ES Cells

DNA damage in human CDCs and ES cells was evaluated by immunostaining for phosphorylation of histone $H_2AX$ on serine 139 (γ-$H_2AX$), a marker of DNA double-strand breaks, after short-term culture with different concentrations of antioxidants, catalase, and $H_2O_2$. CDCs were expanded in conventional conditions under 20% $O_2$ as described above.

Twice-passaged CDCs and ES cells were used in these Examples. Cells were seeded in 96-well plates coated with 20 μg/ml fibronectin. When about 70% confluent, cell cultures were supplemented with antioxidant A (100-1,000,000-fold dilution), custom antioxidant cocktail "B" (0.1-1000 μM), catalase (0.1-1000 units/ml), or $H_2O_2$ (0.1-1000 μM), as indicated. After 24 hours of culture, cells were fixed, permeabilized and stained with rabbit polyclonal antibody against γ-$H_2$AX (phosphor S139, Abcam Inc.). After being washed, the cells were stained with a PE-conjugated secondary antibody and 4,6-diamidino-2-phenylindole (DAPI). Quantification of cells positive for γ-$H_2$AX foci was performed by fluorescence microscopy (×40 magnification). Briefly, at least 5 images were captured from each culture condition from randomly-selected fields using Q-imaging (RETIGA EXi FAST, Canada) with the same exposure time. Cells with γ-$H_2$AX foci in the nuclei were counted by a single observer blinded to treatment regimen, and the percentage of cells with γ-$H_2$AX foci in each culture condition was used for statistical analysis.

To quantify DNA damage in long-term cultured CDCs under the abovementioned four different conditions, twice-passaged CDCs were seeded in 6- or 96-well plates coated with 20 μg/ml fibronectin, and continuously cultured for 24 hours. The analysis of γ-$H_2$AX foci was done as described above.

Western Blotting

To examine the protein levels of ATM and other DNA repair-related factors, total protein was purified from twice-passaged CDCs cultured under the abovementioned four different conditions, using well-established laboratory techniques. Briefly, harvested cells were homogenized in a lysis buffer containing a protease inhibitor mixture (Roche Applied Science) on ice. After centrifugation at 15,000 rpm for 10 min, the supernatant was collected for experiments. The equivalent of 30 μg of total protein was loaded onto 5% or 10% SDS-PAGE gels, and then transferred to PVDF membranes. After overnight blocking in 3% milk TBS-T, membranes were incubated with the following primary antibodies: 1:5000 dilution of rabbit anti-ATM polyclonal antibody, 1:1000 dilution of rabbit anti-ATR polyclonal antibody, 1:500 dilution of rabbit anti-Chk1 (phosphor S317) polyclonal antibody, 1:200 dilution of rabbit anti-Chk2 (phosphor T26) polyclonal antibody, 1:1000 dilution of mouse anti-Rad50 monoclonal antibody, 1:1000 dilution of mouse anti-Rad51 monoclonal antibody (all from Abcam Inc.) and 1:3000 dilution of rabbit anti-β-actin monoclonal antibody. The appropriate horseradish peroxidase-conjugated secondary antibodies were used, and then the blots were visualized by using SuperSignal West Femto maximum sensitivity substrate (Thermo Scientific)) and exposed to Gel Doc™ XR System (Bio-Rad Lab., Inc.). Quantitation for blots was done by Quantity One software, and expressions were normalized by β-actin.

To observe the expression of ATM and other DNA repair-related factors during short-term exposure to different concentrations of antioxidants, catalase, and $H_2O_2$, CDCs were expanded by traditional culture in 20% $O_2$ as described above. Twice-passaged cells were seeded in 6-well plates coated with 20 μg/ml fibronectin. When about 70% confluent, cells were cultured in 20% $O_2$ with the supplement of antioxidant A (100-1,000,000-fold dilution), custom antioxidant cocktail "B" (0.1-1000 μM), catalase (0.1-1000 units/ml), or $H_2O_2$ (0.1-1000 μM), as indicated. After 24 hours of culture, cells were harvested and total protein was purified. The expression of ATM and other DNA repair-related factors was assessed by Western blotting as described above.

Measurement of the Intracellular ATP Level and Mitochondrial Transmembrane Potential The intracellular ATP level was measured by the luciferin-luciferase method using an ATP-determination kit (Invitrogen). Briefly, twice-passaged CDCs (2×$10^5$ cells/well) were seeded in 6-well plates coated with 20 μg/ml fibronectin, and continuously cultured under the abovementioned four different conditions for 24 hours. The cells were washed twice with ice-cold PBS and lysed in 200 μl lysis buffer with protease inhibitors. The lysates (20 μl normalized by protein content) were added to the reaction solution (200 μl) containing 0.5 μM luciferin, 1.25 μg/ml luciferase, and 1 μM DTT, and the bioluminescence was measured using a Monolight™ 3010 (Pharmingen).

To measure mitochondrial transmembrane potential, twice-passaged CDCs (2×$10^5$ cells/well) were seeded in 6-well plates coated with 20 μg/ml fibronectin, and continuously cultured under the abovementioned four different conditions for 24 hours. Cells were loaded with TMRE at 37° C. for 30 minutes, and harvested by trypsinization. The fluorescence intensity in cells was analyzed using a FACS Calibur flow cytometer with CellQuest software (BD Biosciences).

Statistical Analysis

All results are presented as mean±SD. Statistical significance was determined using the 2-tailed chi-square test for karyotype data and ANOVA followed by Bonferroni post hoc test for other data (Dr. SPSS II). Differences were considered statistically significant when $p<0.05$.

Example 1

Genomic Alterations Decrease in Physiological Oxygen but Unexpectedly Increase with Antioxidant Supplements Source human heart biopsies (n=16) were divided and processed in parallel in the various culture conditions, facilitating direct comparisons. CDCs grown under conventional conditions not infrequently included cells with genomic alterations (6 of 16 samples; FIG. 1, Table 1 and Table 2). In reference to FIG. 1, each bar represents a histogram of one sample of stem cells; blue denotes cells with a normal karyotype. Compared with culture in traditional 20% $O_2$ incubator (95% room air/5% $CO_2$), the number of cells with DNA breaks or translocations (colored green) and losses or gains of chromosomes (red) was decreased when cells were cultured in 5% $O_2$ (p=0.007). When CDCs were cultured in 5% $O_2$, genomic alterations were detected in only 3 of 16 samples (FIG. 1, Table 2). The genomic changes were relatively innocuous: one sample contained one cell with a balanced translocation, another had 8 cells with a derivative chromosome, and the third included one cell with loss of the Y chromosome (FIG. 1, Table 2). The reduction of the frequency of chromosomal abnormalities in CDCs cultured in 5% $O_2$ indicates that physiological oxygen concentrations during culture enhance the genomic stability of stem cells.

TABLE 2

Karyotyping Date of Twice-Passaged Human CDCs

| Samples | 20% $O_2$ | Antioxidant A | Antioxidant B | 5% $O_2$ |
|---|---|---|---|---|
| CSB59m | 46, XY[20] | 46, XY[20] | 46, XY[20] | 46, XY[20] |
| CSB59s | 46, XY[20] | 45, X – Y[10]/46, XY[10] | 46, XY[20] | 46, XY[20] |
| CSB61m | 46, XY[20] | 47, XY, +7[3]/46, XY[17] | 47, XY, +7[3]/46, XY[18] | 46, XY[20] |
| CSB61s | 46, XY[20] | 47, XY, +7[1]/46, XY[19] | 46, XY[20] | 46, XY[20] |
| CSB64m | 46, XY[20] | 48, XY, +2, +20[4]/46, XY, der(13)t(9; 13)(q12; p11, 2)[1]/46, XY[15] | 46, XY[20] | 46, XY[20] |
| CSB64s | 46, XY[20] | 46, XY[20] | 46, XY[20] | 46, XY[20] |
| CSB65m | 47, XY, +8[9]/48, s1, +2, –9, der(13)t(9; 13)(q12; p11.1), +14[1]/46, XY[11] | 46, XY[20] | 46, X, +8[7]/47, XY, +12 [10]/46, XY[3] | 46, XY[20] |
| CSB65s | 45, X, –Y[2]/47, XY, +8[1]/46, XY[20] | 47, XYY[4]/46, XY[16] | 47, XYY[11]/47, XY, +2 [1]/47, XY, +8[5]/46, XY[3] | 46, XY[20] |
| CSB66m | 47, XX, +2[1]/ 47, XX, m[1]/46, XX[18] | 46, XX[20] | 46,XX | 46, XX[20] |
| CSB66s | 46, XX[20] | 47, XX, +8[1]/46, XX[19] | 46, XX, add(1)(p36.1)[3]/ 46, XX[18] | 46, XX[20] |
| CSB69m | 47, XY, +8[2]/45, X, –Y[1]/46, XY[18] | 47, XY, +8[5]/46, XY[15] | 47, XY, +8[4]/ 46, XY[16] | 46, XY, der(18)t(14; 18) (q22; q23)[3]/46, XY[17] |
| CSB69s | 46, XY[20] | 47, XY, +8[17]/46, XY[3] | 47, XY, +8[5]/ 46, XY[15] | 46, XY, der(18)t(14; 18) (q22; q23)[5]/45, X, –Y[1]/46, XY[15] |
| CSB73m | 46, XY[20] | ND | ND | 46, XY, t(6; 19)[1]/ 46, XY[19] |
| CSB73s | 46, XY[20] | ND | ND | 46, XY[20] |
| CSB76m | 45, X, –Y[6]/46, XY[14] | ND | ND | 46, XY[20] |
| CSB76s | 45, X, –Y[1]/47, XY, +8[1]/46, XY[18] | ND | ND | 46, XY[20] |

In contrast, karyotypic abnormalities were dramatically increased in frequency and severity when CDCs were cultured in 20% $O_2$ with either of two antioxidant cocktails: a proprietary antioxidant supplement for cell culture (product A1345, Sigma-Aldrich, 1000-fold dilution; Antioxidant A), or a custom antioxidant mixture (L-ascorbate, L-glutathione, and α-Tocopherol acetate, each 100 μM; Antioxidant B) (FIG. 1, Table 2). Among the 12 samples of CDCs cultured with Antioxidant A or B, 8 and 6 samples included 46 and 49 cells with genomic alterations, respectively (p<0.001 vs. 20% $O_2$ culture by chi-square test, FIG. 1).

Figure 2A:
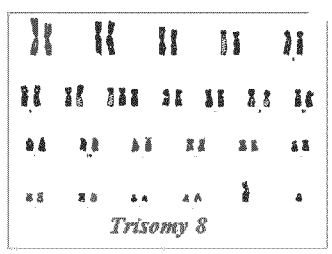
FIGS. 2A-2C depict representative karyotypes made from CDCs cultured in various conditions.
Figure 2B:
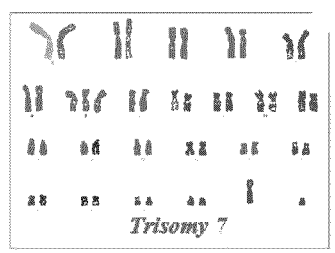
Figure 2C:
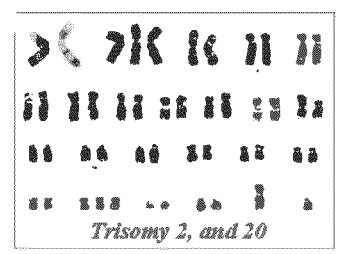

Unlike conventional 20% $O_2$ culture, where trisomy 8 and loss of Y predominated, the karyotypic abnormalities seen with antioxidants were numerous and varied (trisomy 2, 7, 8, 12, 18, and 20). FIG. 2 depicts (A) CDCs cultured in a traditional 20% $O_2$ incubator (95% air/5% C $O_2$), (B) gain of chromosome 7 in the presence of Antioxidant A, and (C) gains of chromosome 2 and 20 in the presence of Antioxidant B. To the Applicant's knowledge, some of these, namely trisomy 7 and trisomies 2 and 20 have not been previously reported (FIG. 2).

Figures 3A, 3B, 3C, 3D:
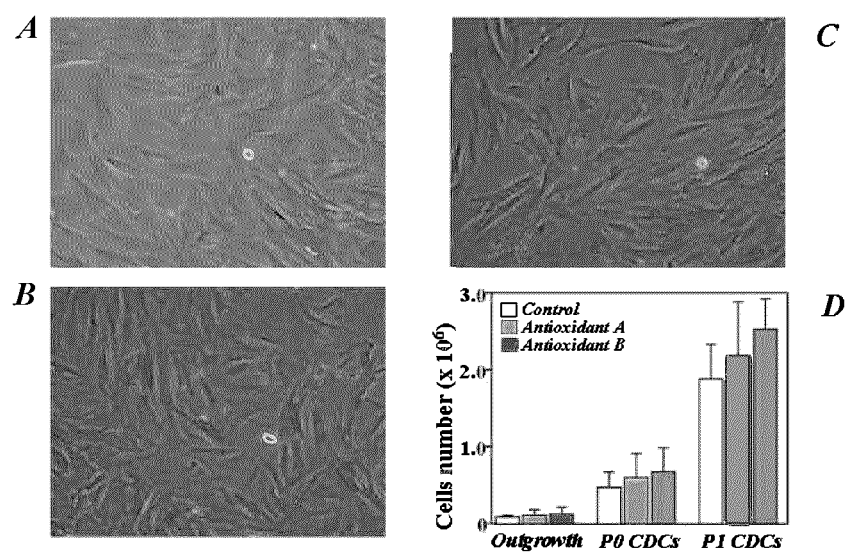
FIGS. 3A-3D depict CDC proliferation data.

The effects of antioxidants on genomic stability appear not to reflect generalized toxicity, as CDCs proliferated normally without obvious morphologic abnormalities (FIG. 3). Panel A depicts twice-passaged CDCs grown for 36 days in 20% $O_2$ without addition of antioxidants. Panel B depicts CDCs grown in the same $O_2$ concentration in media supplemented with an antioxidant supplement at 1:1000 dilution. Panel C depicts CDCs grown in the same $O_2$ concentration in media supplemented with a custom antioxidant cocktail at 100 μM. Panel D indicates that that no significant differences in CDC proliferation were detected among the various culture conditions.

Figure 4B:
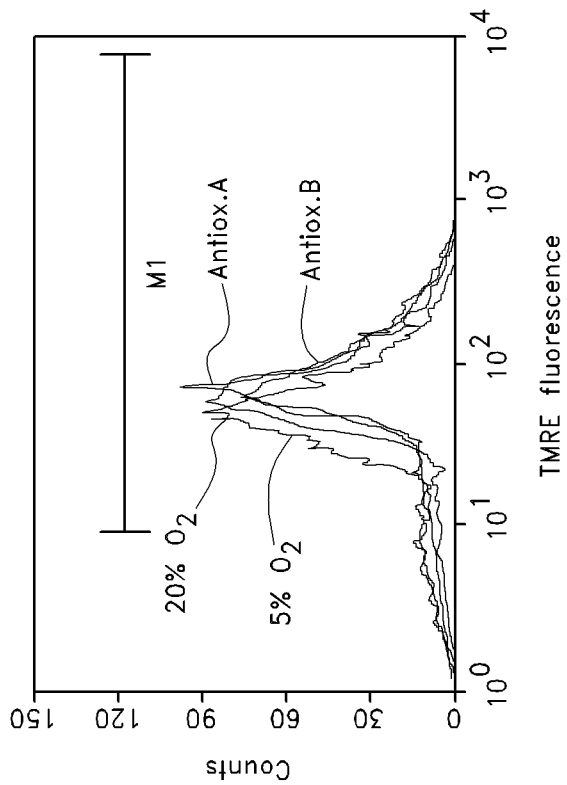
FIGS. 4A and 4B depict ATP and mitochondrial membrane potential data.
Figure 4A:
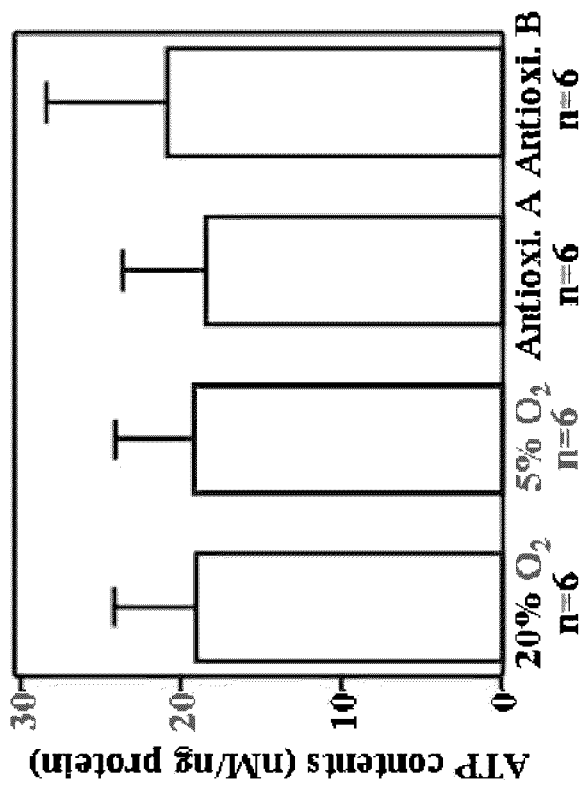

Furthermore, neither the intracellular ATP level nor mitochondrial transmembrane potential showed any obvious differences among the four various culture conditions (FIGS. 4A and B, respectively). Indeed, the similarities in cell proliferative activity and intracellular ATP levels indicate that energy metabolism is not severely undermined in any of the long-term culture conditions.

Example 2

Figures 5A, 5B, 5C, 5D:
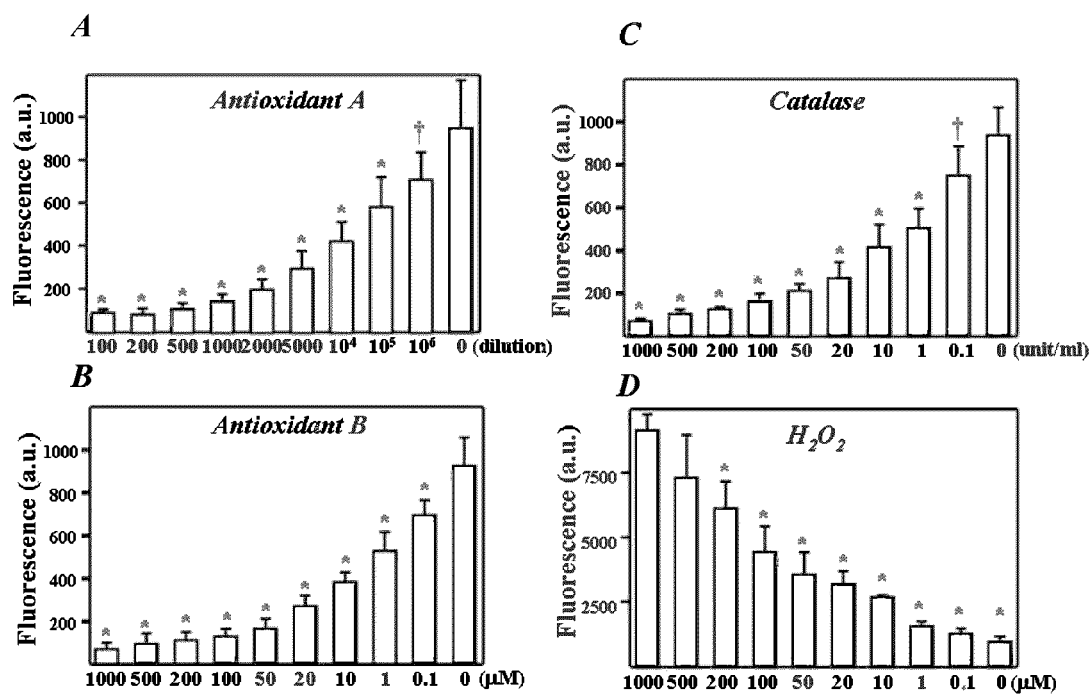
FIGS. 5A-5D depict intracellular ROS concentrations in human cardiosphere-derived cells after 24 hours culture under 20% $O_2$ with different concentrations of antioxidants (5A and 5B), catalase (5C), and hydrogen peroxide ($H_2O_2$; 5D).
Figure 6A:
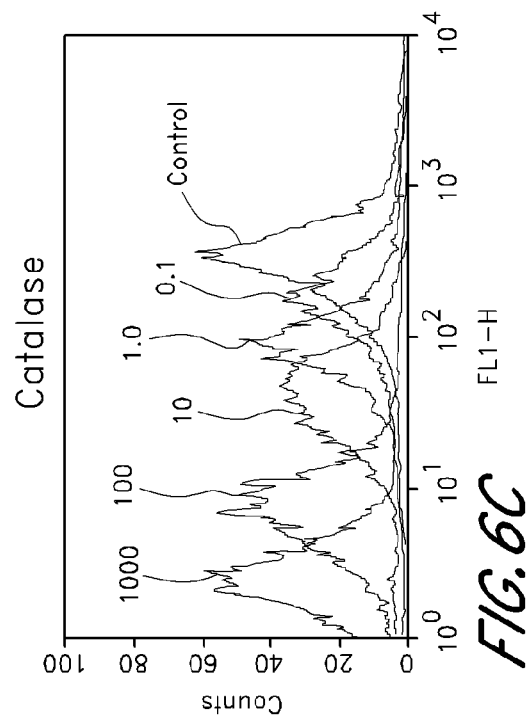
FIGS. 6A-6D depict flow cytometry assessments of intracellular ROS levels in human CDCs cultured for 24 hours with different concentrations of antioxidants (6A and 6B), catalase (6C), or hydrogen peroxide ($H_2O_2$; 6D).
Figure 6B:
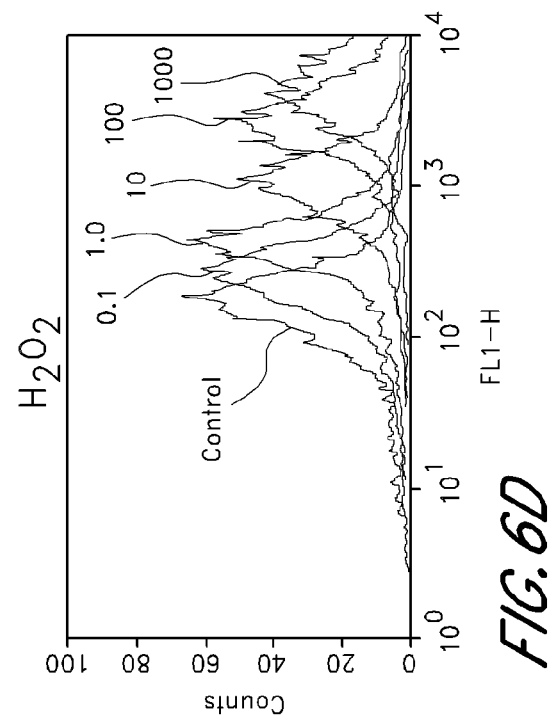
Figure 6C:
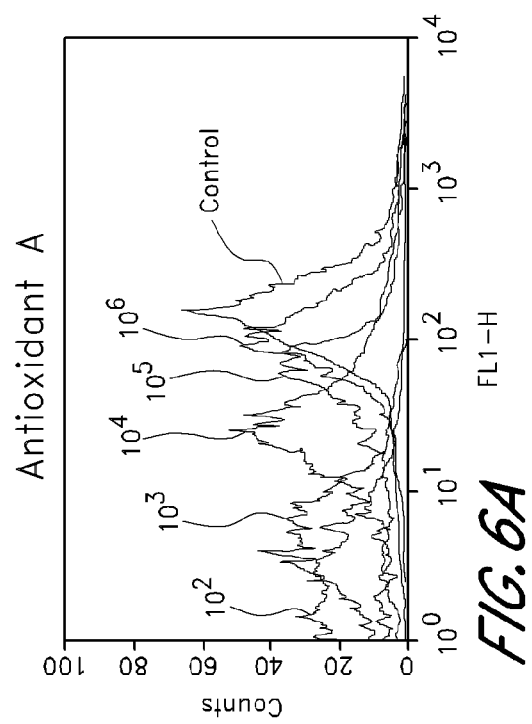
Figure 6D:
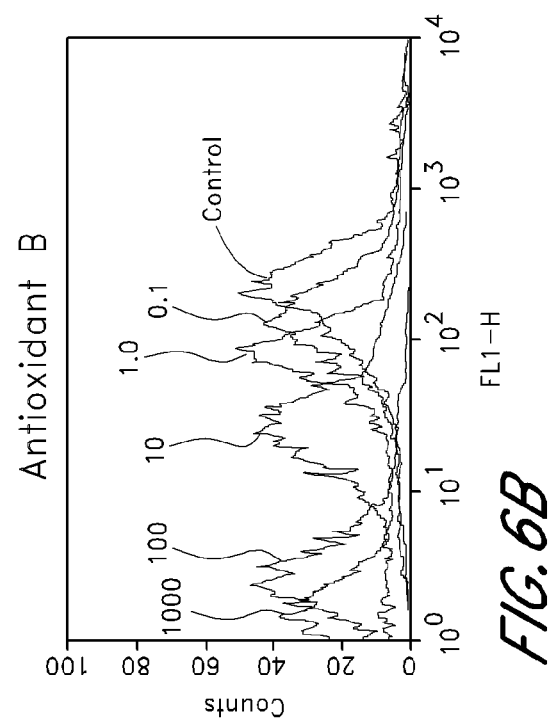

Antioxidants Decrease Intracellular ROS Monotonically but DNA Damage Shows a Biphasic Response in Stem Cells CDCs were initially maintained in traditional 5% $CO_2$/ 20% $O_2$ culture condition and then seeded into 96-well plates and cultured for 24 hours under experimental conditions. Intracellular ROS levels in CDCs exposed for 24 hours to a wide range of antioxidant concentrations (A-B), with catalase (a pure ROS scavenger, C) and hydrogen peroxide ($H_2O_2$, a powerful oxidant, D) as controls were measured. The results shown in FIG. 5 are means±Std. Dev. for six separate experiments using different twice-passaged CDCs. (a.u.: arbitrary units. * p<0.01, \ p<0.05 vs. the baseline levels., represented by "0" on the x-axis). The results shown in FIG. 6 are representative histograms of the intracellular ROS data obtained by flow cytometry Catalase decreased, and $H_2O_2$ increased, ROS levels in a progressive dose-dependent manner (FIG. 5C-D, FIG. 6C-D). Like catalase, antioxidants A and B both decreased ROS levels monotonically (FIG. 5A-B, FIG. 6A-B). At the concentrations used to culture CDCs for karyotyping analysis (1000-fold dilution of antioxidant A and 100 μM antioxidant B, respectively), ROS levels was very low.

Likewise, ROS levels was depressed in CDCs sent for karyotyping analysis after 1-2 months in 5% oxygen, and even more so in antioxidants, relative to routine culture conditions (FIG. 7). As shown in Panel A, the intracellular ROS was lower in cells cultured long-term under 5% $O_2$ than under 20% O$_2$. Intracellular ROS was decreased to very low levels by the addition of 1000-fold diluted antioxidant supplement (Antioxidant A) or 100 µM custom antioxidant cocktail (Antioxidant B), as shown in Panel B. Shown in Panel C are representative images of γ-H$_2$AX foci in CDCs (arrows) cultured for long-term under different conditions. As depicted in Panel D, compared to traditional 20% O$_2$ culture, quantitative data showed that γ-H$_2$AX foci in CDCs was significantly decreased in 5% O$_2$ culture, but increased by the supplement with antioxidants. * p<0.01 vs. other groups, † p<0.01 vs. 5% O$_2$ and 20% O$_2$. Thus, assuming that ROS levels in CDCs cultured under 5% O$_2$ approximates the physiological intracellular concentration, long-term culture with antioxidants suppresses ROS levels to sub-physiological levels (FIGS. 5, 6, and 7).

Figures 8A, 8B, 8C, 8D:
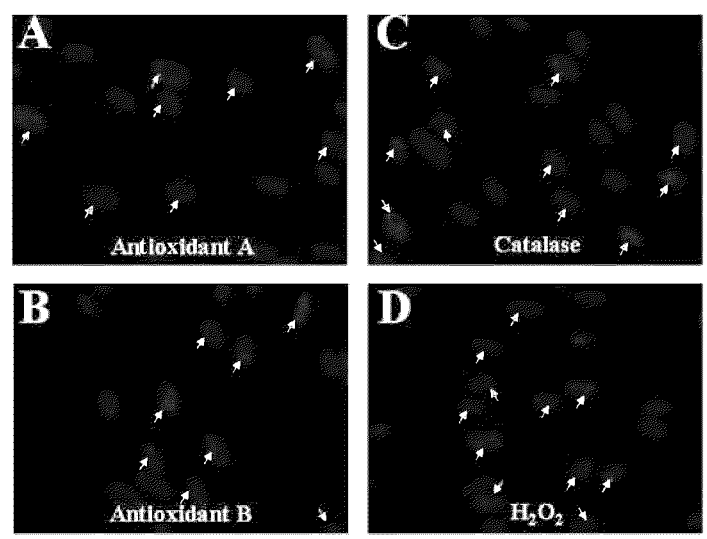
FIGS. 8A-8D depict representative microscopic images demonstrating γ-$H_2$AX foci in CDCs cultured with antioxidants (8A and 8B); catalase (8C) and hydrogen peroxide ($H_2O_2$; 8D).

The concept of "reductive stress" (an extreme suppression of ROS) may underlie a form of cardiomyopathy due to protein aggregation. To identify whether an excessive decrease of ROS levels likewise induces DNA damage and genomic instability, γ-H$_2$AX foci was quantified in CDCs and human ES cells (FIG. 8). γ-H$_2$AX is a marker of DNA double-strand breaks and was detected in several CDCs whether cultured with 1:1000 diluted antioxidant supplement (Panel A), with 100 µM custom antioxidant cocktail (Panel B), with 100 units/mL catalase (Panel C), or with 100 µM H$_2$O$_2$ (Panel D).

Figures 9A, 9B, 9C, 9D:
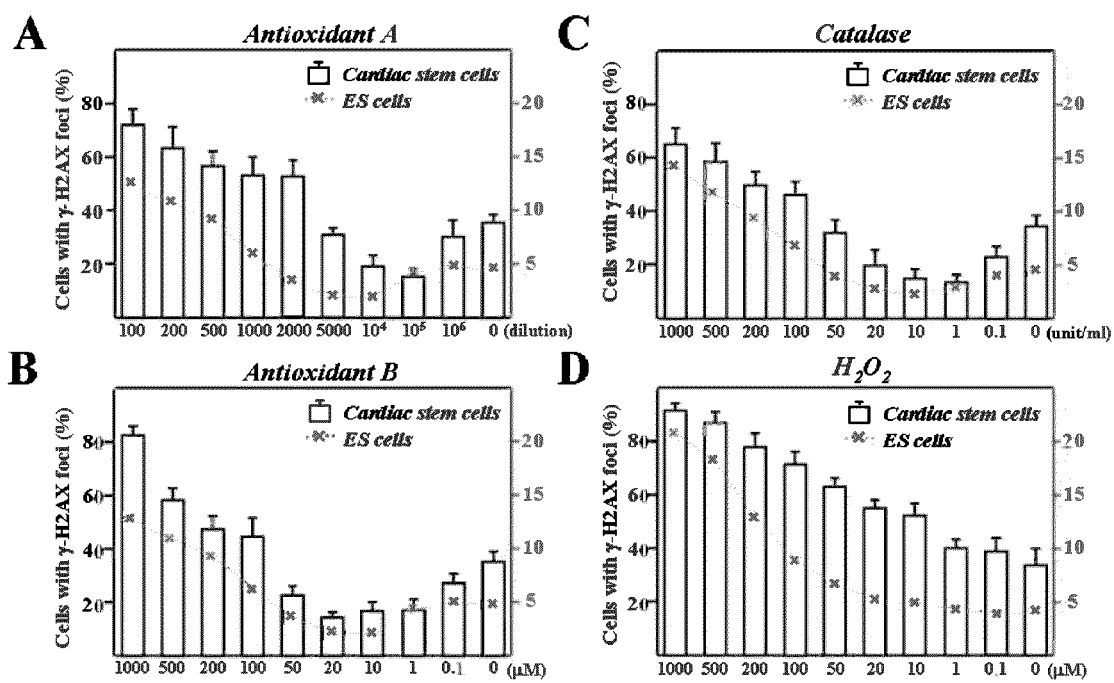
FIGS. 9A-9D depict the bi-phasic DNA damage dose-response in human CDCs and embryonic stem (ES) cells cultured with varying amounts of anti-oxidants (9A and 9B), catalase (9C) and hydrogen peroxide ($H_2O_2$; 9D).

It was also demonstrated that oxidative stress induced by H$_2$O$_2$ increased DNA damage dose-dependently (FIG. 9D). Here, however, the effects were unexpectedly biphasic: the percentage of CDCs with γ-H$_2$AX foci was decreased at low antioxidant concentrations, but increased at higher doses (FIG. 9A-B). A similar result was observed with increasing concentrations of catalase (FIG. 9C). The biphasic response is not limited to CDCs: human ES cells exhibited a similar pattern (red crosses with dotted lines, FIG. 9A-C), although the overall percentages of ES cells with γ-H$_2$AX foci were lower than in adult CDCs. Interestingly, the number of γ-H$_2$AX foci was minimal at modest concentrations of antioxidants (10,000-fold dilution of antioxidant A, 10 µM of antioxidant B, and 10 units/ml of catalase; FIG. 9A-C), the same concentrations that drive ROS levels to "physiological" levels. These results motivate the concept of an "oxidative optimum", a narrow range of ROS levels within which stem cells maintain optimal genomic stability.

Figure 7B:
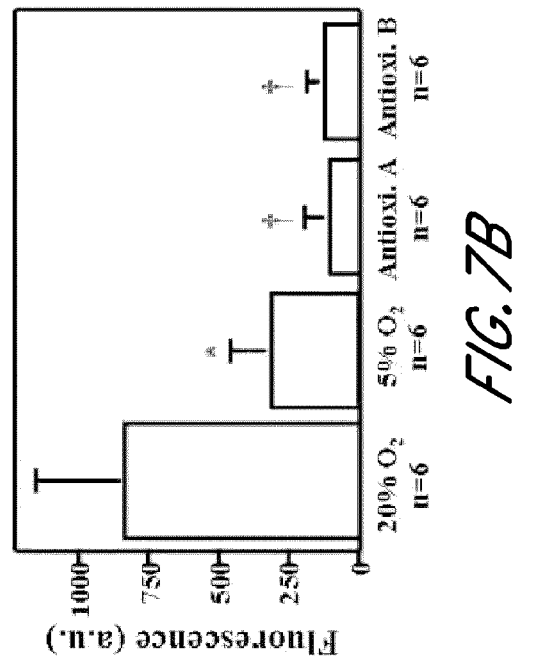
FIGS. 7A-7D depict ROS and DNA damage data.
Figure 7D:
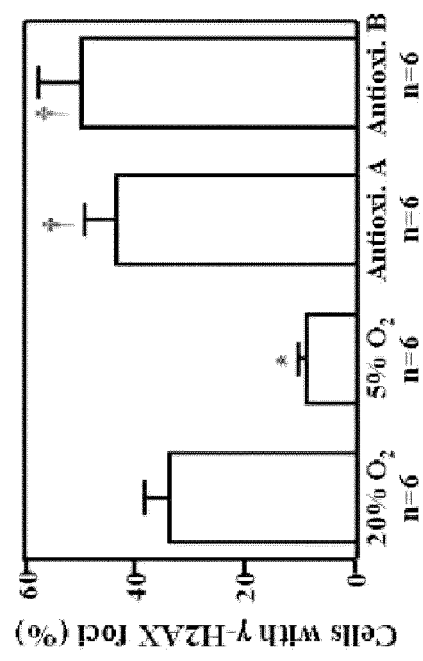
Figure 7A:
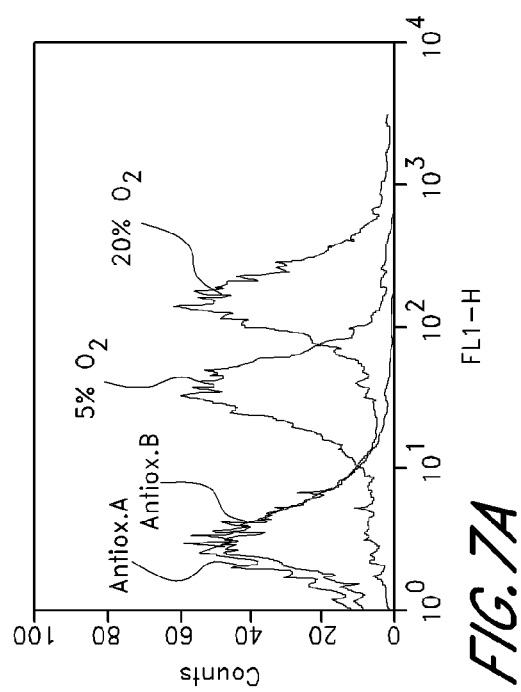
Figure 7C:
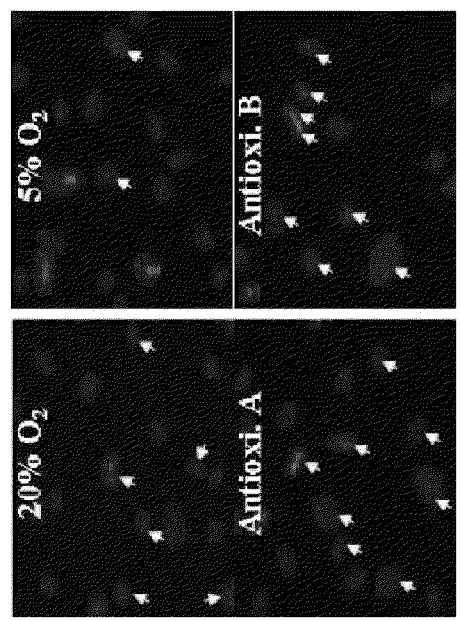

This dose-response data correlated with the results of FIGS. 7C and 7D discussed above, where γ-H$_2$AX foci were significantly decreased in 5% O$_2$ culture, but increased by supplementation with 1000-fold diluted antioxidant supplement (Antioxidant A) or 100 µM custom antioxidant cocktail (Antioxidant B), when compared to traditional 20% O$_2$ culture (FIG. 7C, D).

Example 3

Figures 10A, 10B, 10C, 10D:
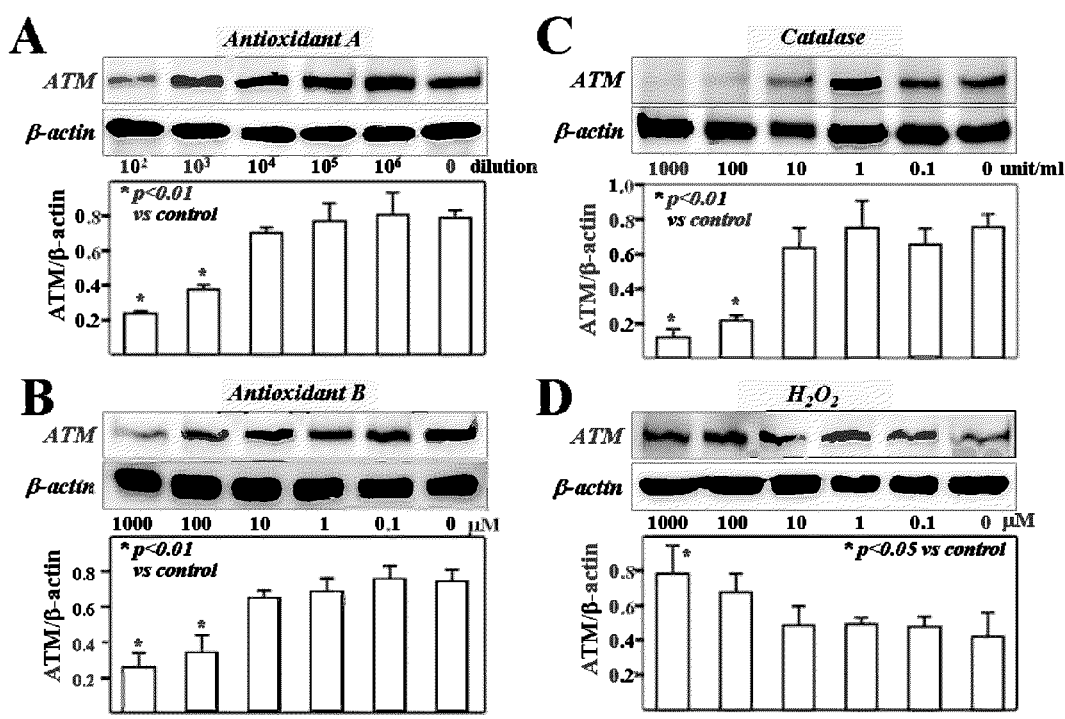
FIGS. 10A-10D depict ATM protein levels in human cardiosphere derived cells after 24 hours of culture under 20% $O_2$ with antioxidants (10A and 10B), catalase (10C), and hydrogen peroxide ($H_2O_2$; 10D).

Extreme Suppression of Intracellular ROS Down-Regulates Atm and Other DNA Repair Factors The protein kinase ATM (ataxia-telangiectasia mutated), is believed to play a role in DNA repair. Intracellular ROS enhances the expression of ATM, which phosphorylates a host of downstream targets in response to DNA double-strand breaks, inducing cell cycle arrest and inhibiting apoptosis. It is possible that excessive suppression of ROS levels might down-regulate ATM, thereby promoting genomic instability. ATM protein levels were indeed decreased at high concentrations of antioxidants A and B (≥1000-fold dilution, (≥100 µM, respectively), or catalase (≥100 units/ml) (FIG. 10A-C). As shown in Panel A, the protein levels of ATM in CDCs were decreased at high doses (≤1000-fold dilution), but not at low doses (≥10.000-fold dilution) of antioxidant supplements (Antioxidant A). Panel B shows that ATM protein in CDCs decreases at ≥100 µM, but not at ≤10 µM, of custom antioxidant cocktail (Antioxidant B). Panel C shows that catalase also decreases ATM protein level in CDCs at ≥100 units/ml, but not at ≤10 units/mL. Finally, Panel D shows that the expression of ATM in CDCs was slightly increased at a high dose (≥100 µM) of H$_2$O$_2$. Quantitative data are means±standard deviation for four separate experiments using different twice-passaged CDCs.

Figures 11A, 11B, 11C, 11D:
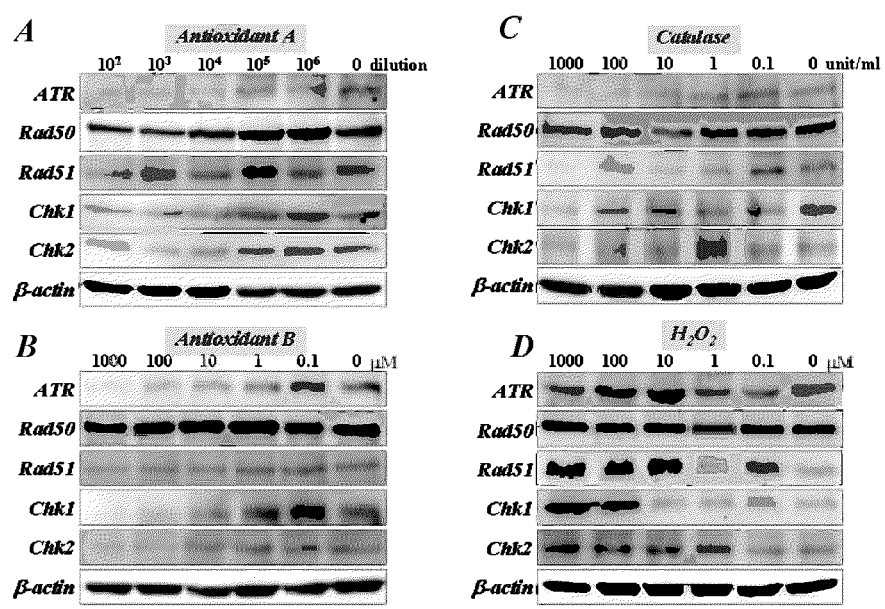
FIGS. 11A-11D depict representative western blot analysis of the expression of various DNA repair-related factors after culturing under 20% $O_2$ with antioxidants (11A and 11B), catalase (11C), and hydrogen peroxide ($H_2O_2$; 11D).
Figures 12A, 12B:
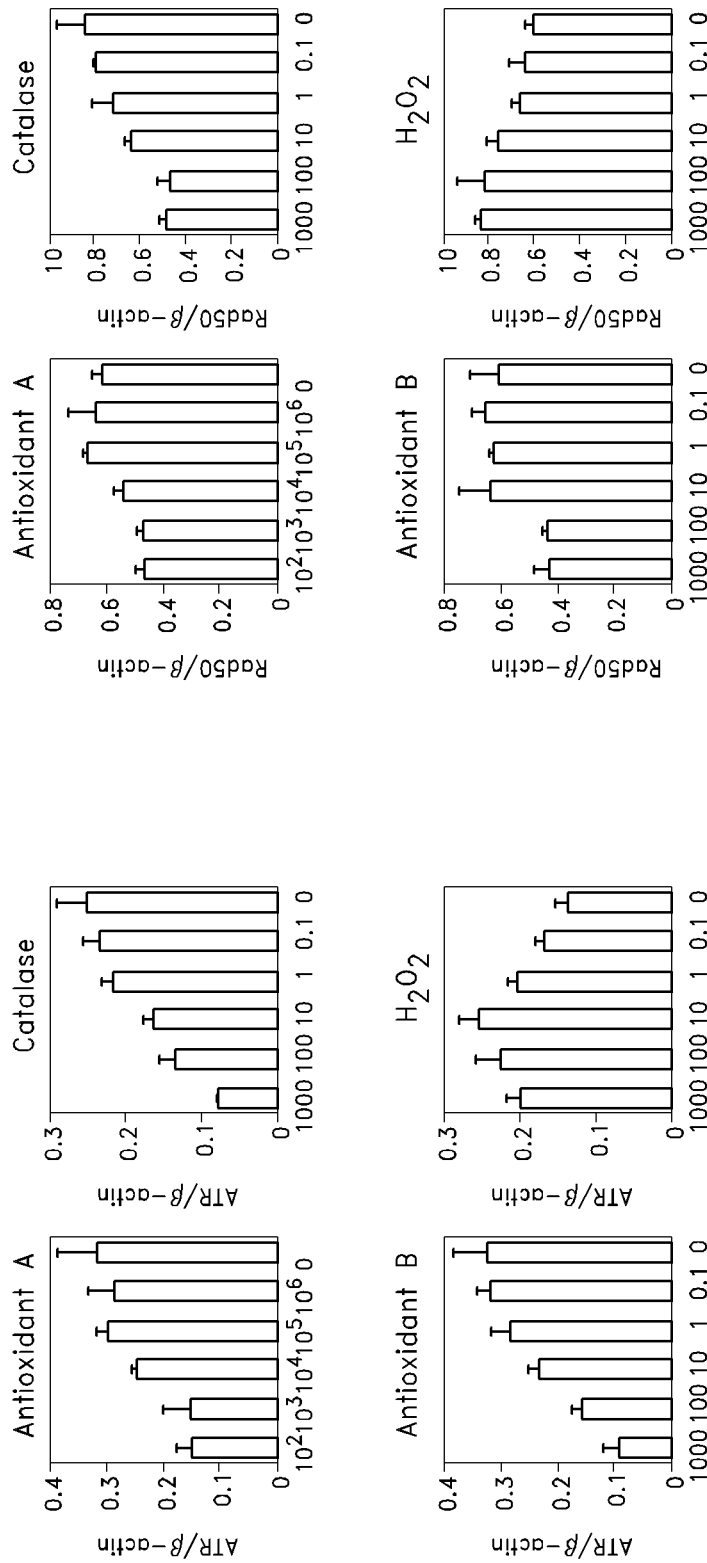
FIGS. 12A-12E depict semi-quantitative histograms of western blot data for the expression of ATR (FIG. 12A), Rad50 (FIG. 12B), Rad51 (FIG. 12C) Chk1 (FIG. 12D), and Chk2 (FIG. 12E).
Figures 12C, 12D:
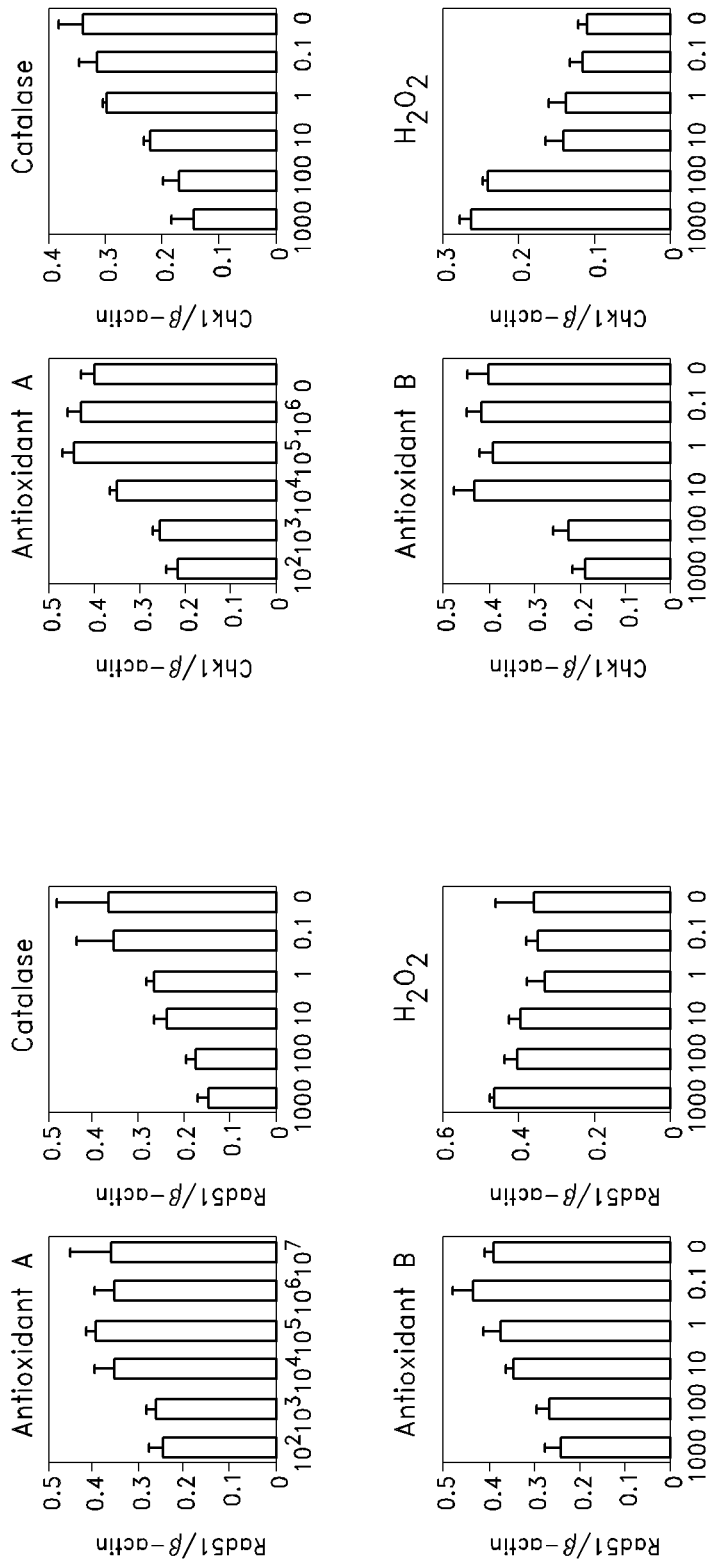
Figure 12E:
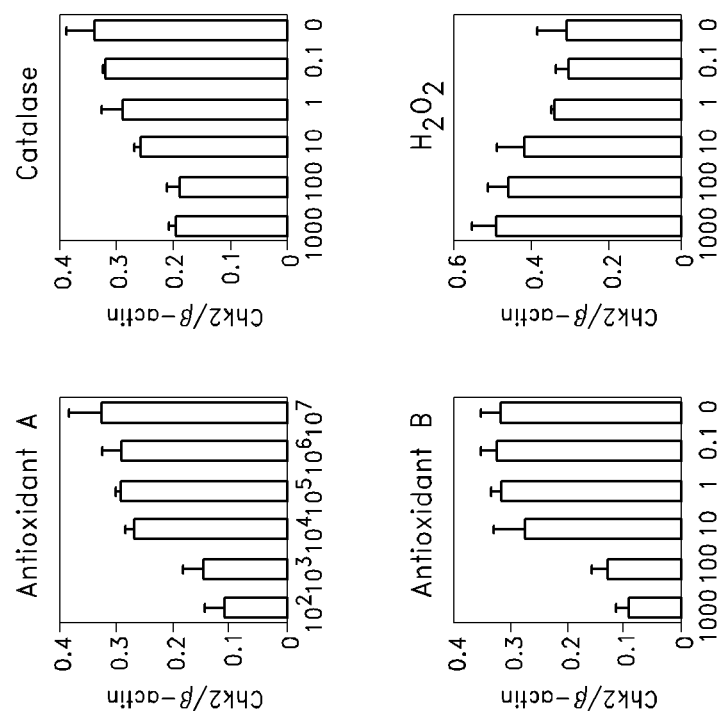

Various other DNA repair factors, including ATR and downstream factors Rad50, Rad51, Chk1, and Chk2, were also decreased by antioxidants (FIGS. 11 and 12), at the same concentrations that suppressed ROS levels significantly. As shown in FIG. 11, Panel A (antioxidant supplement), Panel B (custom antioxidant cocktail), Panel C (catalase), the expression levels of ATR, Rad50, Rad51, Chk-1, and Chk-2 were slightly or obviously decreased by high concentrations of catalase or antioxidants. In contrast, as shown in Panel D, expression levels were increased by high-dose H$_2$O$_2$. FIG. 12 shows representative quantitative histograms of the expression data from FIG. 11.

Figures 13A, 13B:
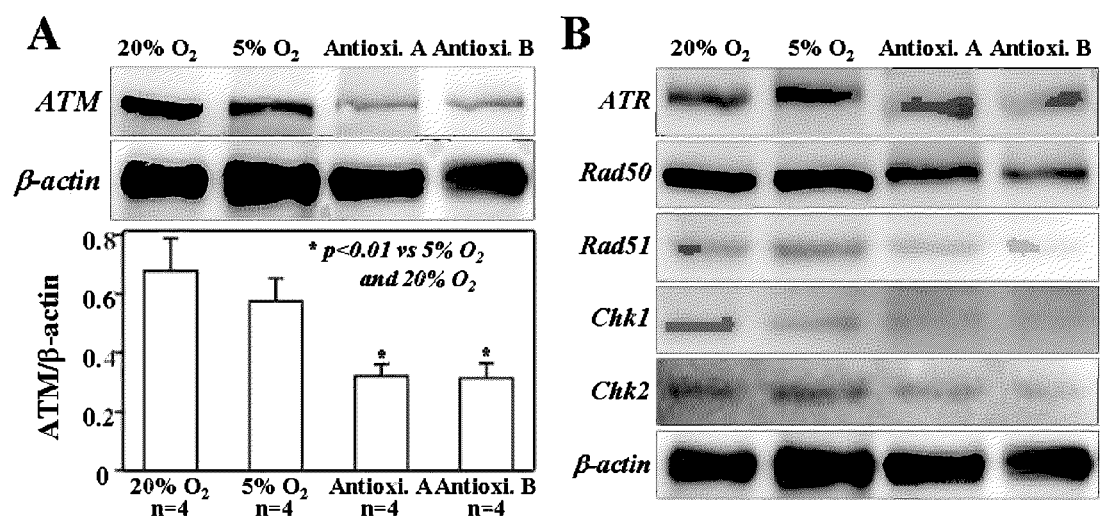
FIGS. 13A and 13B depict DNA repair data.

According to one embodiment of the invention, the expression levels of ATM and other DNA repair-related factors were down-regulated when ROS levels were decreased to "sub-physiological" levels at very high concentrations of antioxidants. In one embodiment, a low concentration of antioxidants drives ROS levels to an optimal "physiological" range, which reduces oxidative stress-induced DNA damage without impairing the DNA repair system. In one embodiment, given that ATM protein levels fell within 24 hours of exposure to antioxidants, physiological ROS levels concentrations may stabilize ATM and other DNA repair-related protein kinases, consistent with the notion that reductive stress induces intracellular protein aggregation. According to one embodiment, transcriptional downregulation plays an additional or supplemental role. In one embodiment, while ATM and related DNA repair factors may underlie the genomic instability seen with high antioxidants, the levels of these proteins do not change when CDCs are grown in certain conditions (FIG. 13). According to one embodiment, as shown in FIG. 13A, as compared to cells cultured under traditional 20% O$_2$, ATM expression did not significantly change in cells cultured under 5% O$_2$, but was significantly decreased by the addition of 1000-fold diluted antioxidant supplement (Antioxidant A) or 100 µM custom antioxidant cocktail (Antioxidant B). According to one embodiment, as shown in FIG. 13 B, expression of ATR, Rad50, Rad51, Chk1, and Chk2 did not significantly change in cells cultured under 5% O$_2$. However, according to some embodiments, many of these factors were decreased in cells cultured under traditional 20% O$_2$ with the addition of 1000-fold diluted antioxidant supplement (Antioxidant A) or 100 µM custom antioxidant cocktail (Antioxidant B).

According to several embodiments, the invention comprises compositions and methods to balance DNA injury during oxidative stress and faulty DNA repair in reductive stress.

Figure 14:
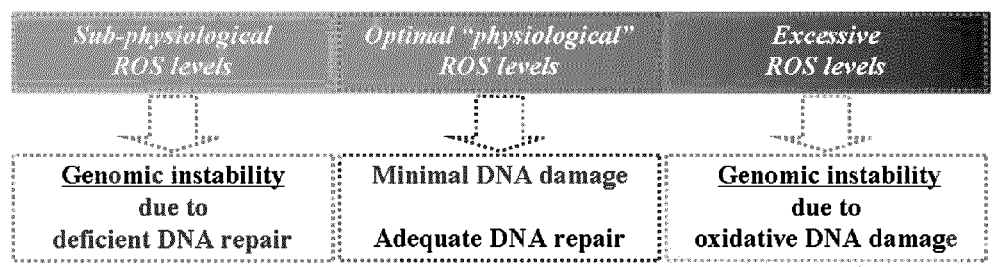
FIG. 14 depicts a schematic of the possible interactions between intracellular ROS levels and genomic stability.

According to several embodiments, a biphasic relationship between intracellular ROS levels and genomic stability in human cardiac and ES cells is provided. In one embodiment, a modest ROS suppression by culture in physiological oxygen (5%) decreases karyotypic abnormalities, but profound ROS suppression by antioxidant supplements paradoxically enhances genomic alterations. FIG. 14 depicts schematically, one possible model for such results. In one embodiment, oxidative stress induces DNA damage, accounting for the high frequency of karyotypic abnormalities in 20% $O_2$ culture (FIG. 14, right panels). On the other hand, excessive suppression of ROS to subphysiological levels down-regulates DNA repair pathways, thereby contributing to genomic instability (FIG. 14, left panels). Thus, according to one embodiment, optimal "physiological" levels of ROS are provided for activation of DNA repair pathways to maintain genomic stability in stem cells (FIG. 14, center panels). In one embodiment, excessive inhibition of ROS production leads to defective DNA repair and, thereby, increased frequency of karyotypic abnormalities seen with high antioxidants. In one embodiment, maintenance or enhancement of DNA repair pathways using the compositions disclosed herein contribute to the reduction in random (rather then systematic) chromosomal changes. In other embodiments, reduction of systematic chromosomal changes is achieved. In yet other embodiments, reduction in both random and systematic chromosomal changes is achieved.

According to some embodiments of the invention, CDCs derived from post-transplant patients are used. In one embodiment, such CDCs exhibit chromosomal abnormalities at a higher frequency than non-immunosuppressed patients. Thus, in several embodiments, the invention is particularly beneficial for reducing chromosomal damage in cells obtained from subjects with suppressed immune systems or other conditions that enhance karyotypic abnormalities.

Several embodiments of the invention are unexpected because free radicals are popularly viewed as harmful by-products of cell metabolism, and antioxidant dietary supplements, even at high doses, are touted to be beneficial in the prevention of cancer and a host of other diseases. In one embodiment, a balanced formulation comprising vitamin C, vitamin E, and glutathione prevents the extreme suppression of ROS by high-dose antioxidants which would otherwise increase DNA damage and genomic instability associated with down-regulation of DNA repair-related protein kinases. Several embodiments of the invention facilitate the dual role of ROS, in which a physiological level of ROS is aids in effective DNA repair, but high ROS induces DNA damage. In one embodiment, compositions or hypoxic conditions disclosed herein reduce the incidence of karyotypic abnormalities in cells by more than 10%, 25%, 50%, 75%, or 95% as compared to control cells.

Example 4

Effect of Physiologic Oxygen Concentrations on Stem Cell Proliferation

Figure 15:
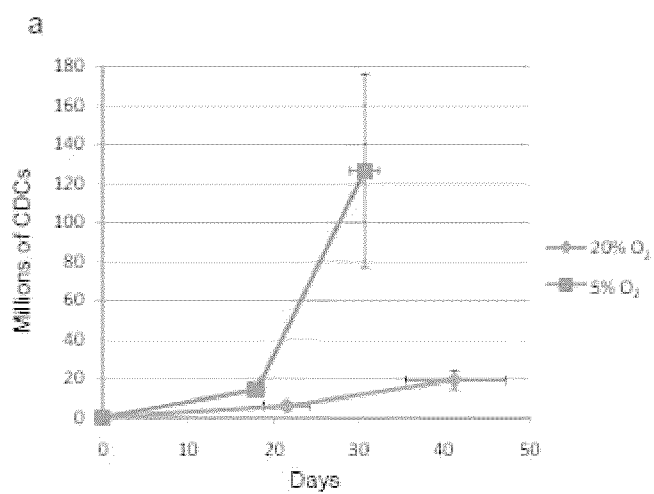
FIG. 15 depicts the difference in growth between culturing CDCs in 20% versus 5% $O_2$.

In order to determine other effects of that culturing in physiologic oxygen has, CDCs were generated in duplicate from 13 clinical biopsy samples. One portion of the tissue was used to generate cells which were cultured in room oxygen, while another portion was cultured in physiologic oxygen. The mean CDC yield for room oxygen cultures was 77.1±80.3 million from a mean starting mass of 263±185 mg of tissue. This yield was achieved in a mean time of 35.1±6.4 days. During the same average manufacturing time, mean CDC yield increased 3.2-fold for specimens cultured in physiologic oxygen. Moreover, the amount of starting material decreased 6.1-fold. The per mg yield was therefore 19.6-fold higher. To confirm these findings, parallel runs with the same amount of human starting tissue (~60 mg) were performed. Culture in physiologic oxygen conditions produced over six times more CDCs than room oxygen conditions (see FIG. 15).

In several embodiments, physiological oxygen concentrations also reduce the amount of time needed in culture to generate a given number of cells. Thus, in several embodiments, use of physiological oxygen concentrations is particularly advantageous because such conditions increase the overall yield of CDCs. In some embodiments, reduced quantities of starting cardiac tissue are required. In some embodiments, this is advantageous because a given sample has a greater capacity to produce CDCs, which increases the number of CDCs that are available for therapy and/or banking.

Figure 16:
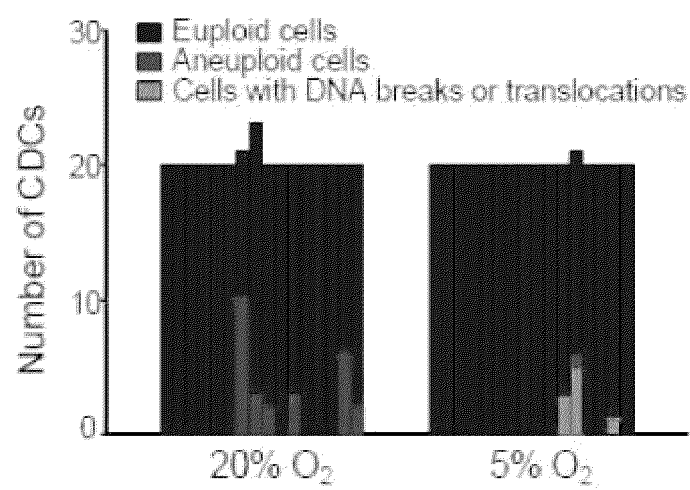
FIG. 16 depicts the number of euploid cells, aneuploid cells, and cells with DNA breaks or translocations for 13 CDC lines divided and cultured in 20% or 5% oxygen.

As discussed above, CDCs have been shown to occasionally acquire cytogenetic abnormalities, most frequently aneuploidy, during culture. In still additional embodiments, physiological oxygen concentrations also reduce decrease the incidence of one or more of aneuploidy, DNA breaks, base-pair mismatches, or translocations (see, e.g., FIGS. 1 and 16). Therefore, in several embodiments CDCs are cultured in physiologic oxygen to reduce cytogenetic abnormalities.

Example 5

In Vivo Efficacy of CDCs Grown in Physiologic Oxygen

Figure 17:
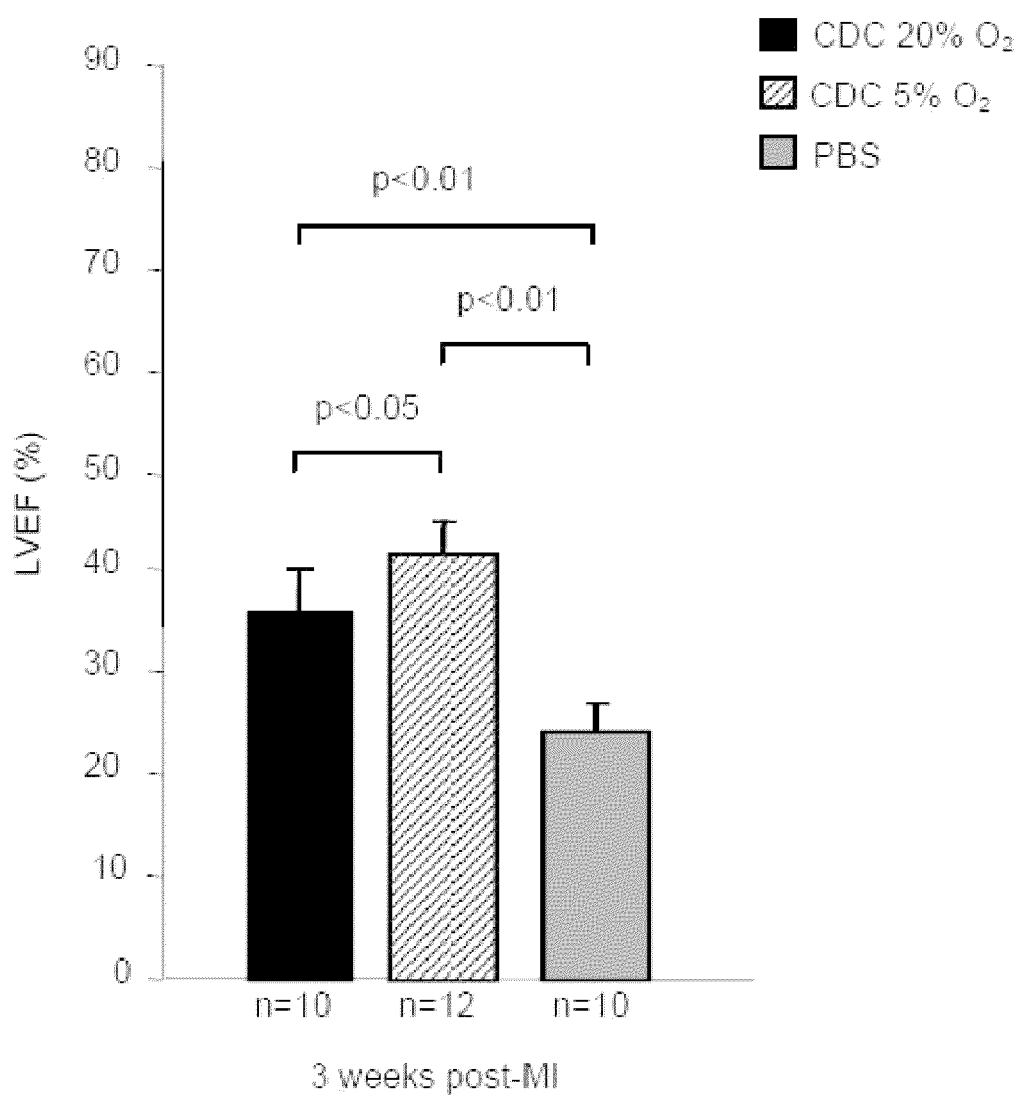
FIG. 17 depicts a significant improvement in the efficacy of CDCs cultured in physiologic oxygen concentrations as compared to those cultured in room oxygen.

As discussed above, culture conditions comprising physiological oxygen levels are used in some embodiments. The in vivo efficacy of CDCs cultured in physiologic oxygen was tested in comparison to CDCs cultured in room oxygen (20%). A mouse myocardial infarction model was used. In brief, myocardial infarction (MI) was created by ligation of the mid-left anterior descending coronary artery. Cells were delivered intramyocardially by direct injection at two peri-infarct sites immediately following ligation. CDCs (105) were injected in calcium-free PBS (5-7 µL at each site), with $10^5$ normal human dermal fibroblasts (NHDFs) or PBS as control. Cardiac function measured 3 weeks post-MI, indicated that CDCs grown in physiologic oxygen were yielded improved left ventricular ejection fraction (LVEF) as compared to CDCs grown in room oxygen (see FIG. 17). Both CDC-treated groups outperformed the PBS group. These data indicate that CDC potency is enhanced when culture is performed under physiologic oxygen conditions, as is done in several embodiments. In several embodiments, the potency of CDCs cultured in physiologic oxygen is increased in a statistically significant manner. In some embodiments, the potency of CDCs cultured in physiologic oxygen is increased by at least about 5%, about 10%, about 15%, about 20%, about 25% or greater.

Example 6

Expansion of Human Cardiac Stem Cells in Physiologic Oxygen Improves Cell Production, Efficiency, and Potency for Myocardial Repair Further to the discoveries detailed above, additional studies were conducted to obtain additional details regarding the impact of culturing human cardiac stem cells in physiologic concentrations of oxygen.

Expansion of cells in culture is the foundation for a wide variety of applications of adult stem cells and embryonic stem (ES) cells, including regenerative medicine and drug development. Chromosomal abnormalities are frequently found in stem cells after long-term culture and such chromosomal abnormalities may enhance carcinogenesis and impair functional potency, thereby complicating the therapeutic application of stem cells. Therefore, it is important to expand stem cells with fewer chromosomal abnormalities for clinical applications. Resident cardiac stem cells are considered to be particularly promising for myocardial regeneration, as they mediate cardiogenesis and angiogenesis. In several embodiments, the methods and compositions disclosed herein allow the expansion of a relatively small number of cells into a larger population (e.g., tens of millions of cells in some embodiments) of cardiac stem cells and supporting cells (collectively termed CDCs) using ex vivo culture. As discussed above, in some embodiments, the initial sample of cardiac tissue is from a minimally invasive human heart biopsy. In other embodiments, other tissue sources are used (e.g., surgically obtained cardiac tissue, donor cardiac tissue, etc.). While clinical application of CDCs is presently under way in the CADUCEUS (CArdiosphere-Derived aUtologous Stem CElls to Reverse ventricUlar dySfunction, ClinicalTrials.gov. Identifier NCT00893360) trial, karyotyping revealed that approximately one-third of preliminary CDC production runs included cytogenetically abnormal cells, most often due to changes in chromosome number (aneuploidy; see e.g., FIG. 1).

As discussed above, ex vivo expansion of stem cells, including CDCs, is generally performed by incubating cells in incubators equilibrated with 95% air and 5% $CO_2$ (~20% $O_2$). However, the oxygen concentration of the in vivo microenvironment of stem cells in biological tissues is often much lower, ranging from about 1% to about 8%, (depending on the tissue). As a result, stem cells for use in a tissue having a low oxygen microenvironment in vivo may suffer from oxidative stress under such conventional culture conditions. Given that oxidative stress may play a role in DNA damage and genomic instability, the present study investigated the effects of ex vivo expansion of human cardiac stem cells in 'hypoxic' conditions (mimicking the low oxygen tensions operative in vivo)

Ex Vivo Expansion of Human Cardiac Stem Cells Under Low Oxygen

Adult human cardiac stem cells were expanded using similar methods as described above. Briefly, endomyocardial heart tissue biopsies (~10 mg) were obtained from patients during clinically indicated procedures after informed consent, in an Institutional Review Board-approved protocol. As discussed above, in some embodiments, non-biopsy tissue sources are used. All investigations conform to the Declaration of Helsinki. Biopsies were minced into small fragments and digested with 0.2 mg/mL of collagenase for 30 min. The digested tissue fragments were then equally divided and moved to two 6 cm diameter culture dishes coated with 20 mg/mL of fibronectin (BD Biosciences) and randomly selected to culture as 'explants' in a typical $CO_2$ incubator (20% $O_2$) or a incubator with physiological low oxygen (5% $O_2$). Following cardiosphere formation, CDCs were grown and expanded by passaging under 20% $O_2$ (20% $O_2$ CDCs) or 5% $O_2$ (5% $O_2$ CDCs), respectively. IMDM basic medium (Gibco) supplemented with 10% FBS (Hyclone) and 20 mg/mL gentamycin was used for all cultures. Twice-passaged CDCs (1-2 months culture from the date of tissue biopsy) were used for experiments unless otherwise indicated.

Karyotype Analysis

CDCs were seeded onto fibronectin-coated 25 $cm^2$ tissue culture flasks ($10^4$ cells/$cm^2$) and continuously cultured under 5% $O_2$ or 20% $O_2$, respectively. The karyotyping data in this example are extended from those discussed above. After ~24 h of incubation, cells were treated with 0.1 mg/mL of colcemid (Invitrogen) for 4 h. Then the cells were trypsinized, treated with hypotonic solution, and fixed. Metaphases were spread on microscope slides, and karyotype analysis was done using a well-established G banding technique. The chromosomes were classified according to the International System for Human Cytogenetic Nomenclature. At least 20 metaphases were analyzed per cell sample. Notably, all but one of the patients whose samples underwent karyotypic analysis were immunosuppressed heart transplant recipients. Cytogenetic abnormalities may have been more frequent in the immunosuppressed heart transplant patient population which predominated in the samples studied, as immunosuppressed post-transplant patients may be predisposed to lymphomas with clonal chromosomal abnormalities. Notably, in the immunocompetent population studied in CADUCEUS, only 1 of 13 clinical-production samples to date has been abnormal by cytogenetic screening (unpublished results). However, based on the reduction of chromosomal abnormalities in 5% $O_2$ culture according to several embodiments, disclosed herein, cytogenetic screening may no longer be required as a clinical-grade product release criterion. In some embodiments, reduction in chromosomal abnormalities due to culturing in physiological oxygen concentrations results, regardless of the immune status of the subject from whom the original tissue samples were collected. Advantageously, this broadens the scope of individuals who can serve as tissue donors for generation of cardiac stem cells. In some embodiments, an immunocompromised transplant patient can serve as a donor for cells for use in autologous therapy (e.g., expanded cells to be administered to that patient) or even for allogeneic therapy.

Flow Cytometry

To investigate how physiological low-oxygen culture affects the subpopulation of c-kit+ stem cells and the expression of p16INK4A, a marker for cell senescence, CDCs expanded in 5% $O_2$ and 20% $O_2$ were harvested as single-cell suspensions using trypsin digestion. Cells were then incubated with PE-conjugated mouse anti-human c-kit antibody (eBioscience) or mouse anti-human p16INK4A antibody (BD Biosciences) for 60 min. The expressions of c-kit and p16INK4A were quantitatively measured using a FACS Calibur flow cytometer with CellQuest software (BD Biosciences).

Immunostaining

To determine the myogenic differentiation in vitro, CDCs were seeded on fibronectin-coated four-chamber culture slides and continuously cultured in 5% $O_2$ or 20% $O_2$. After 3 days of culture, cells were fixed, blocked with goat serum for 30 min, and then incubated with mouse anti-human troponin T antibody (R&D Systems Inc.) for 1 h at room temperature. Culture slides were washed and then incubated with a PE-conjugated secondary antibody. Cell nuclei were stained with DAPI. Myogenic differentiation was quantified by calculating the positive-stained area using the Image-Pro Plus software (version 5.1.2, Media Cybernetics Inc., Carlsbad, Calif., USA).

The telomerase activity and DNA damage in CDCs were also estimated by immunostaining with mouse anti-human telomerase catalytic subunit (TERT) antibody (Lifespan Bioscience) or rabbit polyclonal antibody against γ-$H_2AX$ (phosphor S139, Abcam Inc.), as described above. Positively stained cells were counted by fluorescence microscopy.

Senescence-Associated Beta-Galactosidase Staining

Third-passage CDCs were seeded on fibronectin-coated four-chamber culture slides and continuously cultured in 5% $O_2$ or 20% $O_2$. After 3 days of culture, senescence-associated beta-galactosidase (SA-β-Gal) was performed according to established techniques. The SA-β-Gal-positive cells were counted under a microscope.

TUNEL Assay

To quantify the resistance to oxidative stress in vitro, CDCs were seeded on fibronectin-coated four-chamber culture slides and continuously cultured in 5% $O_2$ or 20% $O_2$. After 2 days of culture, cells were moved into a general incubator (20% $O_2$), and cultured with or without the addition of 100 mM $H_2O_2$ in the medium for another 24 h. Cells were fixed, and apoptotic cells were detected by TUNEL assay (Roche Diagnostics, Mannheim, Germany), according to the manufacturer's instructions. Cell nuclei were stained with DAPI, and TUNEL-positive cells were counted under fluorescence microscopy.

Measurement of Intracellular Reactive Oxygen Species

To measure intracellular reactive oxygen species (ROS), CDCs were seeded in 6- or 96-well plates coated with 20 mg/mL of fibronectin and continuously cultured in 5% $O_2$ or 20% $O_2$. At ~90% confluence, cells were incubated with 10 mM 2',7'-dichlorodihydrofluorescein diacetate (DCF; Invitrogen) for 60 min. The fluorescence of 2', 7'-dichlorodihydrofluorescein in cells cultured in 96-well plates is directly determined using SpectraMax M5 (Molecular Devices Corp.) with an excitation wavelength of 495 nm and an emission wavelength of 520 nm. Cells cultured in six-well plates were trypsin-treated and fixed. The DCF fluorescence intensity in cells was analysed by flow cytometry as described above.

Western Blotting

Western blot analysis was performed to compare the expressions of integrin-$α_2$, laminin-$β_1$, and c-Myc in CDCs cultured under 5% $O_2$ and 20% $O_2$. The equivalent of 30 mg of total protein was loaded onto SDS-PAGE gels, and then transferred to PVDF membranes. After overnight blocking, membranes were incubated with mouse anti-human integrin-$α_2$ antibody, mouse anti-human laminin-$β_1$ antibody, rabbit anti-β-actin monoclonal antibody (Lifespan Bioscience), or mouse anti-human c-Myc antibody (BD Biosciences). The appropriate horseradish peroxidase-conjugated secondary antibodies were used, and then the blots were visualized by using SuperSignal West Femto maximum sensitivity substrate (Thermo Scientific) and exposed to Gel Doc™ XR System (Bio-Rad Lab. Inc.). Quantitative analysis for blots was done by Quantity One software, and expressions were normalized by b-actin.

ELISA

To compare the potency of the productions of growth factors, CDCs expanded under 5% $O_2$ or 20% $O_2$ were seeded in 24-well culture plates at a density of $1×10^5$ mL and incubated for 3 days with hypoxic stimulation (under 1% $O_2$ to mimic the microenvironment of the ischemic heart). The supernatants were collected and the concentrations of Angiopoietin-2, bFGF, HGF, IGF-1, SDF-1, and VEGF were measured with human ELISA kits (R&D Systems Inc.), according to the manufacturer's instructions.

In vitro Angiogenesis Assay

Angiogenic potency was estimated by tube formation using an in vitro angiogenesis assay kit (Chemicon Int.), according to the manufacturer's instructions. Briefly, CDCs expanded under 5% $O_2$ or 20% $O_2$ were seeded on ECMatrix™-coated 96-well plates at a density of $2×10^4$ cells per well. After 6 h incubation with hypoxic stimulation (under 1% $O_2$ to mimic the microenvironment of ischemic heart), tube formation were imaged. The total tube length was then measured with Image-Pro Plus software.

Myocardial Infarction Model and Cell Implantation

An acute myocardial infarction was created in adult male SCID-beige mice (10-12 weeks old), as described above. The study was approved by the Institutional Animal Care and Use Committee of Cedars-Sinai Medical Center and conformed to the Guide for the Care and Use of Laboratory Animals published by the US National Institutes of Health (NIH Publication No. 85-23, revised 1996). Briefly, after general anaesthesia and tracheal intubation, mice were artificially ventilated with room air. A left thoracotomy was performed through the fourth intercostal space and the left anterior descending artery was ligated with 9-0 prolene under direct vision. The mice were then randomized and subjected to intramyocardial injections with a 30 G needle at four points in the infarct border zone with 40 mL of PBS (PBS group, n=10), $1×10^5$ CDCs expanded under 20% $O_2$ (20% $O_2$ CDCs, n=10), or $1×10^5$ CDCs expanded under 5% $O_2$ (5% $O_2$ CDCs, n=12).

Quantification of Engraftment by Real-Time PCR

Quantitative PCR was performed 24 h and 7 days after cell injection in six to seven animals from each cell-injected group to quantify cell retention/engraftment. Male human CDCs were injected to enable detection of the SRY gene located on the Y chromosome. The whole mouse heart was harvested, weighed, and homogenized. The TaqMan assay was used to quantify the number of transplanted cells with the human SRY gene as template (Applied Biosystems, CA, USA). A standard curve was generated with multiple dilutions of genomic DNA isolated from the injected CDCs to quantify the absolute gene copy numbers. All samples were spiked with equal amounts of genomic DNA from non-injected mouse hearts as control. For each reaction, 50 ng of genomic DNA was used. Real-time PCR was performed with an Applied Biosystems 7900 HT Fast real-time PCR machine. Experiments were performed in triplicate. The number of engrafted cells per heart was quantified by calculating the copy number of SRY gene in the total amount of DNA based on the standard curve.

Echocardiography

Mice underwent echocardiography at 3 h (baseline) and 3 weeks after surgery using Vevo 770™ Imaging System (VISUALSONICS™, Toronto, Canada). After the induction of light general anaesthesia, the hearts were imaged two-dimensionally (2D) in long-axis views at the level of the greatest LV diameter. LV end diastolic volume, LV end systolic volume, and LV ejection fraction (LVEF) were measured with VisualSonics V1.3.8 software from 2D long-axis views taken through the infarcted area.

Histology

Mice were sacrificed 3 weeks after treatment. Hearts were sectioned in 5 mm slices and fixed with 4% paraformaldehyde. The engraftment of implanted human CDCs was identified by immunostaining with antihuman nuclear antigen (HNA) antibody (Chemicon). To measure cell engraftment, 10 images of the infarction and border zones were selected randomly from each animal (three sections/animal; 1 mm separation between sections; 20× magnification, Eclipse TE2000-U). The percentages of human nuclei per total nuclei were quantified using Image-Pro Plus software (version 5.1.2, Media Cybernetics Inc.), and the average value from each heart was used for statistical analysis.24 The differentiation of cardiac stem cells into myocytes, smooth muscle cells, and endothelial cells was identified by immunostaining with monoclonal antibodies against human-specific a-sarcomeric actin, smooth muscle actin, and von Willebrand factor (vWF) (Sigma), respectively, as described above. Masson's trichrome staining was also performed to examine the infarction size, LV wall thickness, LV chamber area, and viable myocardium, as described previously.

Statistical Analysis

All results are presented as mean±SD. Statistical significance between two groups was determined using the two-tailed paired t-test and among groups by ANOVA followed by Bonferroni post hoc test (SPSS II, Chicago, Ill., USA), unless otherwise indicated. Differences were considered statistically significant when P<0.05.

Results

Cell Production

Figures 18A, 18B, 18C, 18D:
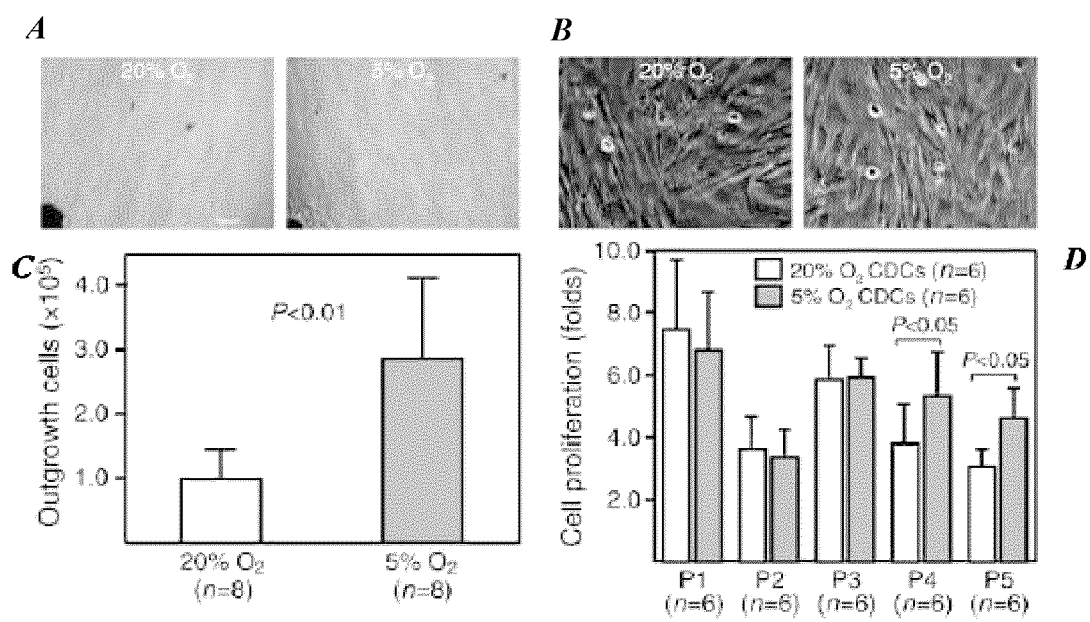
FIGS. 18A-18D depict the growth and proliferation of cardiac stem cells in 5% $O_2$ and 20% $O_2$. Panel A shows representative images showing that cell outgrowth from 'explants' (red arrow) was much faster in 5% $O_2$ (right) than in 20% $O_2$ (left). The number of cells harvested (Panel C) was more than two-fold higher in 5% $O_2$ than in 20% $O_2$, although the amount of starting material was equivalent. Panel B depicts CDCs at earlier passages (shown in passage #2) showing no differences in either morphology or proliferative activity (Panel D) under 5% $O_2$ and 20% $O_2$, although greater proliferation was observed in cells expanded under 5% $O_2$ at later passages.

Compared with culture in 20% $O_2$, the outgrowth of cells from the 'explants' was faster in 5% $O_2$, resulting in more than two-fold higher yield of outgrowth cells (P, 0.001, FIG. 18A). The proliferation of CDCs was similar at subsequent early passages, although proliferation at later passages was higher in CDCs expanded in 5% $O_2$ (P<0.05, FIG. 18B). In several embodiments, the increased proliferation is due to induction of HIF-1α (or other hypoxia-mediated factors) and subsequent adaptation of the cells to the reduced oxygen. In some embodiments, 5% $O_2$ culture conditions increases cell migration out from the 'explants' through the induction of HIF-1α (or other hypoxia-mediated factors). Interestingly, the degree of hypoxia in 5% $O_2$ culture was insufficient to increase the concentrations of certain chemokines and cytokines in the media, including VEGF and SDF-1, (data not shown). Thus, in some embodiments, increased proliferation of cardiac stem cells occurs in a migratory-independent fashion (e.g., in the absence of HIF-1α (or other hypoxia-mediated factors such as VEGF or SDF-1). In several embodiments, increased proliferation is due to hypoxia induced increases in cell cycle entry, or reduced apoptosis, or a combination of these mechanisms (and/or in combination with other mechanisms disclosed herein).

Other studies have suggested that culturing cells in physiological low-oxygen culture increases the 'stemness' of cells, for example embryonic stem cells. However, according to the presently disclosed methods and compositions, the c-kit+ subpopulation and differentiation potency were not augmented in these twice-passaged CDCs expanded in 5% $O_2$ relative to 20% $O_2$. Furthermore, the expression levels of integrin-$α_2$, laminin-$β_1$, and c-Myc were also comparable in the two conditions. Thus, in some embodiments, cardiac stem cells respond in a different way to physiologic oxygen concentrations as compared to other types of stem cells. These differences likely reflect differences in the responses of specific cell types to hypoxia. In some embodiments, such differences are advantageous, the differential responses of different cell types are used to optimize the reproduction (e.g., expansion), viability, engraftment, and/or functional effect of a population of cells to be administered to a certain patient. For example, different degrees of hypoxia (e.g., a sliding scale of oxygen concentrations) impact cardiac stem cells differently, in some embodiments. In some embodiments, cardiac stem cells isolated from highly oxygenated regions of the cardiac tissue respond differently to oxygen concentrations that differ from their in vivo micro-environment. As a non-limiting example, a cardiac stem cell that originated from cardiac tissue exposed to a 5% concentration of oxygen in vivo was exposed to a 3% concentration in culture, the resultant expanded population may proliferate slightly less, but provide more efficient engraftment as compared to the same cells cultured in 5% oxygen.

Chromosomal Abnormalities

Figures 19A, 19B:
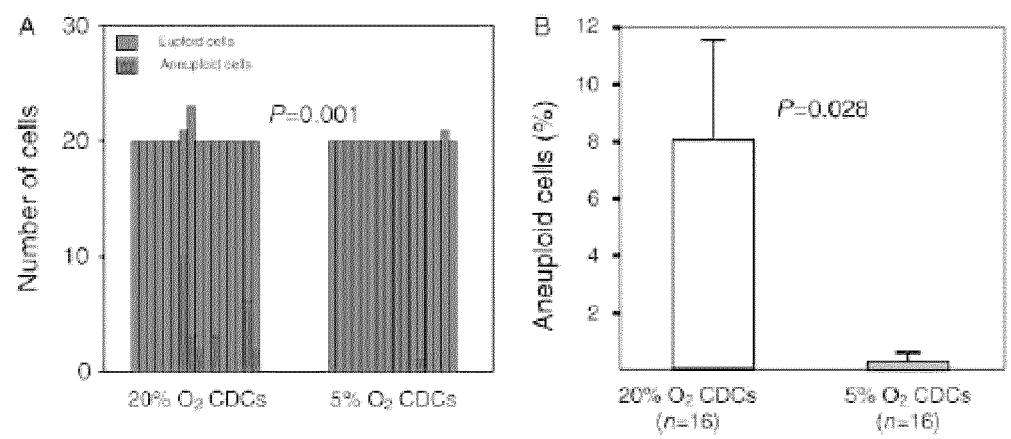
FIGS. 19A-19B depicts analysis of chromosomal abnormalities. Panel A indicates fewer aneuploid cells in CDCs cultures expanded in 5% $O_2$ as compared to 20% $O_2$. Panel B shows that the percentages of aneuploid cells were also decreased in 5% $O_2$ culture.
Figure 24:
FIG. 24 depicts a representative karyotype showing aneuploidy (in this case, trisomy 8) in twice-passaged cardiac-derived cells expanded under 20% $O_2$.
Figures 26A, 26B, 26C, 26D:
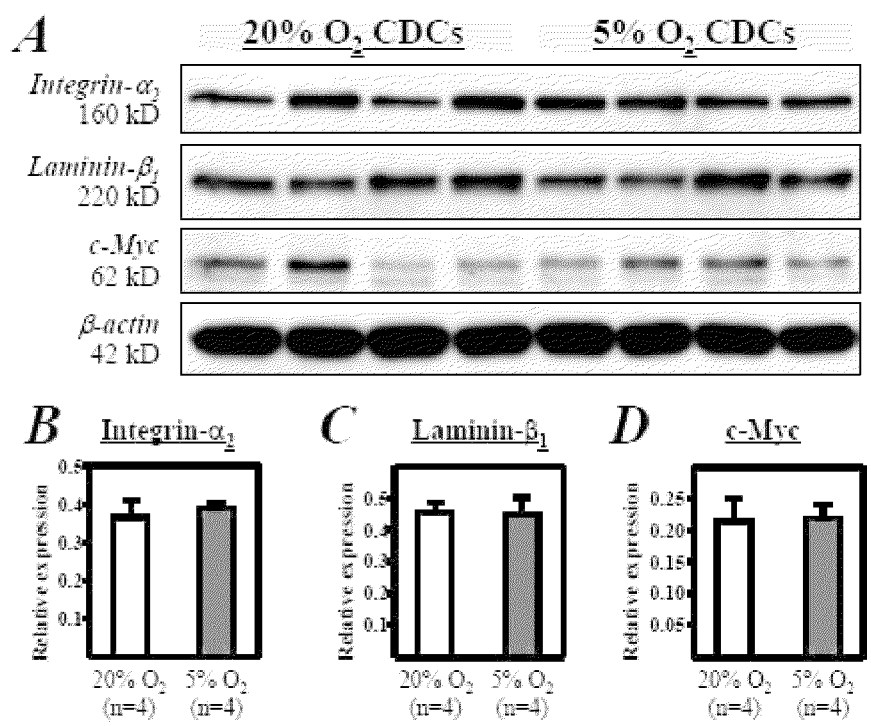
FIGS. 26A-26D depict analysis of the expression of adhesion molecules and c-Myc (panel A shows Western blot protein expression data). There is no significant difference in the expression levels of integrin-$\alpha_2$ (panel B), laminin-$\beta_1$ (panel C), or c-Myc (panel D) in cardiac-derived cells expanded in 5% $O_2$ versus 20% $O_2$.
Figures 27A, 27B, 27C, 27D, 27E, 27F:
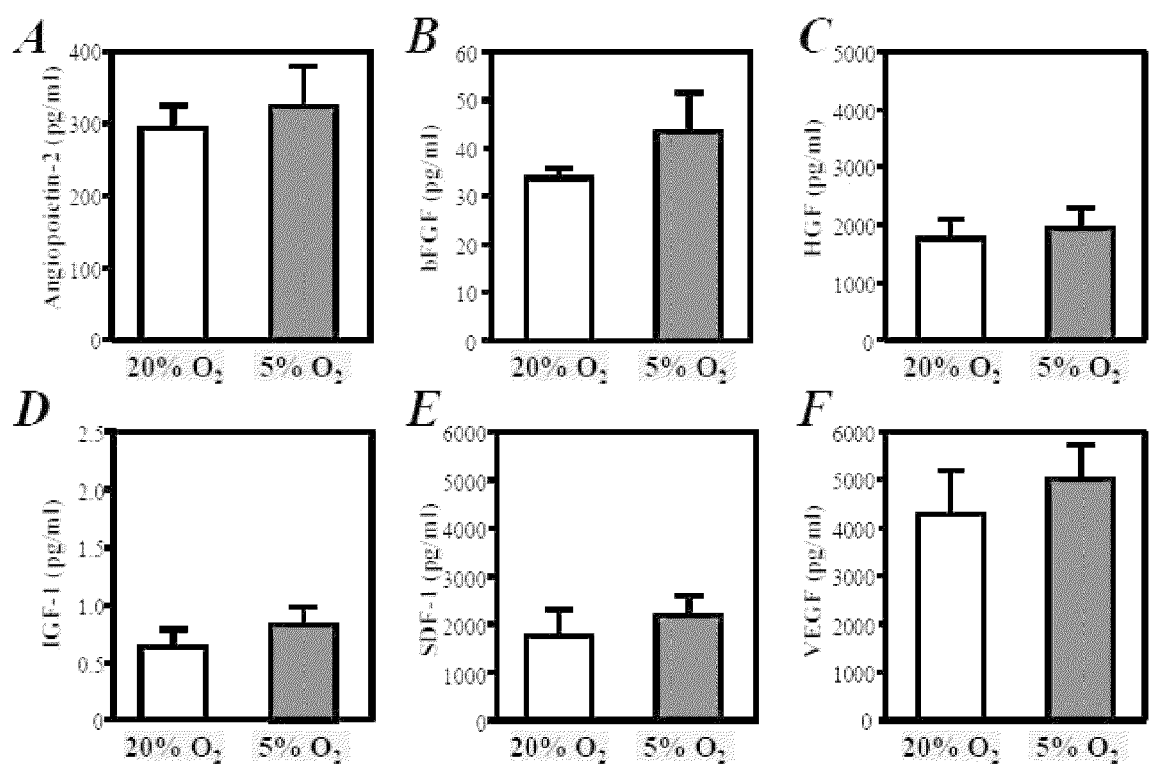
FIGS. 27A-27F depict a comparison of in vitro production of growth factors between cardiac-derived cells expanded in 5% $O_2$ and 20% $O_2$. The concentrations of angiopoietin-2 (panel A), bFGF (panel B), HGF (panel C), IGF-1 (panel D), SDF-1 (panel E), and VEGF (panel F) measured by ELISA showed no significant difference in conditioned medium culture with hypoxic stimulation.

Consistent with the preliminary karyotyping data discussed above, 6 of 16 (37.5%) CDC samples expanded in 20% $O_2$ included aneuploid cells (26 of 323 examined cells, FIG. 19A). The most common changes were trisomy 8 (FIG. 24) and Y chromosome loss. In contrast, in 16 CDC samples expanded under 5% $O_2$, there was only one aneuploid cell (from a total of 321 examined cells; P<0.01 by $χ^2$ test, FIG. 19A). The aneuploidy here reflected loss of the Y chromosome, an innocuous cytogenetic abnormality. These differences in genomic stability cannot be due to differences in the source tissue, as the same biopsies were subdivided and cultured in parallel to facilitate direct comparison. The percentages of aneuploid cells were also lower in CDCs expanded under 5% $O_2$ than in 20% $O_2$ (P=0.028 by unpaired t-test, FIG. 19B). Thus, in several embodiments, ex vivo expansion of human cardiac stem cells under physiological low oxygen conditions (e.g., about 5% $O_2$) reduces the incidence of chromosomal abnormalities. In several embodiments, oxygen concentrations are tailored specifically to the region of tissue from which the original cardiac cells were collected and subsequently expanded. For example, if cells were collected from the interior wall of the heart, which is frequently exposed to oxygenated blood, an oxygen concentration that mimics this in vivo environment may be used to culture cardiac stem cells collected from this region. In other embodiments, cells are collected from a surgical sample, in particular from within the myocardial wall, a lower oxygen concentration may be used during several embodiments, of the expansion protocol. In several embodiments, oxygen concentrations are tailored specifically to the region of tissue to be treated. For example, if a subject has damaged cardiac tissue on the interior wall of the heart, which is frequently exposed to oxygenated blood, a first oxygen concentration may be used to culture cardiac stem cells to treat this region. In other embodiments, if damaged tissue is within the myocardial wall, a lower oxygen concentration may be used.

Phenotype and In Vitro Myogenic Differentiation

The subpopulation of c-kit+ stem cells was comparable in CDCs expanded in 5% $O_2$ and in 20% $O_2$ (P=0.106 FIGS. 25A and 25C). Likewise, the propensity for cardiomyogenic differentiation, by immunostaining for human-specific cardiac troponin T, was equivalent in the two conditions (FIGS. 25B and 25D). Thus, in some embodiments, the use of physiological oxygen concentrations does not alter the "stemness" profile of the cultured cells, at least with regard to expression of certain markers (e.g., c-kit). In other embodiments, however, alterations in stem cell marker profiles result from alterations in oxygen concentration. As such, in some embodiments, the profile of the resultant cells may be controlled at least in part by the oxygen concentration used in the culturing process.

Cell Senescence

Cell senescence was evaluated by the expression of $p16^{INK4A}$, telomerase activity, and SA-β-Gal staining. The expression of $p16^{INK4A}$ was lower (FIGS. 20A and 20D, P<0.001), and the telomerase activity (evaluated by the expression of TERT) was higher (FIGS. 20B and 20E, P<0.01) in CDCs expanded in 5% $O_2$. The fraction of SA-β-Gal-positive cells was also lower in third-passage CDCs expanded in 5% $O_2$ than in 20% $O_2$ (FIGS. 20C and 20F, P<0.05). Thus, in some embodiments, the culture conditions and methods disclosed herein reduce the "aging" rate of cultured cells. In some embodiments, this is realized as a decrease in expression in one or more genes (or proteins) related to the aging of a cell, cell cycle entry (or activity), tumor suppressor genes, and the like. Moreover, in some embodiments, karyotypic abnormalities and/or aging of cells is reduced by virtue of increase telomerase activity (e.g., reduced telomere shortening).

Intracellular ROS, DNA Damage, and Resistance to Oxidative Stress

Figure 21A:
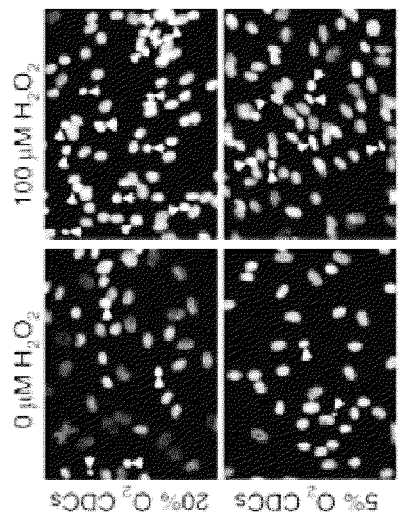
FIGS. 21A-21F depict analysis of intracellular ROS, DNA damage, and resistance to oxidative stress. Panel A shows that the levels of intracellular ROS are lower in CDCs expanded in 5% $O_2$ when compared with those in 20% $O_2$. Panel C depicts DNA damage as evidenced by the formation of γ-$H_2$AX foci. DNA damage was lower in CDCs expanded in 5% $O_2$ than in 20% $O_2$ (Panel D). Panel E shows representative images of TUNEL-positive (red) CDCs after 24 h exposure to 100 mM $H_2O_2$. The number of apoptotic cells (panel F) was lower in CDCs expanded in 5% $O_2$ than 20% $O_2$.
Figure 21B:
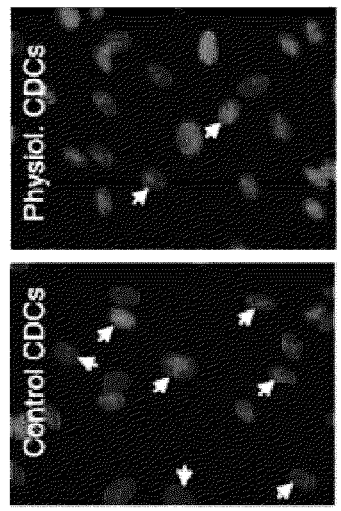
Figure 21C:
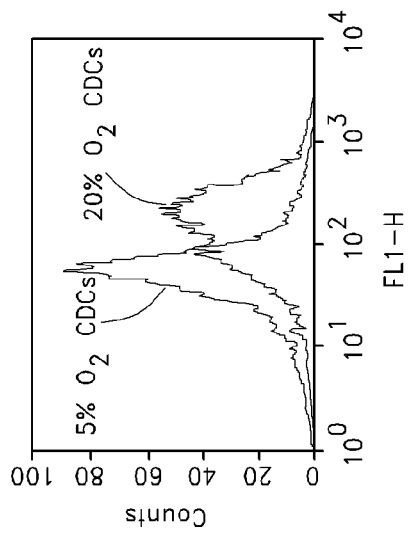
Figure 21D:
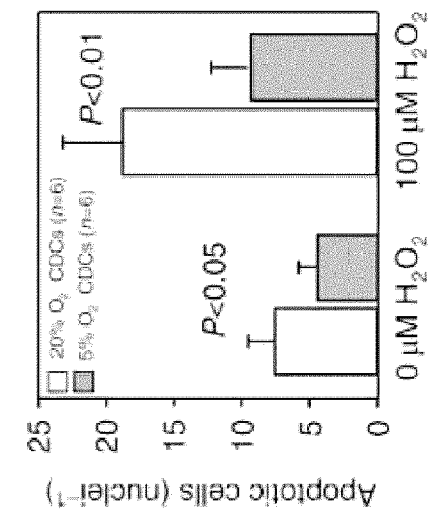

Intracellular ROS concentrations were measured by DCF staining. Intracellular ROS level was lower in 5% $O_2$-cultured CDCs than in 20% $O_2$-cultured CDCs (FIGS. 21A and 21B; P<0.01). The percentage of cells with γ-$H_2$AX foci, a marker of DNA damage was likewise lower in 5% $O_2$-cultured CDCs (FIGS. 21C and 21D; P<0.01). This correlates with the karyotyping data discussed above, which showed a dramatic reduction of aneuploidy in CDCs expanded under 5% $O_2$ (see e.g., FIG. 19). Thus, in several embodiments, the culturing methods and compositions disclosed herein reduce the level of intracellular ROS, which in turn, reduces the incidence of karyotypic abnormalities. In some embodiments, the decrease in ROS also increases cellular viability. In some embodiments, increased viability is manifest by increased proliferation in culture, increased viability after in vivo administration, and/or improved engraftment after in vivo administration.

Figure 21E:
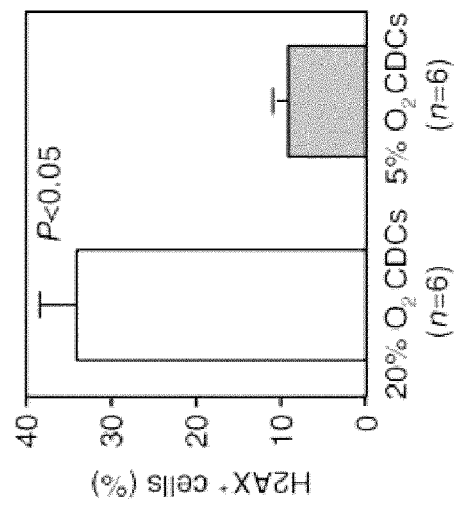
Figure 21F:
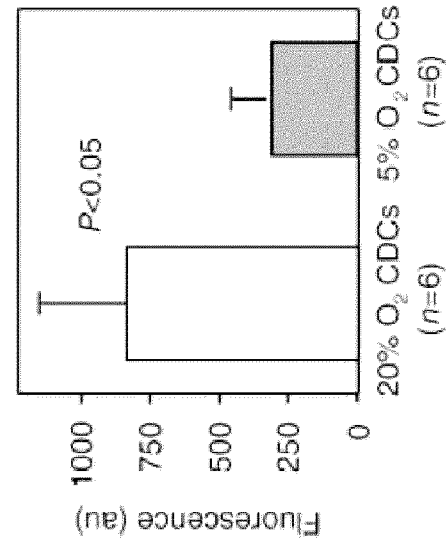

In order to determine whether cells cultured in physiological $O_2$ were more resistant (or more sensitive), to oxidative stress, CDCs were therefore exposed to $H_2O_2$, a powerful oxidant. After 24 h of exposure to 100 mM $H_2O_2$, the number of apoptotic cells was lower in 5% $O_2$ CDCs than in those grown in 20% $O_2$ (FIGS. 21E and 21F, P<0.01). The basal frequency of apoptosis was also lower in the 5% $O_2$ CDCs (P<0.05). Thus, in some embodiments, not only do the disclosed culture methods and compositions reduce formation of ROS that naturally appear, but they reduce the sensitivity of cells to sources of oxidative stress. In some embodiments, as a result, cells are more robust in a wider variety of environments in vivo, and thus, have greater viability.

Expression of Adhesion Molecules and c-Myc

The expression levels of integrin-$\alpha_2$, laminin-$\beta_1$, and c-Myc were comparable in CDCs expanded in 5% $O_2$ and in 20% $O_2$ (see FIGS. 26A-26D).

In Vitro Production of Growth Factors and Tube Formation

While CDCs are known to secrete a variety of growth factors the present study analysed conditioned media to determine whether hypoxic culture influences the paracrine secretion of selected growth factors by CDCs. Cells cultured either in 5% $O_2$ or 20% $O_2$ were plated in fresh media and grown for 3 days with hypoxic stimulation (1% $O_2$) to mimic the microenvironment of ischemic heart. The production of the majority of growth factors under hypoxic stimulation, including angiopoietin-2, bFGF, HGF, IGF-1, SDF-1, and VEGF, was comparable in CDCs expanded under 5% $O_2$ or 20% $O_2$ (see FIGS. 27A-27F), although some factors tended to be higher in CDCs expanded under 5% $O_2$.

Figures 28A, 28B:
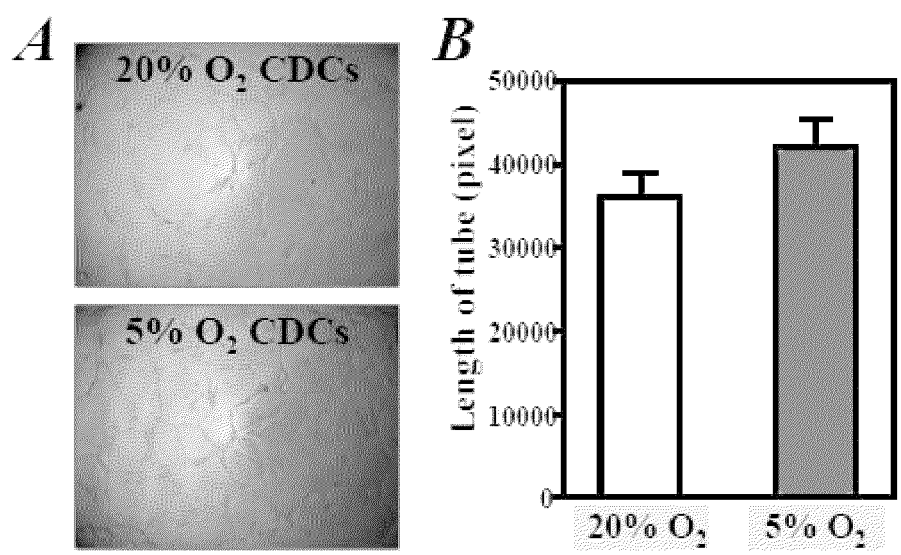
FIGS. 28A-28B depict an in vitro angiogenesis assay. Panel A shows the formation of capillary-like tubes in extracellular matrix from cardiac-derived cells expanded in 5% $O_2$ and 20% $O_2$ did not differ due to hypoxic stimulation. Panel B shows the quantitative summary data for tube length.
Figures 29A, 29B, 29C, 29D:
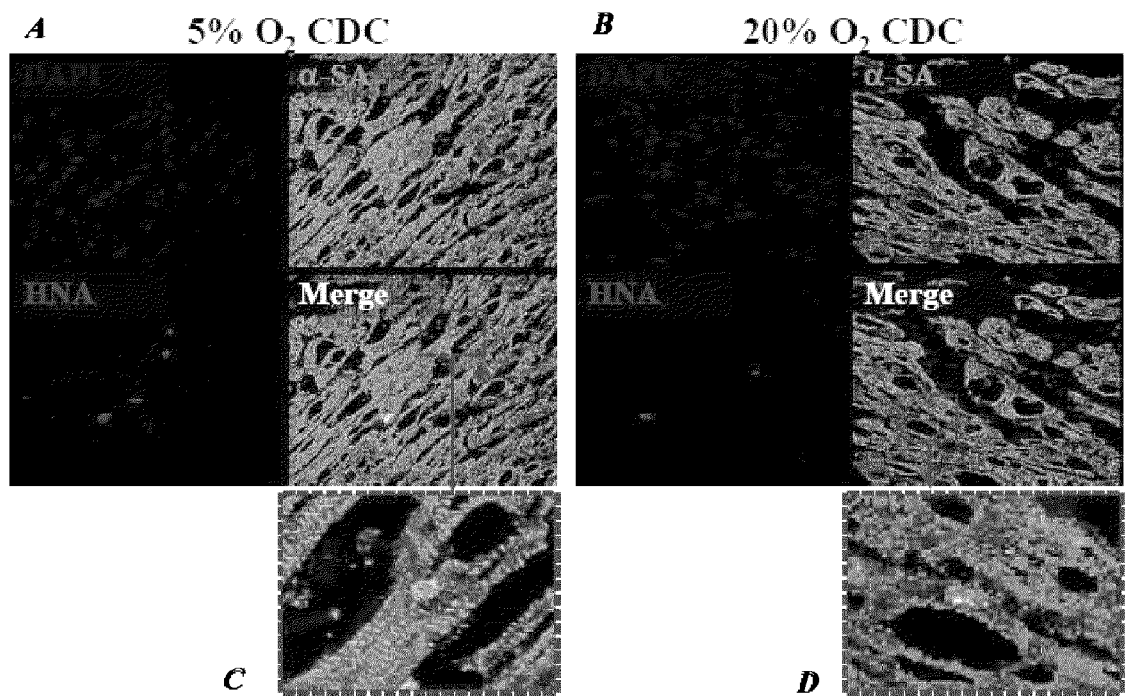
FIGS. 29A-29D depict immunostaining analysis showing that some human CDCs (identified by expression of human nuclear antigen, HNA) expanded in 5% $O_2$ (panel A) and 20% $O_2$ (panel B) expressed $\alpha$-sarcomeric actin ($\alpha$-SA), which is indicative of myogenic differentiation 3 weeks after implantation into infarcted hearts of mice. Image insets (panels C and D) show that the human nuclei are actually within cardiomyocytes.

By in vitro angiogenesis assay, CDCs expanded under both 5% $O_2$ and 20% $O_2$ could form capillary-like networks (tube formation) on matrigel in 6 h with hypoxic stimulation, and there was no significant difference between groups (see FIGS. 28A-28B).

In several embodiments, in vivo multilineage differentiation from human CDCs expanded under either 5% $O_2$ or 20% $O_2$, is achieved as well as the robust production of various angiogenic and anti-apoptotic growth factors in vitro. However, several embodiments are particularly advantageous in that the above results are achieved without the increased incidence of genomic instability. As such, cells cultured under physiologic oxygen concentrations are particularly advantageous for use in cellular therapies (e.g., cardiac stem cell therapy).

In vivo Cell Engraftment and Differentiation

Figures 22A, 22B, 22C, 22D, 22E:
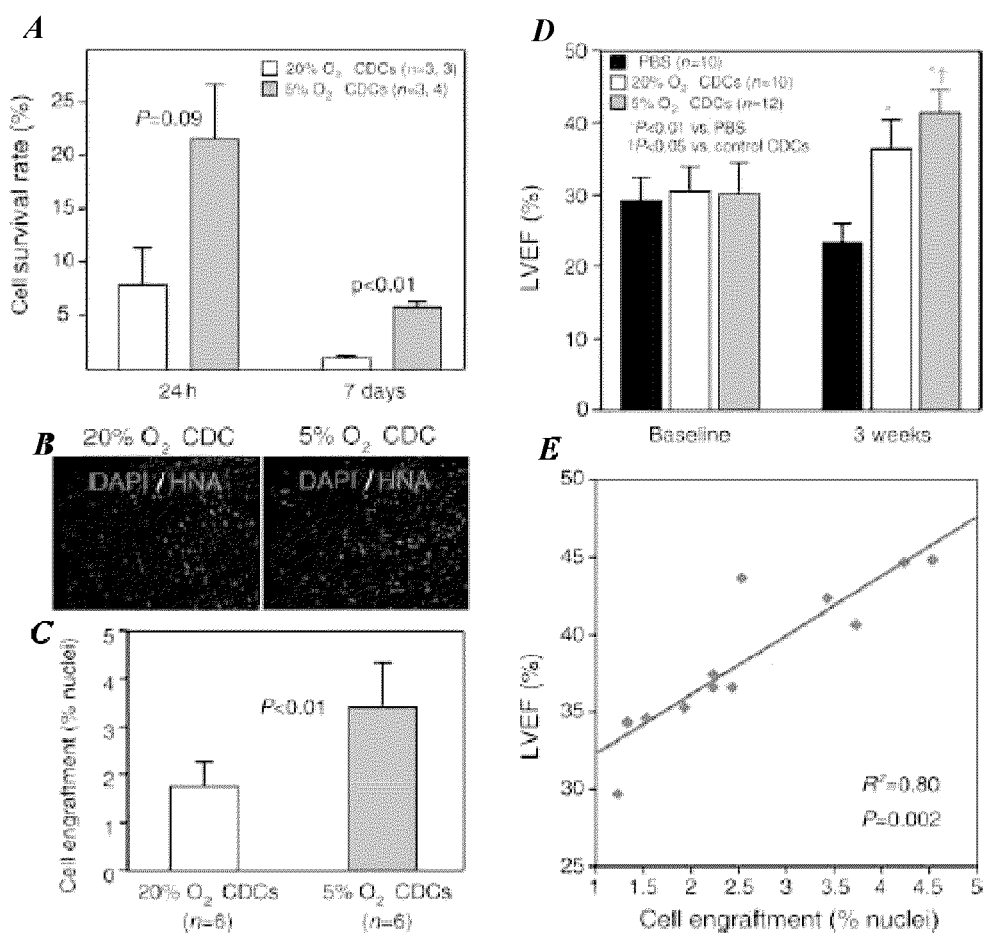
FIGS. 22A-22E depicts analysis of cell engraftment, cardiac functional recovery, and their relationships. Panel A depicts quantitative data on the survival rate of human CDCs 24 h and 7 days after implantation into mice-infarcted heart. Panel B shows cells positively stained by HNA are more frequently observed in mice 3 weeks after implantation with CDCs expanded in 5% $O_2$ than in 20% $O_2$. Panel C shows quantitative data for cell engraftment (% nuclei) in the infarcted heart. Panel D shows that left ventricular ejection fraction (LVEF) at baseline does not differ among groups, indicating a similar infarct size to begin with. After 3 weeks, the LVEF was higher in mice implanted with CDCs expanded in 5% $O_2$ than in 20% $O_2$, although the LVEF was also higher in mice implanted with CDCs expanded in 20% $O_2$ than in controls with PBS injection only. Panel D indicates that the engraftment of human CDCs (% nuclei) within the infarcted hearts of mice is strongly correlated with the absolute values of LVEF at 3 weeks.
Figures 23A, 23B, 23C, 23D, 23E, 23F, 23G:
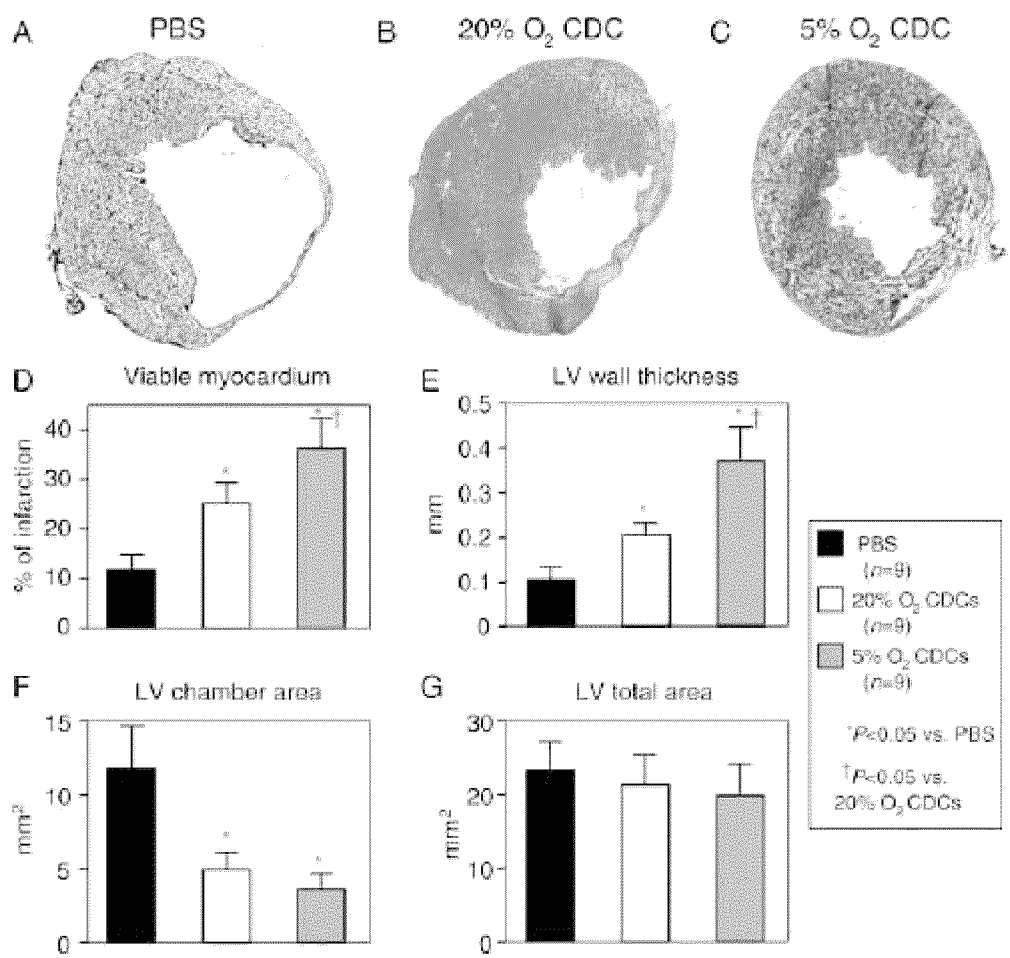
FIGS. 23A-23G depict histological assessments of infarct size and ventricular morphology. Representative images of Masson's staining show that, compared with an infarcted heart receiving PBS injection only (panel A), the infarct size was much smaller in a heart that had received CDCs expanded in both 5% $O_2$ (panel C) and 20% $O_2$ (panel B). Quantitative analyses of viable myocardium (panel D), LV wall thickness (panel E), LV chamber area (panel F), and LV total area (panel G) show that better therapeutic efficiency was achieved by the implantation of CDCs expanded in 5% $O_2$ than in 20% $O_2$, although a significant improvement was also observed by the implantation of CDCs expanded under 20% $O_2$ when compared with the control treatment with PBS injection only.
Figures 30A, 30B:
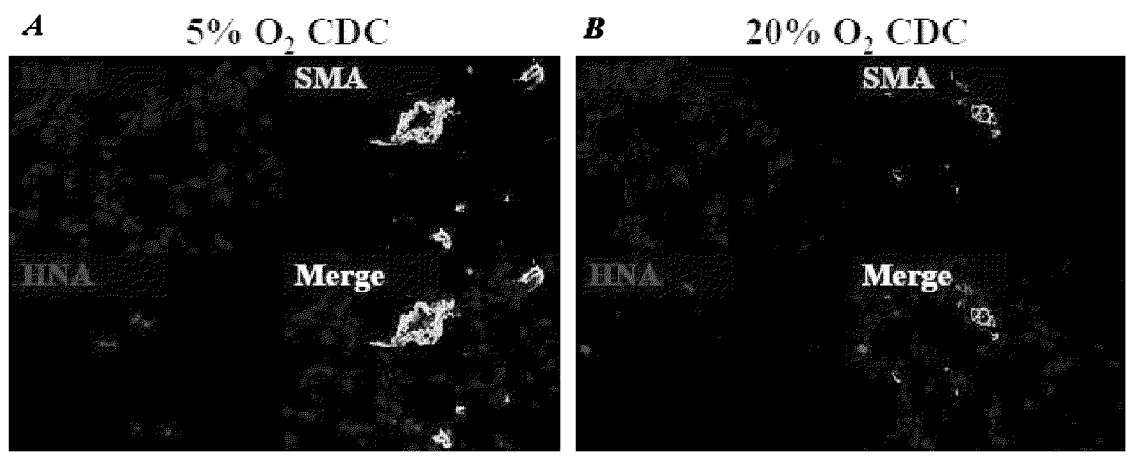
FIGS. 30A-30B depict immunostaining analysis shows some human cardiac-derived cells (CDCs, identified by human nuclear antigen, HNA) expanded in 5% $O_2$ (panel A) and 20% $O_2$ (panel B) expressed smooth muscle actin (SMA) 3 weeks after implantation into infarcted hearts of mice.
Figures 31A, 31B:
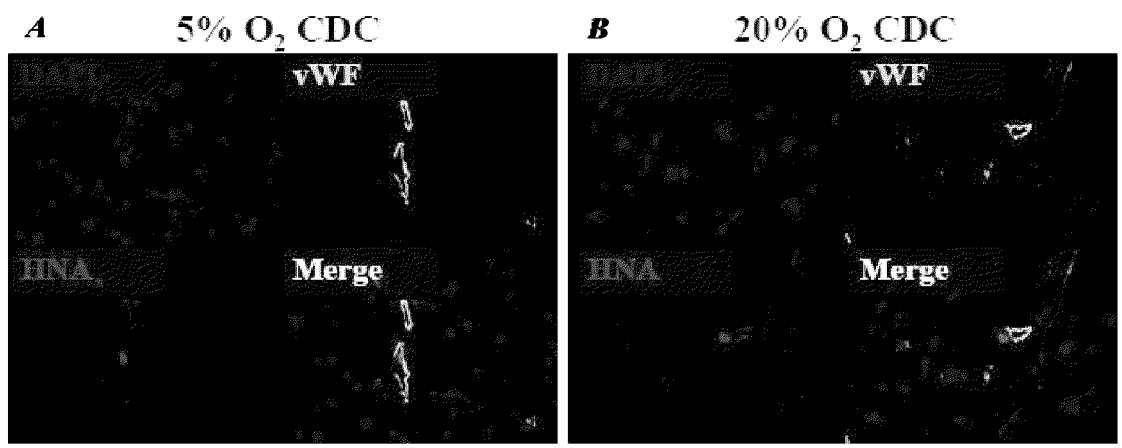
FIGS. 31A-31B depict immunostaining analysis shows some human cardiac-derived cells (CDCs, identified by human nuclear antigen, HNA) expanded in 5% $O_2$ (panel A) and 20% $O_2$ (panel B) expressed the endothelial marker von Willebrand factor (vWF) 3 weeks after implantation into infarcted hearts of mice.

The ultimate test of cell quality for cells to be used in cardiac regeneration and repair is the efficacy of the cells in vivo. Cell retention (24 h) and engraftment (7 days) in hearts injected with CDCs cultured in 5% $O_2$ or 20% $O_2$ was quantified. Quantitative PCR analysis showed that CDCs expanded in 5% $O_2$ survived better than CDCs expanded in 20% $O_2$, both at 24 h and at 7 days after implantation into the infarcted hearts of SCID mice (FIG. 22A). Furthermore, in the scar and marginal regions of the infarcted mouse heart 3 weeks after treatment, greater survival of CDCs expanded in 5% $O_2$ than in 20% $O_2$ was detected (FIG. 22A). Quantitative analysis of percentages of human nuclei revealed better cell engraftment after implantation of CDCs expanded under 5% $O_2$ than under 20% $O_2$ (3.40+0.94 vs. 1.77+0.52%, P<0.01, FIGS. 22B and 22C). The improvements in retention and engraftment suggest greater transplanted cell resilience, consistent with the observed increase in resistance to oxidative stress (FIGS. 21A and 21D) and the decrease in senescence (FIG. 20) in 5% $O_2$-cultured CDCs. One distinctive feature of CDCs is the ability to detect consistent cardiomyogenic and angiogenic differentiation of injected cells (e.g., direct regenerative effects), even though the mechanism of functional benefit appears, in some embodiments, to be largely paracrine-mediated. The present study also confirmed that CDCs can differentiate into cardiomyocytes, endothelial and vascular smooth muscle cells, irrespective of the level of oxygen in which they were cultured. Histology of mouse hearts that had been injected with CDCs 3 weeks earlier revealed expression of α-sarcomeric actin (see FIGS. 29A-29D), smooth muscle actin (see FIGS. 30A-30B), and vWF (see FIGS. 31A-31B) in some of the surviving progeny of human CDCs expanded in either 5% $O_2$ or 20% $O_2$, indicative of multilineage differentiation. Although CDCs expanded in 5% $O_2$ exhibited greater survival, their differentiation potential was not noticeably different than that of 20% $O_2$-cultured CDCs.

When implanted into infarcted hearts of SCID mice, 5% $O_2$-cultured human CDCs engrafted to a greater degree and improved function to a greater degree as compared to 20% $O_2$-cultured CDCs. As discussed above, the decrease in cell senescence and increased resistance to oxidative stress in vitro are, in some embodiments, at least partially responsible for the superior effects observed in vivo. Also as discussed above, it is believed that implantation of CDCs into infarcted heart leads to functional improvement via a direct regeneration, paracrine effects, or a combination thereof. Thus, in several embodiments, expansion of cardiac stem cells in physiologic oxygen concentrations augments the ability of the cells to effect cardiac repair and/or regeneration. In some embodiments, the cells cultured in physiologic oxygen concentrations engraft more readily than cells cultured in 20% $O_2$. In some embodiments, engraftment is more efficient (e.g., a greater proportion of administered cells engraft). In some embodiments, engraftment is for a longer term (e.g., engrafted cells cultured in physiologic oxygen concentrations survive longer than those cultured in 20% $O_2$. In several embodiments, increased engraftment or longer term engraftment is related to the decreased senescence of cells cultured in physiologic oxygen concentrations (e.g., the cells are more metabolically active and more readily survive in a new host environment).

While the present study did not attempt to quantify the relative roles of direct regeneration vs. indirect paracrine effects, in some embodiments, both direct and indirect effects are operative. As discussed above, direct effects (e.g., the differentiation of the administered cells into functional cardiac, vascular, or endothelial tissue are responsible for repair and/or regeneration of cardiac tissue, in some embodiments. In some embodiments, paracrine effects (e.g., growth factors, cytokines, or other signals/factors) generated by the administered cells serve to mediate cardiac tissue repair or regeneration. In some embodiments, combinations of direct and indirect mechanisms are involved.

Cardiac Function and Infarct Size

To assess efficacy in myocardial repair, left ventricular function in hearts injected with vehicle or with CDCs cultured in 5% $O_2$ or 20% $O_2$ was compared. Although LVEF at baseline did not differ between groups, LEVF measured 3 weeks after treatment was higher in mice implanted with 5% $O_2$-cultured CDCs as compared to those expanded in 20% $O_2$ (41.5+ 3.2 vs. 36.5+4.1%, P=0.043, FIG. 22D). Both cell groups outperformed the vehicle-treated group. In addition, the absolute values of LVEF correlate strongly with the degree of cell engraftment ($r^2$=0.80, P=0.002, FIG. 22E). Compared with the control treatment with PBS injection only, the implantation of CDCs expanded under either 5% $O_2$ or 20% $O_2$ results in obviously smaller infarct size, more viable myocardium, increased infarct wall thickness, and lower LV chamber area 3 weeks after treatment (P<0.05 vs. PBS, FIG. 23A-23G). These parameters showed greater improvements with administration of 5% $O_2$-cultured CDCs as compared to those expanded in 20% $O_2$ (P, 0.05). Thus, as discussed above, in several embodiments, culture of cells in physiologic oxygen concentrations augments the ability of the cells to effect cardiac repair. In some embodiments, use of physiologic oxygen concentrations during culture of cells to be administered improves the functional or anatomical endpoints (as compared to cells cultured in 20% oxygen) by at least about 5%. In some embodiments, cells cultured in physiologic oxygen concentrations improve functional or anatomic endpoints by about 5% to about 10%, about 10% to about 15%, about 15% to about 20%, and overlapping ranges thereof. In some embodiments, depending on the endpoint, use of physiologic oxygen concentrations during culture of cells to be administered improves the effects the therapy (e.g., the repair or regeneration of cardiac tissue) by about 2-fold, about 4-fold, about 6-fold, about 10-fold, about 20-fold, and overlapping ranges lying between these values.

In several embodiments, ex vivo expansion of human CDCs under physiological oxygen (5% $O_2$) results in one or more of the following: increases in cell yield, decreases in aneuploidy and cell senescence, and increases in resistance to oxidative stress. Furthermore, in some embodiments, CDCs expanded in 5% $O_2$ results in improved engraftment and functional benefit after implantation into infarcted hearts (or other damaged or diseased heart tissue).

Various modifications and applications of embodiments of the invention may be performed without departing from the true spirit or scope of the invention. Method steps disclosed herein need not be performed in the order set forth. It should be understood that the invention is not limited to the embodiments set forth herein for purposes of exemplification, but is to be defined only by a reading of the appended claims, including the full range of equivalency to which each element thereof is entitled.

What is claimed is:

1. A method for culturing cardiac stem cells for use in the repair or regeneration of cardiac tissue while reducing DNA damage during culturing, the method comprising:
   isolating cardiac stem cells, wherein said cardiac stem cells are isolated from healthy mammalian non-embryonic cardiac tissue; and
   culturing said isolated cardiac stem cells as a monolayer culture in a culture media comprising an antioxidant composition, said antioxidant composition comprising glutathione present in a concentration ranging from 5 to 20 µM, vitamin C present in a concentration ranging from 0.1 to 20 µM, and vitamin E present in a concentration ranging from 0.1 to 20 µM, wherein said antioxidant composition present in said culture media is sufficient to (i) reduce reactive oxygen species to a level which decreases oxidative stress induced DNA damage, (ii) not reduce markers of DNA repair mechanisms to a statistically significant degree, and (iii) not induce markers of DNA damage in said cardiac stem cells to a statistically significant degree, when compared to cardiac stem cells not contacted with said antioxidant composition.

2. The method according to claim 1, wherein said glutathione is present in a concentration of 10 µM.

3. The method of claim 1, wherein said at least one non-peptide antioxidant further comprises one or more of thiols and polyphenols.

4. The method of claim 1, wherein said at least one non-peptide antioxidant further comprises vitamin A.

5. The method of claim 1, wherein said at least one of said vitamin C and said vitamin E is present in a concentration of 10 µM.

6. The method of claim 1, wherein said reactive oxygen species are reduced by at least 10%.

7. The method of claim 1, wherein said markers of DNA repair mechanisms comprise one or more DNA repair enzymes selected from the group consisting of: ATM, ATR, Rad50, Rad51, Chk1, and Chk2.

8. The method of claim 1, wherein said markers of DNA damage comprise one or more of γ-$H_2$AX foci in cultured cells, γ-$H_2$AX mRNA, or γ-$H_2$AX protein.

9. The method of claim 1, wherein said culturing is for at least about 24 hours.

10. The method of claim 1, wherein said at least one peptide antioxidant is glutathione, wherein said glutathione is present in a concentration ranging from 10 µM, wherein said at least one non-peptide antioxidant comprises vitamin C and vitamin E, and wherein each of said vitamin C and vitamin E is present in a concentration ranging from about 10 µM.

* * * * *